(12) United States Patent
Hashida et al.

(10) Patent No.: US 7,115,373 B2
(45) Date of Patent: Oct. 3, 2006

(54) METHOD OF TESTING FOR ATOPIC DERMATITIS BY MEASURING EXPRESSION OF THE NOR-1 GENE

(75) Inventors: Ryoichi Hashida, Tsukuba (JP); Shinji Kagaya, Tokyo (JP); Yoshihiro Yayoi, Tokyo (JP); Yuji Sugita, Tsukuba (JP); Hirohisa Saito, Tokyo (JP)

(73) Assignees: Genox Research, Inc., Ibaraki (JP); Japan as Represented by General Director of Agency of National Center For Child Health & Development, Tokyo (JP)

( * ) Notice: Subject to any disclaimer, the term of this patent is extended or adjusted under 35 U.S.C. 154(b) by 8 days.

(21) Appl. No.: 10/608,863

(22) Filed: Jun. 27, 2003

(65) Prior Publication Data

US 2004/0214192 A1    Oct. 28, 2004

(30) Foreign Application Priority Data

Jun. 27, 2002   (JP) .............................. 2002-188490

(51) Int. Cl.
*C12Q 1/68*   (2006.01)
*C12N 5/08*   (2006.01)
*C07H 21/04*  (2006.01)

(52) U.S. Cl. .................... 435/6; 435/372; 536/23.5
(58) Field of Classification Search ................. 435/7.2, 435/6
See application file for complete search history.

(56) References Cited

U.S. PATENT DOCUMENTS 6,812,339 B1 * 11/2004 Venter et al. ............ 536/24.31

2002/0049151 A1   4/2002  Murphy et al.
2004/0214231 A1  10/2004  Hashida et al.

FOREIGN PATENT DOCUMENTS

| WO | WO 00/77202 A1 | 12/2000 |
|----|----------------|---------|
| WO | WO 01/70254 A1 | 9/2001  |
| WO | WO 01/87923 A1 | 11/2001 |

OTHER PUBLICATIONS

Haynes et al, 1998, Electrophoresis. 19(11): 1862-1871.*
Pirih, F.Q., et al., "Parathyroid hormone induces the nuclear orphan receptor NOR-1 in osteoblasts," *Biochem. and Biophys. Res. Comm.*, 306:144-150(2003).
Accession No. U12767, "Human mitogen induced nuclear orphan receptor (MINOR) mRNA, complete cds," submitted Jul. 29, 1994, Irving, S.G. (GenBank).
Hedvat, C.V. and Irving, S.G., "The Isolation and Characterization of MINOR, a Novel Mitogen-Inducible Nuclear Orphan Receptor," *Mol. Endo.*, 9(12):1692-1700 (1995).

* cited by examiner

*Primary Examiner*—Janet L. Andres
*Assistant Examiner*—Zachary C. Howard
(74) *Attorney, Agent, or Firm*—Hamilton, Brook, Smith & Reynolds, P.C.

(57) ABSTRACT

Genes whose expression differ between that in eosinophils collected from atopic dermatitis patients of the exabartation stage and those of the remission stage were searched via a differential display method. As a result, NOR-1 (MINOR) gene was successfully identified whose expression significantly increased in eosinophils of patients in the remission stage, a stage associated with a decrease of eosinophils. The present inventors discovered that the gene can be successfully employed in testing for allergic diseases and screening for candidate compounds for therapeutic agents.

4 Claims, 13 Drawing Sheets

SEQUENCE LISTING

<160> NUMBER OF SEQ ID NOS: 18

<210> SEQ ID NO 1
<211> LENGTH: 3794
<212> TYPE: DNA
<213> ORGANISM: Homo sapiens
<220> FEATURE:
<221> NAME/KEY: CDS
<222> LOCATION: (730)..(2607)

<400> SEQUENCE: 1

```
ataaatgacg tgccgagaga gcgagcgaac gcgcagccgg gagagcggag tctcctgcct      60 cccgccccc accctccag ctcctgctcc tcctccgctc cccatacaca gacgcgctca      120
cacccgctcc ctcactcgca cacacagaca caagcgcgca cacaggctcc gcacacacac      180
ttcgctctcc cgcgcgctca caccctctt gccctgagcc cttgccggtg cagcgcggcg      240
ccgcagctgg acgcccctcc cgggctcact ttgcaacgct gacggtgccg gcagtggccg      300
tggaggtggg aacagcggcg gcatcctccc ccctggtcac agcccaagcc aggacgcccg      360
cggaacctct cggctgtgct ctcccatgag tcgggatcgc agcatccccc accagccgct      420
caccgcctcc gggagccgct gggcttgtac accgcagccc ttccgggaca gcagctgtga      480
ctccccccca gtgcagattt cgggacagct ctctagaaac tcgctctaaa gacggaaccg      540
ccacagcact caaagcccac tgcggaagag ggcagcccgg caagcccggg ccctgagcct      600
ggacccttag cggtgccggg cagcactgcc ggcgcttcgc ctcgccggac gtccgctcct      660
cctacactct cagcctccgc tggagagacc cccagcccca ccattcagcg cgcaagatac      720
``` cctccagat atg ccc tgc gtc caa gcc caa tat agc cct tcc cct cca ggt     771
           Met Pro Cys Val Gln Ala Gln Tyr Ser Pro Ser Pro Pro Gly
             1               5                  10 tcc agt tat gcg gcg cag aca tac agc tcg gaa tac acc acg gag atc        819
Ser Ser Tyr Ala Ala Gln Thr Tyr Ser Ser Glu Tyr Thr Thr Glu Ile
 15                  20                  25                  30 atg aac ccc gac tac acc aag ctg acc atg gac ctt ggc agc act gag        867
Met Asn Pro Asp Tyr Thr Lys Leu Thr Met Asp Leu Gly Ser Thr Glu
                 35                  40                  45 atc acg gct aca gcc acc acg tcc ctg ccc agc atc agt acc ttc gtg        915
Ile Thr Ala Thr Ala Thr Thr Ser Leu Pro Ser Ile Ser Thr Phe Val
         50                  55                  60 gag ggc tac tcg agc aac tac gaa ctc aag cct tcc tgc gtg tac caa        963
Glu Gly Tyr Ser Ser Asn Tyr Glu Leu Lys Pro Ser Cys Val Tyr Gln
 65                  70                  75 atg cag cgg ccc ttg atc aaa gtg gag gag ggg cgg gcg ccc agc tac       1011
Met Gln Arg Pro Leu Ile Lys Val Glu Glu Gly Arg Ala Pro Ser Tyr
 80                  85                  90

-continued

| | | | | | | | | | | | | | | | |
|---|---|---|---|---|---|---|---|---|---|---|---|---|---|---|---|
| cat | cac | cat | cac | cac | cac | cac | cac | cac | cac | cac | cat | cac | cag | cag | 1059 |
| His | His | His | His | His | His | His | His | His | His | His | His | His | Gln | Gln | |
| 95 | | | | 100 | | | | | 105 | | | | | 110 | |

| | | | | | | | | | | | | | | | |
|---|---|---|---|---|---|---|---|---|---|---|---|---|---|---|---|
| cag | cat | cag | cag | cca | tcc | att | cct | cca | gcc | tcc | agc | ccg | gag | gac | gag | 1107 |
| Gln | His | Gln | Gln | Pro | Ser | Ile | Pro | Pro | Ala | Ser | Ser | Pro | Glu | Asp | Glu |
| | | | 115 | | | | | 120 | | | | | 125 | |

| gtg | ctg | ccc | agc | acc | tcc | atg | tac | ttc | aag | cag | tcc | cca | ccg | tcc | acc | 1155 |
|---|---|---|---|---|---|---|---|---|---|---|---|---|---|---|---|---|
| Val | Leu | Pro | Ser | Thr | Ser | Met | Tyr | Phe | Lys | Gln | Ser | Pro | Pro | Ser | Thr |
| | | | 130 | | | | | 135 | | | | | 140 | | |

| ccc | acc | acg | ccg | gcc | ttc | ccc | ccg | cag | gcg | ggg | gcg | tta | tgg | gac | gag | 1203 |
|---|---|---|---|---|---|---|---|---|---|---|---|---|---|---|---|---|
| Pro | Thr | Thr | Pro | Ala | Phe | Pro | Pro | Gln | Ala | Gly | Ala | Leu | Trp | Asp | Glu |
| | | 145 | | | | | 150 | | | | | 155 | | | |

| gca | ctg | ccc | tcg | gcg | ccc | ggc | tgc | atc | gca | ccc | ggc | ccg | ctg | ctg | gac | 1251 |
|---|---|---|---|---|---|---|---|---|---|---|---|---|---|---|---|---|
| Ala | Leu | Pro | Ser | Ala | Pro | Gly | Cys | Ile | Ala | Pro | Gly | Pro | Leu | Leu | Asp |
| 160 | | | | | 165 | | | | | 170 | | | | | |

| ccg | ccg | atg | aag | gcg | gtc | ccc | acg | gtg | gcc | ggc | gcg | cgc | ttc | ccg | ctc | 1299 |
|---|---|---|---|---|---|---|---|---|---|---|---|---|---|---|---|---|
| Pro | Pro | Met | Lys | Ala | Val | Pro | Thr | Val | Ala | Gly | Ala | Arg | Phe | Pro | Leu |
| 175 | | | | 180 | | | | | 185 | | | | | 190 | |

| ttc | cac | ttc | aag | ccc | tcg | ccg | ccg | cat | ccc | ccc | gcc | ccc | agc | ccg | gcc | 1347 |
|---|---|---|---|---|---|---|---|---|---|---|---|---|---|---|---|---|
| Phe | His | Phe | Lys | Pro | Ser | Pro | Pro | His | Pro | Pro | Ala | Pro | Ser | Pro | Ala |
| | | | 195 | | | | | 200 | | | | | 205 | | |

| ggc | ggc | cac | cac | ctc | ggc | tac | gac | ccg | acg | gcc | gct | gcc | gcg | ctc | agc | 1395 |
|---|---|---|---|---|---|---|---|---|---|---|---|---|---|---|---|---|
| Gly | Gly | His | His | Leu | Gly | Tyr | Asp | Pro | Thr | Ala | Ala | Ala | Ala | Leu | Ser |
| | | | 210 | | | | | 215 | | | | | 220 | | |

| ctg | ccg | ctg | gga | gcc | gca | gcc | gcc | gcg | ggc | agc | cag | gcc | gcc | gcg | ctt | 1443 |
|---|---|---|---|---|---|---|---|---|---|---|---|---|---|---|---|---|
| Leu | Pro | Leu | Gly | Ala | Ala | Ala | Ala | Ala | Gly | Ser | Gln | Ala | Ala | Ala | Leu |
| | | 225 | | | | | 230 | | | | | 235 | | | |

| gag | agc | cac | ccg | tac | ggg | ctg | ccg | ctg | gcc | aag | agg | gcg | gcc | ccg | ctg | 1491 |
|---|---|---|---|---|---|---|---|---|---|---|---|---|---|---|---|---|
| Glu | Ser | His | Pro | Tyr | Gly | Leu | Pro | Leu | Ala | Lys | Arg | Ala | Ala | Pro | Leu |
| | 240 | | | | | 245 | | | | | 250 | | | | |

| gcc | ttc | ccg | cct | ctc | ggc | ctc | acg | ccc | tcc | cct | acc | gcg | tcc | agc | ctg | 1539 |
|---|---|---|---|---|---|---|---|---|---|---|---|---|---|---|---|---|
| Ala | Phe | Pro | Pro | Leu | Gly | Leu | Thr | Pro | Ser | Pro | Thr | Ala | Ser | Ser | Leu |
| 255 | | | | | 260 | | | | | 265 | | | | | 270 |

| ctg | ggc | gag | agt | ccc | agc | ctg | ccg | tcg | ccg | ccc | agc | agg | agc | tcg | tcg | 1587 |
|---|---|---|---|---|---|---|---|---|---|---|---|---|---|---|---|---|
| Leu | Gly | Glu | Ser | Pro | Ser | Leu | Pro | Ser | Pro | Pro | Ser | Arg | Ser | Ser | Ser |
| | | | 275 | | | | | 280 | | | | | 285 | | |

| tct | ggc | gag | ggc | acg | tgt | gcc | gtg | tgc | ggg | gac | aac | gcc | gcc | tgc | cag | 1635 |
|---|---|---|---|---|---|---|---|---|---|---|---|---|---|---|---|---|
| Ser | Gly | Glu | Gly | Thr | Cys | Ala | Val | Cys | Gly | Asp | Asn | Ala | Ala | Cys | Gln |
| | | 290 | | | | | 295 | | | | | 300 | | | |

| cac | tac | ggc | gtg | cga | acc | tgc | gag | ggc | tgc | aag | ggc | ttt | ttc | aag | aga | 1683 |
|---|---|---|---|---|---|---|---|---|---|---|---|---|---|---|---|---|
| His | Tyr | Gly | Val | Arg | Thr | Cys | Glu | Gly | Cys | Lys | Gly | Phe | Phe | Lys | Arg |
| | | 305 | | | | | 310 | | | | | 315 | | | |

| aca | gtg | cag | aaa | aat | gca | aaa | tat | gtt | tgc | ctg | gca | aat | aaa | aac | tgc | 1731 |
|---|---|---|---|---|---|---|---|---|---|---|---|---|---|---|---|---|
| Thr | Val | Gln | Lys | Asn | Ala | Lys | Tyr | Val | Cys | Leu | Ala | Asn | Lys | Asn | Cys |
| | 320 | | | | | 325 | | | | | 330 | | | | |

| cca | gta | gac | aag | aga | cgt | cga | aac | cga | tgt | cag | tac | tgt | cga | ttt | cag | 1779 |
|---|---|---|---|---|---|---|---|---|---|---|---|---|---|---|---|---|
| Pro | Val | Asp | Lys | Arg | Arg | Arg | Asn | Arg | Cys | Gln | Tyr | Cys | Arg | Phe | Gln |
| 335 | | | | | 340 | | | | | 345 | | | | | 350 |

| aag | tgt | ctc | agt | gtt | gga | atg | gta | aaa | gaa | gtt | gtc | cgt | aca | gat | agt | 1827 |
|---|---|---|---|---|---|---|---|---|---|---|---|---|---|---|---|---|
| Lys | Cys | Leu | Ser | Val | Gly | Met | Val | Lys | Glu | Val | Val | Arg | Thr | Asp | Ser |
| | | | 355 | | | | | 360 | | | | | 365 | | |

| ctg | aaa | ggg | agg | aga | ggt | cgt | ctg | cct | tcc | aaa | cca | aag | agc | cca | tta | 1875 |
|---|---|---|---|---|---|---|---|---|---|---|---|---|---|---|---|---|
| Leu | Lys | Gly | Arg | Arg | Gly | Arg | Leu | Pro | Ser | Lys | Pro | Lys | Ser | Pro | Leu |
| | | 370 | | | | | 375 | | | | | 380 | | | |

| caa | cag | gaa | cct | tct | cag | ccc | tct | cca | cct | tct | cct | cca | atc | tgc | atg | 1923 |
|---|---|---|---|---|---|---|---|---|---|---|---|---|---|---|---|---|
| Gln | Gln | Glu | Pro | Ser | Gln | Pro | Ser | Pro | Pro | Ser | Pro | Pro | Ile | Cys | Met |
| | 385 | | | | | 390 | | | | | 395 | | | | |

| atg | aat | gcc | ctt | gtc | cga | gct | tta | aca | gac | tca | aca | ccc | aga | gat | ctt | 1971 |
|---|---|---|---|---|---|---|---|---|---|---|---|---|---|---|---|---|
| Met | Asn | Ala | Leu | Val | Arg | Ala | Leu | Thr | Asp | Ser | Thr | Pro | Arg | Asp | Leu |
| 400 | | | | | 405 | | | | | 410 | | | | | |

-continued

| | | |
|---|---|---|
| gat tat tcc aga tac tgt ccc act gac cag gct gct gca ggc aca gat<br>Asp Tyr Ser Arg Tyr Cys Pro Thr Asp Gln Ala Ala Ala Gly Thr Asp<br>415                    420                    425                    430 | 2019 |
| gct gag cat gtg caa caa ttc tac aac ctc ctg aca gcc tcc att gat<br>Ala Glu His Val Gln Gln Phe Tyr Asn Leu Leu Thr Ala Ser Ile Asp<br>                    435                    440                    445 | 2067 |
| gta tcc aga agc tgg gca gaa aag att ccg gga ttt act gat ctc ccc<br>Val Ser Arg Ser Trp Ala Glu Lys Ile Pro Gly Phe Thr Asp Leu Pro<br>                450                    455                    460 | 2115 |
| aaa gaa gat cag aca tta ctt att gaa tca gcc ttt ttg gag ctg ttt<br>Lys Glu Asp Gln Thr Leu Leu Ile Glu Ser Ala Phe Leu Glu Leu Phe<br>465                    470                    475 | 2163 |
| gtc ctc aga ctt tcc atc agg tca aac act gct gaa gat aag ttt gtg<br>Val Leu Arg Leu Ser Ile Arg Ser Asn Thr Ala Glu Asp Lys Phe Val<br>      480                    485                    490 | 2211 |
| ttc tgc aat gga ctt gtc ctg cat cga ctt cag tgc ctt cgt gga ttt<br>Phe Cys Asn Gly Leu Val Leu His Arg Leu Gln Cys Leu Arg Gly Phe<br>495                    500                    505                    510 | 2259 |
| ggg gag tgg ctc gac tct att aaa gac ttt tcc tta aat ttg cag agc<br>Gly Glu Trp Leu Asp Ser Ile Lys Asp Phe Ser Leu Asn Leu Gln Ser<br>                    515                    520                    525 | 2307 |
| ctg aac ctt gat atc caa gcc tta gcc tgc ctg tca gca ctg agc atg<br>Leu Asn Leu Asp Ile Gln Ala Leu Ala Cys Leu Ser Ala Leu Ser Met<br>530                    535                    540 | 2355 |
| atc aca gaa aga cat ggg tta aaa gaa cca aag aga gtc gaa gag cta<br>Ile Thr Glu Arg His Gly Leu Lys Glu Pro Lys Arg Val Glu Glu Leu<br>      545                    550                    555 | 2403 |
| tgc aac aag atc aca agc agt tta aaa gac cac cag agt aag gga cag<br>Cys Asn Lys Ile Thr Ser Ser Leu Lys Asp His Gln Ser Lys Gly Gln<br>560                    565                    570 | 2451 |
| gct ctg gag ccc acc gag tcc aag gtc ctg ggt gcc ctg gta gaa ctg<br>Ala Leu Glu Pro Thr Glu Ser Lys Val Leu Gly Ala Leu Val Glu Leu<br>575                    580                    585                    590 | 2499 |
| agg aag atc tgc acc ctg ggc ctc cag cgc atc ttc tac ctg aag ctg<br>Arg Lys Ile Cys Thr Leu Gly Leu Gln Arg Ile Phe Tyr Leu Lys Leu<br>                    595                    600                    605 | 2547 |
| gaa gac ttg gtg tct cca cct tcc atc att gac aag ctc ttc ctg gac<br>Glu Asp Leu Val Ser Pro Pro Ser Ile Ile Asp Lys Leu Phe Leu Asp<br>610                    615                    620 | 2595 |
| acc cta cct ttc taatcaggag cagtggagca gtgagctgcc tcctctccta<br>Thr Leu Pro Phe<br>          625 | 2647 |
| gcacctgctt gctacgcagc aaagggatag gtttggaaac ctatcatttc ctgtccttcc | 2707 |
| ttaagaggaa aagcagctcc tgtagaaagc aaagactttc ttttttttct ggctcttttc | 2767 |
| cttacaacct aaagccagaa aacttgcaga gtattgtgtt ggggttgtgt tttatattta | 2827 |
| ggcattgggg gatggggtgg gaggggggtta tagttcatga gggttttcta agaaattgct | 2887 |
| aacaaagcac ttttggacaa tgctatccca gcaggaaaaa aaggataat ataactgttt | 2947 |
| taaaactctt tctggggaat ccaattatag ttgctttgta tttaaaaaca agaacagcca | 3007 |
| agggttgttc gccagggtag gatgtgtctt aaagattggt cccttgaaaa tatgcttcct | 3067 |
| gtatcaaagg tacgtatgtg gtgcaaacaa ggcagaaact tcctttttaat ttccttcttc | 3127 |
| ctttatttta acaaatggtg aaagatggag gattacctac aaatcagaca tggcaaaaca | 3187 |
| ataatggctg tttgcttcca taaacaagtg caatttttta aagtgctgtc ttactaagtc | 3247 |
| ttgtttatta actctccttt attctatatg gaaatataaaa ggaggcagtc atgttagcaa | 3307 |

-continued

```
atgacacgtt aatatccta gcagaggctg tgttcacctt ccctgtcgat cccttctgag   3367
gtatggccca tccaagactt ttaggccatt cttgatggaa ccagatccct gccctgactg   3427
tccagctatc ctgaaagtgg atcagattat aaactggatt acatgtaact gttttggttg   3487
tgttctatca accccaccag agttccctaa acttgcttca gttatagtaa ctgactggta   3547
tattcattca gaagcgccat aagtcagttg agtatttgat ccctagataa gaacatgcaa   3607
atcagcagga actggtcata cagggtaagc accagggaca ataaggattt ttatagatat   3667
aatttaattt ttgttattgg ttaaggagac aattttggag agcaagcaaa tcttttttaaa  3727 aaatagtatg aatgtgaata ctagaaaaga tttaaaaaat agtatgagtg tgagtactag   3787
gaaggat                                                             3794
```

<210> SEQ ID NO 2
<211> LENGTH: 626
<212> TYPE: PRT
<213> ORGANISM: Homo sapiens

<400> SEQUENCE: 2

```
Met Pro Cys Val Gln Ala Gln Tyr Ser Pro Ser Pro Pro Gly Ser Ser
  1               5                  10                  15

Tyr Ala Ala Gln Thr Tyr Ser Ser Glu Tyr Thr Thr Glu Ile Met Asn
                 20                  25                  30

Pro Asp Tyr Thr Lys Leu Thr Met Asp Leu Gly Ser Thr Glu Ile Thr
             35                  40                  45

Ala Thr Ala Thr Thr Ser Leu Pro Ser Ile Ser Thr Phe Val Glu Gly
         50                  55                  60

Tyr Ser Ser Asn Tyr Glu Leu Lys Pro Ser Cys Val Tyr Gln Met Gln
 65                  70                  75                  80

Arg Pro Leu Ile Lys Val Glu Glu Gly Arg Ala Pro Ser Tyr His His
                 85                  90                  95

His His His His His His His His His His His Gln Gln Gln His
                100                 105                 110

Gln Gln Pro Ser Ile Pro Pro Ala Ser Ser Pro Glu Asp Glu Val Leu
            115                 120                 125

Pro Ser Thr Ser Met Tyr Phe Lys Gln Ser Pro Pro Ser Thr Pro Thr
        130                 135                 140

Thr Pro Ala Phe Pro Pro Gln Ala Gly Ala Leu Trp Asp Glu Ala Leu
145                 150                 155                 160

Pro Ser Ala Pro Gly Cys Ile Ala Pro Gly Pro Leu Leu Asp Pro Pro
                165                 170                 175

Met Lys Ala Val Pro Thr Val Ala Gly Ala Arg Phe Pro Leu Phe His
            180                 185                 190

Phe Lys Pro Ser Pro Pro His Pro Pro Ala Pro Ser Pro Ala Gly Gly
        195                 200                 205

His His Leu Gly Tyr Asp Pro Thr Ala Ala Ala Leu Ser Leu Pro
    210                 215                 220

Leu Gly Ala Ala Ala Ala Gly Ser Gln Ala Ala Leu Glu Ser
225                 230                 235                 240

His Pro Tyr Gly Leu Pro Leu Ala Lys Arg Ala Ala Pro Leu Ala Phe
                245                 250                 255

Pro Pro Leu Gly Leu Thr Pro Ser Pro Thr Ala Ser Ser Leu Leu Gly
            260                 265                 270

Glu Ser Pro Ser Leu Pro Ser Pro Pro Ser Arg Ser Ser Ser Ser Gly
        275                 280                 285
```

```
Glu Gly Thr Cys Ala Val Cys Gly Asp Asn Ala Ala Cys Gln His Tyr
    290                 295                 300
Gly Val Arg Thr Cys Glu Gly Cys Lys Gly Phe Phe Lys Arg Thr Val
305                 310                 315                 320
Gln Lys Asn Ala Lys Tyr Val Cys Leu Ala Asn Lys Asn Cys Pro Val
                325                 330                 335
Asp Lys Arg Arg Arg Asn Arg Cys Gln Tyr Cys Arg Phe Gln Lys Cys
            340                 345                 350
Leu Ser Val Gly Met Val Lys Glu Val Val Arg Thr Asp Ser Leu Lys
        355                 360                 365
Gly Arg Arg Gly Arg Leu Pro Ser Lys Pro Lys Ser Pro Leu Gln Gln
370                 375                 380
Glu Pro Ser Gln Pro Ser Pro Pro Ser Pro Pro Ile Cys Met Met Asn
385                 390                 395                 400
Ala Leu Val Arg Ala Leu Thr Asp Ser Thr Pro Arg Asp Leu Asp Tyr
                405                 410                 415
Ser Arg Tyr Cys Pro Thr Asp Gln Ala Ala Ala Gly Thr Asp Ala Glu
            420                 425                 430
His Val Gln Gln Phe Tyr Asn Leu Leu Thr Ala Ser Ile Asp Val Ser
        435                 440                 445
Arg Ser Trp Ala Glu Lys Ile Pro Gly Phe Thr Asp Leu Pro Lys Glu
    450                 455                 460
Asp Gln Thr Leu Leu Ile Glu Ser Ala Phe Leu Glu Leu Phe Val Leu
465                 470                 475                 480
Arg Leu Ser Ile Arg Ser Asn Thr Ala Glu Asp Lys Phe Val Phe Cys
                485                 490                 495
Asn Gly Leu Val Leu His Arg Leu Gln Cys Leu Arg Gly Phe Gly Glu
            500                 505                 510
Trp Leu Asp Ser Ile Lys Asp Phe Ser Leu Asn Leu Gln Ser Leu Asn
        515                 520                 525
Leu Asp Ile Gln Ala Leu Ala Cys Leu Ser Ala Leu Ser Met Ile Thr
    530                 535                 540
Glu Arg His Gly Leu Lys Glu Pro Lys Arg Val Glu Glu Leu Cys Asn
545                 550                 555                 560
Lys Ile Thr Ser Ser Leu Lys Asp His Gln Ser Lys Gly Gln Ala Leu
                565                 570                 575
Glu Pro Thr Glu Ser Lys Val Leu Gly Ala Leu Val Glu Leu Arg Lys
            580                 585                 590
Ile Cys Thr Leu Gly Leu Gln Arg Ile Phe Tyr Leu Lys Leu Glu Asp
        595                 600                 605
Leu Val Ser Pro Pro Ser Ile Ile Asp Lys Leu Phe Leu Asp Thr Leu
    610                 615                 620
Pro Phe
625
```

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3 gtttttttttt tttttta                                                17

-continued

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4 gtttttttttt tttttc                                                      17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5 gtttttttttt tttttg                                                      17

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
cattctcagg                                                              10

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
tgccttgtct agaactgcac ag                                                22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
aagtgtgttg gaccaagcag c                                                 21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Probe Sequence

<400> SEQUENCE: 9
aagtcagtgc agagcctgga tgagga                                            26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
tcacccacac tgtgcccatc tacga                                            25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
cagcggaacc gctcattgcc aatgg                                            25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Probe Sequence
<220> FEATURE:
<221> NAME/KEY: misc_binding
<222> LOCATION: (1)
<223> OTHER INFORMATION: Label FAM
<220> FEATURE:
<221> NAME/KEY: misc_binding
<222> LOCATION: (7)
<223> OTHER INFORMATION: Label TAMRA

<400> SEQUENCE: 12
atgccctccc ccatgccatc ctgcgt                                           26

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
gttccaggca ataacatcat acc                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
gctacttgtg aaactcccaa atg                                              23

<210> SEQ ID NO 15
<211> LENGTH: 2087
<212> TYPE: DNA
<213> ORGANISM: Homo sapiens

```
<400> SEQUENCE: 15
ggcaaaaatc tgtactttaa aaagtgccat tggatgattc tttggcacac taaggtttga      60
gaaccatcga tatagtttat aataacaact caattttacc ttgaattttc cagcttttcc     120
tggggttgag aagggatgag caatagagat ataaattttc ctgaaagcaa tcaattcatt     180
taacaaatac ttactgaatg gctgctaggt agtaggcact gttccagggc aatggacacg     240
ttgctgaaca agacaaagcc cttatccaca tgaaccttac atacctgtaa aggagaaaaa     300
gagtaaacaa atatacaatt gcagtgatgt cattggtggg aggagaggaa ttttttgctt     360 tttgctttt ggagtggggg catagagtta gatcagaaaa gaaaaaattg ggggaaaat      420 atattcattg ccaatttta aaatgtcact ttttaaagtg taagaaccta agaatatgta     480
tacatagttt gacttataca atgatcacat ctaaaatttt tagagctata gttgagaaaa     540
gtaacatttt aaggggagaa aaacgtgtcc ttagcgtagt ctacatattt agccagggct     600
gaaagtgaga tagagtaaat attagattcc actctgctat taaagcctca catcactaat     660
ttttgagggg tggtgttttc catgggtctc acttaatttc cacacaaata tctcatttgg     720
ggcctgggct attgctgaag tctgacttgt atagctgcgt tactgccata tgaaacacac     780
agacccattt tagtttacat aatatccatt gctgttgttt gcagctctag attcccattc     840
taggtgcttt agagaaacct tccttaggca ttggctgtca gtaaatgtaa tactgtgtct     900
ttgactagtg agaaagccag agttctgaca gatcaataac ccctataggg tggaaaaaaa     960
ttagtataaa caggaaaaaa gttcacttaa aaaaatcttt ttgcatttga cctatgttcg    1020
attggcatga tcagtaagca aatatttcta gattttcttt gtcaaacccc aaacctactt    1080
agcccagaga cagagcaatc aatgtagggc agcagagaca cagagctggg agtccagtcc    1140
ttccaactct aggaccagta ttcattgggt gaggttttcc taaactggta ggccaggcag    1200
agaaaaaatc taaaacgttt tgttccgttc ctttacatct tatgtccaat agaggagatt    1260
tttcttttcc tccagcattg gatgctgacc ctccagtcac ccccaagtta ctggtggctc    1320
agactgaatt cactttggct ccaaaattct gagacttgga ccaaaaccac tgcaggtgaa    1380
gcccagagga tctggctgga gcctggcagg ctgggccggc tggctttcct tcttgctggg    1440
ctccatcaga gaaagtaca cacacagggt gggcagggac ttcacttccc tgtgtgcaga    1500
aggcatgaaa tgtgagccca gcaggggcag aagcctgcag aggaccctgg gtgaaagcta    1560
cacactttga tggattctga acaaatattg gaagcagaga gattgttgag ttgtgagcca    1620
tggattcagg ggagtcagtg caggaggtag ctgtcagatc cattctcagg ggaaactatt    1680
cattctttag tctttttctc tctcccacta ttttaaaaca aaataatgct gaatcagtgt    1740
caagttccag gcaataacat catacctggt gtgatttagc aatatttaga atcatttaat    1800
gcaagagcca gaagtaatct tagggatcag gtagtccact ttattcctgt tccagagact    1860
gaaactgact cagagaggtt aaatgccttg tctagaactg cacagcaagt cagtgcagag    1920
cctggatgag gacccccatga cctgctgctt ggtccaacac actttccttt actcccactc    1980
atttgggagt ttcacaagta gctccctcag cttttgaaag ggaggatctg ccctgaattt    2040
cattctgctc ttggagagcc tgtggaatta ttaaataaat tcataaa                  2087

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:Artificially
```

```
                                  -continued

Synthesized Primer Sequence

<400> SEQUENCE: 16
tgggtgccct ggtagaact                                                  19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
gcttcaggta gaagatgcgc t                                               21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Probe Sequence

<400> SEQUENCE: 18
aggaagatct gcaccctggg cctc                                            24
```

METHOD OF TESTING FOR ATOPIC DERMATITIS BY MEASURING EXPRESSION OF THE NOR-1 GENE

RELATED APPLICATION

This application claims priority under 35 U.S.C. § 119 or 365 to Japan Application No. 2002-188490, filed Jun. 27, 2002. The entire teachings of the above application are incorporated herein by reference.

FIELD OF THE INVENTION

The present invention relates to a method of testing for allergic diseases and a method for screening candidate compounds as therapeutic agents for an allergic disease using the expression of NOR-1 gene related to allergic diseases as an index. The present invention is also directed towards pharmaceutical agents for treating allergic diseases.

BACKGROUND OF THE INVENTION

Allergic diseases such as atopic dermatitis are considered multifactorial diseases. These diseases are caused by the interaction of many different genes whose expression is independently influenced by multiple environmental factors. Thus, determination of specific genes causing a specific disease has been extremely difficult for allergic diseases.

Furthermore, the expression of mutated or defective genes or overexpression or reduced expression of specific genes is assumed involved in allergic diseases. Therefore, to elucidate the role of gene expression in diseases, it is necessary to understand how a gene is involved at the onset of a disease and how the expression of the gene is altered by external stimulants such as drugs.

Recent developments in gene expression analysis techniques have enabled analysis and comparison of gene expression of many clinical samples. Among these methods, the differential display (DD) method is useful. Liang and Pardee originally developed this method in 1992 (Science, 1992, 257: 967–971). According to this method, several tens or more different samples can be screened at one time to detect genes whose expressions are different among the samples. Important information to reveal the causative gene of a disease is expected to be obtained by examining genes with mutations or genes whose expression changes depending on the time and environment. Such genes include those whose expression is influenced by environmental factors.

Medical examination by interview with the patient, confirmation of family history and anamnesis of the patient are generally important for recent diagnosis of allergic diseases. Furthermore, methods of diagnosing allergies based on information that is more objective include a method in which patient's blood sample is tested and a method of observing patient's immune response to allergen. Examples of the former method are the allergen-specific IgE measurement, leukocyte histamine release test and lymphocyte blast transformation test. The presence of allergen-specific IgE verifies the allergic reaction against the allergen. However, allergen-specific IgE is not always detected in every patient. Furthermore, the principle of IgE assay requires performing tests for all of the allergens necessary for diagnosis. The leukocyte histamine release test and lymphocyte blast transformation test are methods for observing the reaction of the immune system toward a specific allergen in vitro. These methods require complex operation.

Another known method for allergy diagnosis is based on the immune response observed at the time when a patient contacts an allergen (latter method). Such tests include the prick test, scratch test, patch test, intradermal reaction and induction test. These tests allow direct diagnosis of a patient's allergic reaction, but are highly invasive tests because the patients are actually exposed to allergen.

In addition, regardless of the allergen types, methods to confirm the involvement of an allergic reaction are also attempted. For example, a high serum IgE titer indicates the occurrence of allergic reaction in a patient. The serum IgE titer corresponds to the total amount of allergen-specific IgE. Though it is easy to determine the total amount of IgE regardless of the type of allergen, IgE titer may be reduced in some patients, for example, those with non-atopic bronchitis.

The number of eosinophils and eosinophil cationic protein (ECP) levels are diagnostic items for delayed-type reaction following Type I allergy and allergic inflammatory reaction. The number of eosinophils is considered to reflect the progress of allergic symptoms. ECP, a protein contained in eosinophil granules, is also strongly activated in patients with an asthma attack. Indeed, symptoms of allergies can be identified using these diagnostic items. However, only limited range of values can be used as a diagnostic index.

Therefore, diagnostic indices, regardless of the type of allergen, useful in comprehending pathological conditions of allergic disease patients and for determining the treatment regimen for the disease have been greatly needed in the art. Markers for allergic disease that are not only less harmful to patients but also capable of readily providing information required for diagnosis would be of great use. Identification of genes associated with allergic diseases enables tests for allergic diseases via the use of the expression of the genes as indexes. Furthermore, elucidation of the function of proteins encoded by the genes at the cell level is expected to promote, based on findings relating to their function, development of therapeutic methods and pharmaceutical agents for treating allergic diseases.

SUMMARY OF THE INVENTION

The present invention was achieved in the light of the above context, and the objective of the invention is to identify a gene associated with allergic diseases. Furthermore, another objective of the present invention is to provide a method of testing for allergic diseases and a method of screening for candidate compounds for a therapeutic agent for an allergic disease, both using the expression of the gene as an index, as well as pharmaceutical agents for treating allergic diseases.

Based on a previously established procedure, the "fluorescent differential display method (Fluorescent DD method)" (T. Ito et al. 1994, FEBS Lett. 351: 231–236), the present inventors developed a new DD system capable of analyzing leukocyte RNA samples prepared from multiple human blood samples (Japanese Patent Application No. Hei 11-120489). Utilizing the DD system, the present inventors tried to identify genes whose expression level is altered in an allergic disease-specific manner.

Specifically, first, the present inventors compared several parameters relating to allergic symptoms in patients with atopic dermatitis (a typical allergic disease), between the exacerbation stage and the remission stage of dermatitis conditions. As a result, decrease of eosinophils in the remission stage was observed in some patients. Since eosinophils are generally used as a typical clinical index for atopic dermatitis, the present inventors focused on this aspect. Furthermore, they considered that a gene directly involved in atopic dermatitis may be isolated by isolating a gene whose expression level in eosinophils differs between the exacerbation stage and the remission stage of a patient.

Therefore, eosinophils were collected from several subjects in the exacerbation stage and the remission stage of atopic dermatitis, and genes whose expression level alters in the eosinophils were screened using the aforementioned system. As a result, the present inventors succeeded in isolating sequence "2250-01" that showed a significantly higher expression level in patients that were observed to show a decrease of eosinophils in the remission stage. Genomic database analysis revealed this sequence as the intronic region of a nuclear orphan receptor called NOR-1 (MINOR). Therefore, the expression of the reported exon sequence of NOR-1(MINOR) was determined and, like the expression of the intronic region, found to be induced in the remission stage of subjects who clearly showed a decrease of eosinophils. No relation of the NOR-1 gene to allergic diseases has been reported so far.

The elevation of a gene that is suggested to have apoptotic character observed in peripheral blood eosinophils during the remission stage during treatment of atopic dermatitis corresponds well with the decrease in the number of peripheral blood eosinophils. Therefore, the induction of the NOR-1 gene expression would be correlated with therapeutic effect.

Using the expression level of the NOR-1 gene of this invention as an index, allergic diseases may be tested.

Furthermore, NOR-1 receptor is an orphan receptor and hitherto, neither the native ligand nor activator of the receptor had been found. The present inventors developed a high-throughput system for searching ligands and using this system, succeeded in obtaining a compound that may have a function to activate NOR-1 transcription. This compound is a prostaglandin (PGA derivative) comprising a cyclopentenone structure and may be the native ligand of the NOR-1 receptor. Furthermore, experiments using mutants wherein the ligand-binding domain (LBD) region of the receptor is deleted indicated that the prostaglandin derivative actually functions by acting on the LBD region of the receptor. Moreover, experiments utilizing BIAcor demonstrated the binding of the PGA derivative to NOR-1.

Thus, the present inventors found that screening of candidate compounds for a therapeutic agent for an allergic disease is possible, and the PGA derivative is a ligand activator of NOR-1.

Furthermore, using a pharmacophore model, the present inventors simulated the binding site of the PGA derivative to the NOR-1 ligand binding domain, and based on information on structure-activity relationship for the reporter system of the PGA derivative, compounds other than the PGA derivative that match with the binding pocket were selected from the database. These compounds are expected to function as ligands of the NOR-1 receptor.

Therapeutic effects on allergic diseases are expected for compounds that induce expression of the NOR-1 gene, or compounds that bind to the NOR-1 receptor and promote its transcription activity (for example, ligand activators).

Furthermore, the present inventors found for the first time that the expression of NOR-1 in cultured peripheral blood eosinophils is dramatically induced due to apoptosis stimulation of the cell with anti-CD30 antibody that has an agonist activity towards eosinophil CD30. Therefore, a therapeutic agent for allergic diseases is provided, which agent has the mechanism of increasing the expression of the NOR-1 gene by eosinophil CD30 ligand stimulation and inducing apoptosis of eosinophils by regulating the expression of downstream genes of Nor1.

The present inventors further succeeded in engineering a transgenic mouse wherein the expression of the human NOR-1 gene is induced through an actin promoter. This mouse is extremely useful as an animal model for analyzing allergic diseases mediated via NOR-1.

The present invention relates to a method of testing for allergic diseases and a method for screening candidate compounds as therapeutic agents for an allergic disease. These methods are performed using, as an index, the expression of the NOR-1 gene that shows high expression during allergic diseases, particularly in the remission stage associated with the decrease of eosinophils. The present invention also relates to pharmaceutical agents for treating allergic diseases. Specifically, the present invention provides:

[1] a method of testing for an allergic disease, said method comprising the steps of:
 (a) measuring the expression level of NOR-1 receptor protein or a gene encoding the protein in eosinophil cells of a test subject; and
 (b) comparing the expression level with that in eosinophil cells of a healthy subject;

[2] the testing method of [1], wherein the gene expression level is measured by cDNA PCR;

[3] the testing method of [1] or [2], wherein the allergic disease is atopic dermatitis;

[4] a reagent for testing for an allergic disease, said reagent comprising an oligonucleotide that has a length of at least 15 nucleotides and comprises a nucleotide sequence complementary to a polynucleotide encoding an NOR-1 receptor protein or to its complementary strand;

[5] a method of detecting the influence of a candidate compound on the expression level of a polynucleotide of (a) or (b) below, wherein said method comprises the steps of:
 (1) contacting the candidate compound with a cell that expresses a polynucleotide of (a) or (b):
  (a) a polynucleotide encoding an NOR-1 receptor protein; and
  (b) a polynucleotide encoding a protein whose expression in eosinophils increases in association with the decrease of eosinophils in the remission stage of atopic dermatitis, wherein said polynucleotide hybridizes under stringent conditions with a polynucleotide encoding an NOR-1 receptor protein; and
 (2) measuring the expression level of the polynucleotide (a) or (b);

[6] the method of [5], wherein the cell is a leukocyte cell line;

[7] a method of detecting the influence of a candidate compound on the expression level of a polynucleotide of (a) or (b) below, wherein said method comprises the steps of:
 (1) administering the candidate compound to a test animal; and
 (2) measuring, in the eosinophil cells of the test animal, the expression intensity of a polynucleotide of (a) or (b):
  (a) a polynucleotide encoding an NOR-1 receptor protein; and
  (b) a polynucleotide encoding a protein whose expression in eosinophils increases in association with the decrease of eosinophils in the remission stage of atopic dermatitis, wherein said polynucleotide hybridizes under stringent conditions with a polynucleotide encoding an NOR-1 receptor protein;

[8] a method of screening for a compound that increases the expression level of the polynucleotide (a) or (b), wherein said method comprises the steps of detecting the influence on the expression level by the method of any one of [5] to [7], and selecting a compound that increases the expression level compared to a control;

[9] a method of detecting the influence of a candidate compound on the expression level of a polynucleotide encoding an NOR-1 receptor protein, wherein said method comprises the steps of:
 (1) contacting a candidate compound with a cell or cell extract containing a DNA having a structure such that the transcription regulatory region of a gene encoding an NOR-1 receptor protein and a reporter gene are operably linked; and
 (2) measuring the activity of the reporter gene;

[10] a method of screening for a candidate compound that increases the expression level of a gene encoding an NOR-1 receptor protein, wherein said method comprises the steps of detecting the influence of a compound on the activity by the method of [9], and selecting a compound that increases the activity compared to a control;

[11] a method of screening for a candidate compound for a therapeutic agent for an allergic disease, wherein said method comprises the steps of:
 (1) contacting a test compound with an NOR-1 receptor protein;
 (2) measuring the binding activity between the test compound and the NOR-1 receptor protein; and
 (3) selecting a compound that binds to the NOR-1 receptor protein;

[12] a method of screening for a candidate compound for a therapeutic agent for an allergic disease, wherein said method comprises the steps of:
 (1) providing cells transfected with (a) a DNA that can express a fusion protein of an NOR-1 receptor protein or its ligand binding domain and a transcription regulatory region binding protein, and (b) a DNA having a structure such that a reporter gene is operably linked downstream of a DNA sequence to which the transcription regulatory region binding protein binds;
 (2) contacting the cell with a test compound;
 (3) measuring the activity of the reporter gene; and
 (4) selecting a compound that changes the activity;

[13] a therapeutic agent for an allergic disease, said agent comprising, as an active ingredient, a compound obtainable by the screening method of any one of [10] to [12];

[14] a therapeutic agent for an allergic disease, said agent comprising, as an active ingredient, a prostaglandin having a cyclopentenone structure, which is obtainable by the screening method of any one of [10] to [12];

[15] a therapeutic agent for an allergic disease, said agent comprising, as an active ingredient, a ligand of an NOR-1 receptor;

[16] the therapeutic agent for an allergic disease of [15], wherein the ligand of an NOR-1 receptor is a prostaglandin having a cyclopentenone structure;

[17] the therapeutic agent for an allergic disease of [16], wherein the prostaglandin having a cyclopentenone structure is selected from the group consisting of prostaglandin $A_2$, prostaglandin $A_1$, 16,16-dimethyl prostaglandin $A_2$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $J_2$, and 8-iso prostaglandin $A_1$;

[18] the therapeutic agent for an allergic disease of [15], wherein the ligand of an NOR-1 receptor is any one of the compounds listed in Tables 14 to 58;

[19] the therapeutic agent for an allergic disease of any one of [13] to [18], wherein the allergic disease is atopic dermatitis;

[20] an animal model for an allergic disease, wherein the animal model is a transgenic non-human vertebrate wherein the expression intensity of polynucleotide (a) or (b) below is decreased in eosinophil cells:
 (a) a polynucleotide encoding an NOR-1 receptor protein; and
 (b) a polynucleotide encoding a protein whose expression in eosinophils increases in association with the decrease of eosinophils in the remission stage of atopic dermatitis, wherein said polynucleotide hybridizes under stringent conditions with a polynucleotide encoding an NOR-1 receptor protein;

[21] the animal model of [20], wherein the transgenic animal is a knockout animal;

[22] a method of inducing apoptosis of a cell, said method comprising activation of an NOR-1 receptor protein in the cell;

[23] the apoptosis induction method of [22], which comprises the step of contacting a cell with a compound or a prostaglandin having a cyclopentenone structure, which is obtainable by the screening method of any one of [10] to [12];

[24] the apoptosis induction method of [22] or [23], wherein said cell is an eosinophil cell;

[25] an apoptosis inducing agent, which comprises a compound or a prostaglandin having a cyclopentenone structure, which is obtainable by the screening method of any one of [10] to [12];

[26] an apoptosis-inducing agent comprising a ligand of an NOR-1 receptor as an active ingredient;

[27] the apoptosis-inducing agent of [26], wherein the ligand of an NOR-1 receptor is a prostaglandin having a cyclopentenone structure;

[28] the apoptosis-inducing agent of [27], wherein the prostaglandin having a cyclopentenone structure is selected from the group consisting of prostaglandin $A_2$, prostaglandin $A_1$, 16,16-dimethyl prostaglandin $A_2$, 15 (R)-15-methyl prostaglandin $A_2$, 16-phenoxy tetranor prostaglandin $A_2$, 17-phenyl trinor prostaglandin $A_2$, 15-deoxy-delta 12,14-prostaglandin $J_2$, and 8-iso prostaglandin $A_1$;

[29] the apoptosis-inducing agent of [26], wherein the ligand of an NOR-1 receptor is any one of the compounds listed in Tables 14 to 58; and

[30] a NOR-1 gene expression-inducing agent, which comprises a ligand of an eosinophil CD30 receptor.

DETAILED DESCRIPTION OF THE INVENTION

Figure 1:
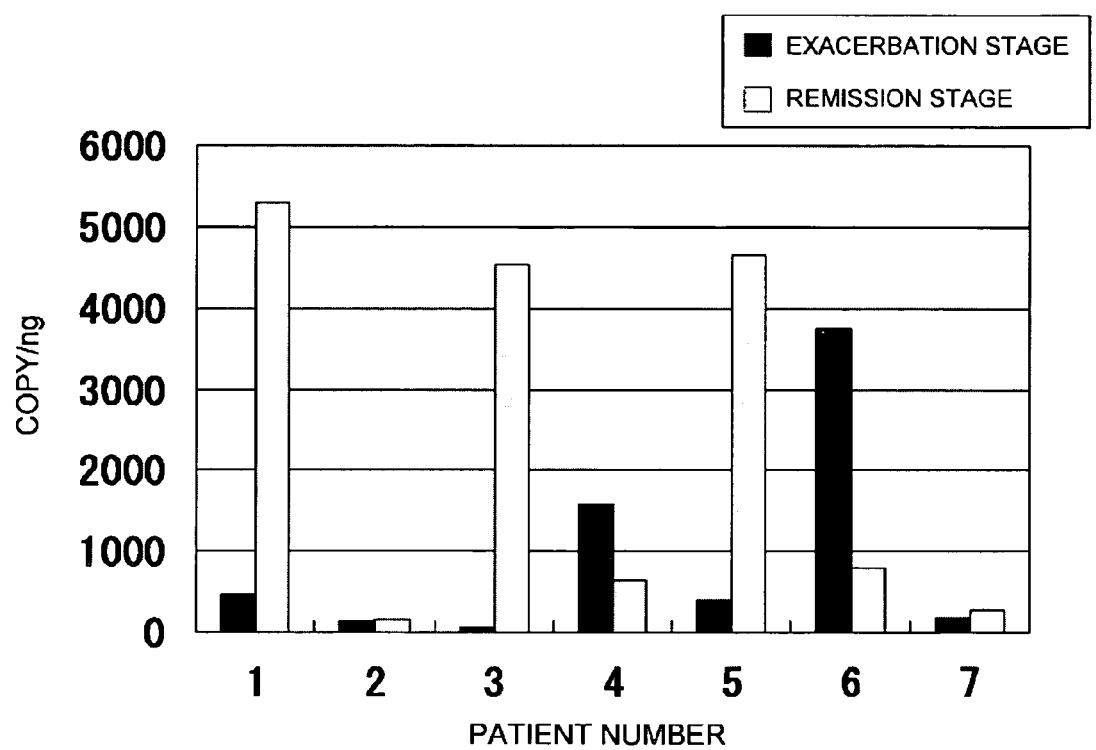
FIG. 1 shows the 2250-01 expression levels (copy/ng RNA) corrected for β-actin, in the exacerbation stage and the remission stage of atopic dermatitis patients (patient numbers 1 to 7).

Through the comparison of the exacerbation stage and remission stage of an atopic dermatitis patient, the present inventors found that the expression level of the NOR-1 (MINOR) gene (in the present specification, it may be simply referred to as "NOR-1") increases in eosinophils of patients in the remission stage associated with the decrease of eosinophils. Therefore, allergic diseases can be tested in subjects using the expression level of the NOR-1 gene as an index.

The present invention provides a method of testing for allergic diseases, which comprises measuring the expression level of the NOR-1 gene.

A preferred embodiment of the method of the present invention comprises the steps of:
(a) measuring the expression level of a gene encoding the NOR-1 receptor protein in eosinophils of a test subject; and
(b) comparing the measured expression level to the expression level of the gene in eosinophil cells of a healthy subject.

NOR-1 (MINOR) receptor is a γ-type receptor of the nuclear orphan receptors that has various names and constitute three subfamilies as shown in Table 1, and is mainly called NOR-1 regardless of the species.

TABLE 1

|   | Human | Mouse | Rat |
|---|---|---|---|
| α | NAK-1 (TR3) | nur77 | NGFI-B |
| β | TINUR/NOT | Nurr1 | RNR-1 |
| γ | MINOR/CHN | TEC | NOR-1 |

Information relating to the amino acid sequences of these NOR-1 (MINOR) receptor proteins or the nucleotide sequences of genes encoding the proteins can be readily obtained from various gene databases known to those skilled in the art. Specifically, the nucleotide sequence of a gene encoding the human NOR-1 receptor protein (NOR-1 gene) is shown in SEQ ID NO: 1, and the amino acid sequence of the NOR-1 receptor protein is shown in SEQ ID NO: 2.

Herein, the general phrase "allergic disease" is refers to diseases involving allergic reactions. More specifically, it is defined as a disease for which an allergen is identified, a strong correlation between the exposure to the allergen and the onset of the pathological change is demonstrated, and the pathological change has been proven to have an immunological mechanism. Herein, an immunological mechanism means that leukocytes show an immune response to allergen stimulation. Examples of allergens include mite antigen and pollen antigen.

Representative allergic diseases include bronchial asthma, allergic rhinitis, atopic dermatitis, pollen allergy and insect allergy. Allergic diathesis is a genetic factor that is inherited from allergic parents to their children. Familial allergic diseases are also called atopic diseases, and their causative factor that is inherited is the atopic diathesis. The term "atopic dermatitis" is a general term for atopic diseases with dermatitis among atopic diseases.

The tests for allergic diseases of the present invention include following tests. A test for determining whether a subject is affected with an allergic disease or not, a test for determining whether a subject has a trait of being easily affected by an allergic disease or not, and a test for assessing whether the allergic symptom is improving or not. The NOR-1 gene of this invention showed increased expression level especially in the eosinophils of atopic dermatitis patients in the remission stage associated with the decrease of eosinophils. Since eosinophils are a representative clinical marker for atopic dermatitis, a clinical marker associated with its decrease is useful for assessing therapeutic effects.

More specifically, increased expression of the NOR-1 gene indicates that the allergic disease is improving with the decrease of eosinophils.

The severity of atopic dermatitis and the number of eosinophils are correlated. In fact, actively decreasing the number of eosinophils may lead to curing the disease. In relation to the measurement of these genes that are specifically induced in eosinophils accompanied with the decrease of its numbers, when methods or substances that actively induce these genes from outside the cell are found, they may lead to novel therapeutic methods for atopic dermatitis and diagnostic methods for evaluating the therapeutic methods.

Herein, the expression level of the NOR-1 gene includes transcription of the gene to mRNA as well as translation into protein. Therefore, a method of testing for an allergic disease according to the present invention is performed by comparing the expression intensity of mRNA corresponding to the gene, or the expression level of protein encoded by the gene.

Measurement of the expression level of the NOR-1 gene in a method of testing for allergic diseases of the present invention may be conducted according to gene analytical methods known to those skilled in the art. More specifically, for example, a hybridization technique with a nucleic acid that hybridizes to the NOR-1 gene as a probe, a gene amplification technique with a DNA hybridizing to the gene of this invention as a primer, or such can be utilized.

A primer or probe that can be used as a reagent for testing for an allergic disease according to the present invention includes: a polynucleotide comprising at least 15 nucleotides that are complementary to the nucleotide sequence of SEQ ID NO: 1 or the complementary strand thereof. Herein, the term "complementary strand" refers to one strand of a double stranded DNA, which is composed of A:T (or A:U for RNA) and G:C base pairs, to the other strand. In addition, "complementary" means not only those completely complementary to a region of at least 15 continuous nucleotides, but also having a homology of at least 70%, preferably at least 80%, more preferably 90%, and even more preferably 95% or higher. The degree of homology between nucleotide sequences can be determined by the algorithm such as BLASTN.

Such polynucleotides are useful as probes to detect and isolate the polynucleotide encoding the protein according to the present invention, or as primers to amplify the polynucleotide according to the present invention. When used as a primer, those polynucleotides have a chain length of usually 15 bp to 100 bp, preferably 15 bp to 35 bp. When used as a probe, DNAs comprising the whole sequence of the polynucleotide according to the present invention, or its partial sequence that contains at least 15-bp, are used. When used as a primer, its 3' region must be complementary to the polynucleotide of the present invention, while the 5' region can be linked to a restriction enzyme-recognition sequence or tag.

The "polynucleotides" of the present invention may be either DNA or RNA. These polynucleotides may be either synthetic (isolated) or naturally occurring. In addition, DNA used as a probe for hybridization is usually labeled. Examples of labeling methods are described below. Herein, the term "oligonucleotide" refers to polynucleotides with relatively low degree of polymerization. Oligonucleotides are included in polynucleotides. The labeling methods are as follows:

nick translation labeling using DNA polymerase I;
end labeling using polynucleotide kinase;
fill-in end labeling using Klenow fragment (Berger, S L, Kimmel, Ark. (1987) Guide to Molecular Cloning Techniques, Method in Enzymology, Academic Press; Hames, B D, Higgins, S J (1985) Genes Probes: A Practical Approach. IRL Press; Sambrook, J, Fritsch, E F, Maniatis, T. (1989) Molecular Cloning: a Laboratory Manual, 2nd Edn. Cold Spring Harbor Laboratory Press);

transcription labeling using RNA polymerase (Melton, D A, Krieg, P A, Rebagkiati, M R, Maniatis, T, Zinn, K, Green, M R. (1984) Nucleic Acid Res., 12, 7035–7056); and non-radioisotopic labeling of DNA by incorporating modified nucleotides (Kricka, L J. (1992) Nonisotopic DNA Probing Techniques.Academic Press).

For testing for allergic diseases using hybridization techniques, for example, Northern hybridization, dot blot hybridization or DNA microarray technique may be used. Furthermore, gene amplification techniques, such as RT-PCR method may be used. By using the PCR amplification monitoring method during the gene amplification step in RT-PCR, one can achieve quantitative analysis for the gene expression of the present invention.

In the PCR gene amplification monitoring method, the detection target (DNA or reverse transcript of RNA) is hybridized to probes that are dual-labeled at both ends with different fluorescent dyes whose fluorescence cancels each other out. As the PCR proceeds and the Taq polymerase degrades the probe due to its 5'-3' exonuclease activity, the two fluorescent dyes become distant from each other and the fluorescence is detected. The fluorescence is detected in real time. By simultaneously measuring a standard sample in which the copy number of the target is known, it is possible to determine the copy number of the target in the subject sample with the cycle number where PCR amplification is linear (Holland, P. M. et al., 1991, Proc. Natl. Acad. Sci. USA 88: 7276–7280; Livak, K. J. et al., 1995, PCR Methods and Applications 4(6): 357–362; Heid, C. A. et al., 1996, Genome Research 6: 986-994; Gibson, E. M. U. et al., 1996, Genome Research 6: 995-1001). For example, for the PCR amplification monitoring method ABI PRISM7700 (PE Biosystems) may be used.

The method of testing for allergic diseases of the present invention can also be carried out by detecting a protein encoded by the NOR-1 gene. For example, test methods such as Western blotting, immunoprecipitation and ELISA using an antibody that binds to a protein encoded by this gene may be employed.

Antibodies that bind to the NOR-1 protein used in the detection may be produced by techniques well known to those skilled in the art. Antibodies used in the present invention may be polyclonal or monoclonal (Milstein, C. et al., 1983, Nature 305 (5934): 537–40). For example, polyclonal antibodies against the protein of the present invention may be produced by collecting blood from mammals sensitized with an antigen, and separating the serum from this blood using known methods. As polyclonal antibodies, serum containing polyclonal antibodies may be used. If needed, a fraction containing polyclonal antibodies can be further isolated from this serum. Alternatively, monoclonal antibodies may be obtained by isolating immune cells from mammals sensitized with an antigen; fusing these cells with myeloma cells, and such; cloning the obtained hybridomas; and collecting the antibodies from the culture as the monoclonal antibody.

To detect the NOR-1 protein, these antibodies may be appropriately labeled. Alternatively, instead of labeling the antibodies, a substance that specifically binds to antibodies, for example, protein A or protein G, may be labeled to indirectly detect the protein. Specifically, one example of indirect detection method is ELISA.

A protein or its partial peptide used as an antigen may be obtained, by inserting the NOR-1 gene or its portion into an expression vector, introducing the vector into an appropriate host cell to produce a transformant, culturing the transformant to express the recombinant protein, and purifying the expressed recombinant protein from the culture or the culture supernatant. Alternatively, oligonucleotides consisting of a partial amino acid sequence of the amino acid encoded by the NOR-1 gene can be chemically synthesized to be used as the immunogen.

In this invention, it is preferred that eosinophils of a test subject are used as the sample. Eosinophils can be prepared by conventional methods from peripheral blood. Specifically, leukocytes are isolated, for example, by fractionating heparinized blood by centrifugation. Next, granulocytes are fractionated, for example, by Ficoll centrifugation of leukocytes, and furthermore eosinophils can be isolated, by depletion of neutrophils using the CD16 antibody. A sample for immunological assays of the aforementioned protein can be obtained by disrupting the isolated eosinophils to produce a lysate. Alternatively, a sample for measuring mRNA corresponding to the aforementioned gene can be obtained by extracting mRNA from this lysate. The use of a commercially available kit is convenient for extracting mRNA or preparing a lysate of eosinophils.

As an embodiment of the present method of testing for allergic diseases, the expression level of the gene that serves as an index may be measured, without isolation of eosinophils, in whole blood or peripheral blood leukocyte population. In this case, by correcting the measured values, the change of gene expression levels in cells can be determined. For example, based on the measured value of the expression level of a gene (housekeeping gene) that is specifically expressed in eosinophils and whose expression level is not widely altered regardless of the cellular conditions, the measured value of the expression level of the gene serving as an index in this invention can be corrected.

Alternatively, in the case where the protein to be detected is a secretory protein, comparison of the expression level of a gene encoding the protein is accomplished by measuring the amount of the target protein contained in body fluid sample, such as blood and serum, in a subject.

When the result of the test for an allergic disease of this invention shows an elevated expression level of the gene of this invention especially in a patient with an allergic disease such as atopic dermatitis, allergic symptoms are presumed to be improving together with the decrease of eosinophils.

Furthermore, this invention relates to an allergic disease animal model, wherein said animal is a transgenic non-human animal showing decreased expression level of the polynucleotide of (a) or (b) in eosinophil cells:
  (a) a polynucleotide encoding an NOR-1 receptor protein; and
  (b) a polynucleotide encoding a protein whose expression in eosinophils increases in association with the decrease of eosinophils in the remission stage of atopic dermatitis, wherein said polynucleotide hybridizes under stringent conditions with a polynucleotide encoding an NOR-1 receptor protein.

According to this invention, a decrease in expression level includes a knockout condition in which the function of the gene has been substantially diminished. Herein, the condition in which the function of the gene has virtually suppressed refers to a condition in which neither expression of the gene nor the activity of the protein encoded by this gene is observed. The expression level of the gene can be confirmed by quantitative PCR such as those shown in Examples. Furthermore, that substantially no activity of the translation product protein is detected can be confirmed by comparison to a normal condition.

Such a transgenic animal includes animals that are incapable of expressing the intact activity of the protein, for example, due to artificial mutation of the amino acid sequence and introduction of a stop codon by introducing a mutation into the coding region of the gene. Examples of mutation in the amino acid sequence are substitution, deletion, insertion and addition of amino acid(s). In addition, by mutagenizing the transcriptional regulatory region of the gene, the expression itself of the gene of this invention can be controlled.

Methods for obtaining transgenic animals with a particular gene as a target are known. That is, a transgenic animal can be obtained by a method where the gene and ovum are mixed and treated with calcium phosphate; a method where the gene is directly introduced into the nucleus of oocyte in the pronuclei using a micropipette under a phase contrast microscope (microinjection method; U.S. Pat. No. 4,873, 191); a method where embryonic stem cells (ES cells) are used; etc. Furthermore, a method has been developed for infecting ovum with a gene-inserted retrovirus vector, a sperm vector method for transducing a gene into ovum via sperm, etc. The sperm vector method is a gene recombination technique for introducing an exogenous gene by fertilizing the ovum with sperm after the exogenous gene has been incorporated into the sperm by adhesion, electroporation, and so on (M. Lavitranoet, et al. Cell, 57, 717, 1989).

Transgenic animals of the present invention can be produced using all the vertebrates except for humans. More specifically, transgenic animals having various transgene and modified gene expression levels are produced using vertebrates such as mice, rats, rabbits, miniature pigs, goats, sheep or cattle.

Examples of transgenic animals of this invention include a knockout animal in which expression of a homologue of the human NOR-1 gene comprising the nucleotide sequence of SEQ ID NO: 1 is inhibited. Observation of the phenotype of the knockout animal specifically tells the function of the gene that was knocked out. The NOR-1 gene comprising the nucleotide sequence of SEQ ID NO: 1 showed increased expression in eosinophils in the remission stage of atopic dermatitis associated with the decrease of eosinophils in humans. Therefore, the animal in which a homologue of this gene is knocked out is useful as an animal model for allergic diseases.

For example, if the knockout animal of this invention develops dermatitis, or indicates change in measured values relating to some sort of allergic diseases, a screening system to search for a compound having the function to allow recovery therefrom can be constructed.

A method of producing a knockout animal is well known. For example, the method of producing a knockout mouse by performing homologous recombination using embryonic stem cells, and selecting the embryonic stem cells in which one of the alleles is modified or destroyed, is known. More specifically, a chimeric animal containing cells derived from an embryonic stem cell and cells derived from an embryo, is obtained, for example, by inserting a genetically manipulated embryonic stem cell into a fertilized egg. When this chimeric animal (chimera refers to a single individual formed from somatic cells derived from two or more fertilized eggs) is crossed with a normal mouse, a heterozygote in which one of the alleles is modified or destroyed in its entirety can be produced. Furthermore, a homozygote can be produced by crossing heterozygotes. The transgenic animals of this invention include both the heterozygote and the homozygote.

Homologous recombination refers to a mechanism of genetic recombination that occurs between two genes having the same or very similar nucleotide sequences. PCR can be used to select cells that have undergone homologous recombination. PCR using a portion of an insert gene and a portion of the region in which insertion is expected as primers, can confirm the occurrence of homologous recombination in cells that produce amplification products. Furthermore, when inducing homologous recombination of a gene expressed in an embryonic stem cell, neomycin resistance gene is linked to a transgene and the gene is introduced into a cell to make the cell neomycin resistant, to thereby easily select the cells. This and other known methods and modified methods thereof can be used for selection of cells.

As shown in the Examples described below, the present inventors succeeded in establishing a transgenic (TG) mouse in which the human NOR-1 gene expression is actually induced by an actin promoter. The TG mouse mentioned above is an example of a preferred embodiment of the transgenic animal of this invention.

In addition to the screening of pharmaceutical agents for the treatment or prevention of allergic diseases described below, the transgenic animals of this invention are useful for elucidating the mechanism of allergic diseases and for testing the safety of screened compounds.

According to the present invention, the expression levels of the NOR-1 gene were revealed to rise in the eosinophils of atopic dermatitis patients in the remission stage associated with the decrease of eosinophils. Therefore, animals in which the expression level of the NOR-1 gene or genes functionally equivalent thereto in eosinophil cells has been artificially lowered can be used as allergic disease model animals. The decrease of expression level in eosinophils includes decrease in the expression level of the genes in the entire population of leukocytes. In other words, this phrase includes the decreased expression level of the aforementioned genes not only in eosinophils but also in the entire population of leukocytes. In the present invention, a functionally equivalent gene normally refers to a gene of either (a) or (b) described above. More specifically, examples of functionally equivalent genes of this invention include genes that hybridize under stringent conditions to a gene that encodes NOR-1. Generally, the following conditions can be indicated as the stringent conditions of this invention. Stringent conditions generally mean hybridization in 4×SSC at 65° C. followed by washing with 0.1×SSC at 65° C. for 1 hour. Temperature conditions for hybridization and washing that greatly influence stringency can be adjusted by the melting temperature (Tm). Tm varies with the ratio of constitutive nucleotides in the hybridizing base pairs and the composition of hybridization solution (concentrations of salts, formamide and sodium dodecyl sulfate). Therefore, considering these conditions, those skilled in the art can select an appropriate condition to achieve an equal stringency from their experience or through experimentation.

For example, the aforementioned transgenic animals may be used as the animal model of this invention.

Furthermore, the present invention provides a method for detecting the influence of a candidate compound on the expression level of the polynucleotide of this invention. According to this invention, the expression level of the NOR-1 gene is significantly increased in eosinophils of atopic dermatitis patients in the remission stage associated with the decrease of eosinophils. Therefore, based on the method for detecting the influence on the expression level of the gene, therapeutic drugs for allergic diseases can be obtained by selecting compounds that increase its expression level. Herein, compounds that increase the expression level of a gene refer to compounds that have the function of inducing any one of the steps selected from gene transcription, translation and expression of protein activity. The present invention further provides a method for detecting the activity of the NOR-1 gene product protein (transcriptional activation ability) in addition to the expression level of the NOR-1 gene. By selecting compounds that increase the activity of the NOR-1 gene product protein (transcriptional activation ability), therapeutic drugs for allergies can be devised.

The method for detecting the influence of a candidate compound on the expression level of the polynucleotide according to this invention can be performed in vivo or in vitro. In order to detect an in vivo influence, an appropriate test animal is used. For example, an animal model for an allergic disease or an animal model for an allergic disease that is a transgenic non-human animal in which the expression of the aforementioned gene (a) or (b) is inhibited in eosinophils can be used as the test animal. Detection of in vivo influence on the expression level based on the present invention can be performed, according to the following steps of:

(1) administering the candidate compound to a test animal; and (2) measuring, in the eosinophil cells of the test animal, the expression level of a polynucleotide of (a) or (b) described above:

For example, transgenic animals in which the expression of the NOR-1 gene has been decreased by expressing an antisense of the NOR-1 gene can be used as a test animal in the method of detection of this invention. Such transgenic animals may be produced as follows: first, an antisense RNA expression vector is constructed by inserting the full-length or partial sequence of the NOR-1 gene downstream of an appropriate promoter sequence in reverse direction. This expression vector is introduced into the nucleus to express the antisense of the NOR-1 gene. Thus, a transgenic animal with decrease NOR-1 gene expression can be obtained. When the expression vector contains a promoter whose transcription may be regulated by an appropriate substance (agent), the expression level of the NOR-1 gene in a transgenic animal can be controlled by administering that substance.

The influence of a candidate compound for a pharmaceutical agent on the expression level of the NOR-1 gene can be detected by administering the candidate compound for a pharmaceutical agent to an animal model in which the expression of the NOR-1 gene is decreased as described above and by monitoring the effect of the compound on the expression of the NOR-1 gene in the eosinophils of the animal model.

The method of screening of this invention allows selection of pharmaceutical agents involved in various ways in the expression of the NOR-1 gene. Specifically, for example, candidate compounds for pharmaceutical agents having any of the following function can be discovered:

activation of a signal transduction pathway that causes expression of the NOR-1 gene;

increase of transcription activity of the NOR-1 gene;

inhibition of degradation or stabilization of the transcription product of the NOR-1 gene; etc.

An in vitro detection can be performed, by a method where a candidate compound is contacted with cells expressing a gene of above-described (a) or (b) to detect the expression level of the gene. More specifically, the method may be carried out according to the following steps of:

(1) contacting a candidate compound with cells that express the polynucleotide of the above-described (a) or (b); and
(2) measuring the expression level of the polynucleotide of the above-described (a) or (b).

In this invention, cells to be used in the step (1) can be obtained by inserting these polynucleotides into an appropriate expression vector and then transfecting suitable host cells with the vector. Any vectors and host cells may be used as long as they are capable of expressing the gene of this invention. Examples of host cells in the host-vector system are *Escherichia coli*, yeast cells, insect cells, animal cells, and available vectors usable for each can be selected.

Vectors maybe transfected into the host by biological, physical or chemical methods. Examples of the biological methods include methods using virus vectors; methods using specific receptors; and the cell-fusion method (HVJ (hemagglutinating virus of Japan; Sendai virus) method, the polyethylene glycol (PEG) method, the electric cell fusion method and microcell fusion method (chromosome transfer)). Examples of the physical methods include microinjection, electroporation and using a gene particle gun. The chemical methods are exemplified by the calcium phosphate precipitation method, the liposome method, the DEAE-dextran method, the protoplast method, the erythrocyte ghost method, the erythrocyte membrane ghost method and the microcapsule method.

In the detection method of this invention, leukocyte cell lines can be used as cells for expressing the polynucleotide of the aforementioned (a) or (b). Examples of leukocyte cell lines are cell lines derived from leukocytes, such as Eol, YY-1, HL-60, TF-1 and AML14.3D10. Among the leukocyte cell lines, cell lines derived from eosinophils are preferred for the detection method of this invention. Examples of cell lines derived from eosinophils include Eol, YY-1 and AML14.3D10.

Eol (Eol-1: Saito H et al., Establishment and characterization of a new human eosinophilic leukemia cell line. Blood 66, 1233–1240, 1985) can be obtained from Hayashibara Research Institute. Similarly, YY-1 (Ogata N et al., The activation of the JAK2/STAT5 pathway is commonly involved in signaling through the human IL-5 receptor. Int. Arch. Allergy Immunol., Suppl 1, 24–27, 1997) is available from The Institute of Cytosignal Research. Furthermore, AML14.3D10 (Baumann MA et al., The AML14 and AML14.3D10 cell lines: a long-overdue model for the study of eosinophils and more. Stem Cells, 16, 16–24, 1998) is commercially available from Paul CC at Research Service, VA Medical Center, Dayton, Ohio, USA.

In addition, by culturing for about 1 week in the presence of butyric acid, HL-60 clone 15 (ATCC CRL-1964), which is an undifferentiated leukocyte cell line, can differentiate into eosinophils to give an eosinophil cell line. Eosinophils can be detected due to their morphological characteristic of being polymorphonuclear and having eosinophilic granules. Morphological observations are performed by Giemsa staining and Difquick staining. Generally, human leukocyte cell line containing eosinophils can be established by cloning immortalized cell sample from a leukemia patient. Therefore, those skilled in the art can obtain eosinophil cell lines by a conventional method when necessary. The method of screening involves addition of a candidate compound with the aforementioned leukocyte cell line. Then, the expression levels of the polynucleotides of (a) or (b) in the leukocyte cell line are measured and a compound that increases the expression level of the gene is selected.

Transformed cells in which the expression of the polynucleotide of aforementioned (a) or (b) is modified can be used as cells for the in vitro detection method. Examples of such transformed cells are cells transformed with an expression vector for an antisense of the polynucleotide. The cell transformed with an antisense expression vector can be obtained according to a principle similar to that for the production of the aforementioned transgenic animal. Using the obtained transformed cell, the influence of the candidate compound on the expression level of the gene can be detected.

In the method of the present invention, the expression levels of polynucleotides of described above (a) or (b) can be compared by detecting the expression levels of not only proteins encoded by these genes but also by the corresponding mRNAs. For the comparison of the expression level using mRNA, the step of preparing mRNA sample as described above is conducted in place of the step of preparing a protein sample. Detection of mRNA and protein can be carried out according to the known methods as described above.

Furthermore, it is possible to obtain the transcriptional regulatory region of the NOR-1 gene and construct a reporter assay system. Reporter assay system means a system of screening for a transcriptional regulatory factor that acts on the transcriptional regulatory region using the expression level of a reporter gene that is located downstream of the transcriptional regulatory region and expressed under the control of the regulatory region as an index.

A transcriptional regulatory region is exemplified by promoter, enhancer, as well as CAAT box and TATA box, which are usually found in the promoter region. Examples of the reporter gene include the chloramphenicol acetyltransferase (CAT) gene, the luciferase gene and growth hormone genes.

A transcriptional regulatory region of the NOR-1 gene can be obtained using conventional methods as follows. Specifically, first, based on the nucleotide sequence described in SEQ ID NO: 1, a human genomic DNA library, such as BAC library and YAC library, is screened by a method using PCR or hybridization to obtain a genomic DNA clone containing the sequence of the cDNA. Based on the sequence of the resulting genomic DNA, the transcriptional regulatory region of the NOR-1 gene is predicted and obtained. The obtained transcriptional regulatory region is cloned to be localized upstream of a reporter gene to prepare a reporter construct. The resulting reporter construct is introduced into a cultured cell strain to prepare a transformant for screening. By contacting a candidate compound with this transformant to detect the expression of a reporter gene, it is possible to assess the effect of the candidate compound on the transcriptional regulatory region.

Based on the method of detecting the influence on the expression level of the polynucleotides of this invention, it is possible to carry out screening for a compound that alters the expression level of the polynucleotides. This invention relates to a method of screening for a compound that alters the expression level of a polynucleotide of above-described (a) or (b), comprising of the following steps.

The present invention provides a method of screening for a compound that increases the expression level of a polynucleotide of above-described (a) or (b), the method comprising the steps of detecting the influence of a candidate compound on the expression level of the polynucleotide in vivo and/or in vitro, and selecting a compound that increases the expression level compared to a control.

Alternatively, this invention relates to a method of screening for a compound that acts on the transcriptional regulatory region by the reporter assay utilizing the transcriptional regulatory region of the NOR-1 gene. Based on the results of reporter assay according to this invention, by selecting a compound that increases the expression level of the reporter gene compared to a control, it is possible to obtain a compound that induces the expression of the NOR-1 gene. Furthermore, the present invention relates to a method of screening for agonists or antagonists that bind to the ligand-binding domain.

The NOR-1 (MINOR) receptor protein discovered by the present inventors as a protein associated with allergic diseases is an orphan receptor and hitherto, none of its native ligand activator has been found. The ligand activator of the NOR-1 protein is considered to directly activate NOR-1 in eosinophils, and promote apoptosis. Therefore, a ligand activator of the NOR-1 receptor is expected to serve as a therapeutic agent for allergic diseases. Generally, a ligand for the receptor can be obtained by searching compounds that bind to the receptor protein.

The present invention provides a method of screening for candidate compounds for therapeutic agents for an allergic disease, which comprises selecting compounds that may bind to the NOR-1 protein. In this method, the NOR-1 receptor protein is contacted with a test compound, then the binding activity between the NOR-1 receptor protein and the test compound is measured, and the compound that binds to the NOR-1 receptor protein is selected. Furthermore, agonists and antagonists can be selected by measuring the binding and by the transcription activity of NOR-1.

The NOR-1 receptor protein of this method includes its partial peptides. The measurement of the binding activity between the NOR-1 receptor protein and a test compound in the method described above can be carried out by using methods known to those skilled in the art.

For example, when the compound that binds to NOR-1 is a protein, West-Western blotting can be performed as the screening method of this invention. Specifically, a cDNA library that uses a phage vector (λgt11, ZAPII, etc.) is constructed from tissues or cells predicted to express a protein (test protein) that binds to the NOR-1 protein, this library is expressed on LB-agarose and expressed proteins are immobilized onto a filter. Then, the NOR-1 protein is purified as a biotin labeled protein or as a fusion protein with the GST protein, and reacted with the abovementioned filter. The binding activity can be evaluated due to the detection of plaques expressing the test protein using streptavidin, anti-GST antibodies.

Furthermore, another embodiment of the method of screening for a candidate compound for a therapeutic agent for an allergic disease of this invention includes the following steps of:
(1) providing cells transfected with (a) a DNA that can express a fusion protein of an NOR-1 receptor protein or its ligand binding domain and a transcription regulatory region binding protein, and (b) a DNA having a structure such that a reporter gene is operably linked downstream of a DNA sequence to which the transcription regulatory region binding protein binds;
(2) contacting the cell with a test compound;
(3) measuring the activity of the reporter gene; and
(4) selecting a compound that changes the activity.

The phrase "operably linked" in the above-mentioned method refers to a condition in which the reporter gene is bound such that it may be expressed when the NOR-1 receptor protein or the ligand binding domain of the protein binds to a ligand of the receptor protein or to a ligand-like compound. Generally, GAL4 protein can be preferably used as the "transcription regulatory region binding protein" in the above-mentioned method. Furthermore, GAL4-binding DNA region can be mentioned as an example of the "DNA sequence to which a transcription regulatory region binding protein binds". Additionally, the screening method of the present invention can be performed by a high throughput method.

In a preferred embodiment of the screening method, screening may be performed using the "two-hybrid system" (for example, "MATCHMAKER Two-Hybrid System", "Mammalian MATCHMAKER Two-Hybrid Assay Kit", "MATCHMAKER One-Hybrid System" (all of which are manufactured by Clontech), "HybriZAP Two-Hybrid Vector System" (Stratagene), and methods reported in the literature (Dalton S, and Treisman R (1992) "Characterization of SAP-1, a protein recruited by serum response factor to the c-fos serum response element." Cell 68, 597–612). More specifically, the method of the present invention may be performed as described below, but it is not to be construed as being limited thereto, and those skilled in the art can appropriately modify the method illustrated below to achieve this invention.

In the two-hybrid system, the NOR-1 protein or its partial peptide is normally fused with the GAL4 DNA binding domain and expressed in yeast cells. Using cells that are predicted to express a protein that binds to the NOR-1 protein or to its partial peptide, a cDNA library is constructed which expresses the protein as a fusion protein fused with VP16 or GAL4 transcriptional activating region. Then, this library is introduced into yeast cells. Finally, cDNAs that stem from the library are isolated from detected positive clones (when a protein that binds to the NOR-1 protein or partial peptides including its ligand binding domain is expressed in yeast cells, a reporter gene is activated due to the binding of the protein and the NOR-1 protein or the partial peptide, and thus a positive clone can be detected). Proteins encoded by the cDNAs can be obtained by expressing the isolated cDNAs following transfection into *E. coli*. Thus, proteins that bind to the NOR-1 protein or its partial peptide and genes encoding the proteins may be prepared. Examples of the reporter genes that can be used in the two-hybrid system include, in addition to the HIS3 gene, the Ade2 gene, the LacZ gene, the CAT gene, the luciferase gene and the Plasminogen activator inhibitor type 1 (PAI-1) gene. However, they are not limited to these examples. Apart from yeast cells, the screening using the two-hybrid method can also be performed using mammalian cells or such.

Figure 3:
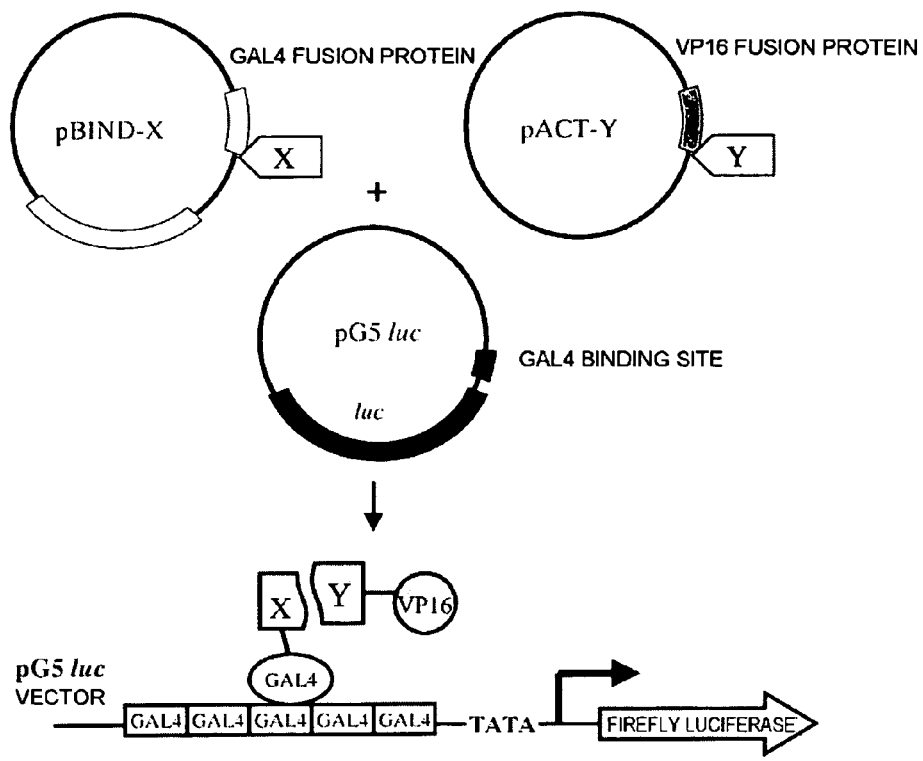
FIG. 3 shows a schematic illustration of a ligand searching system for the NOR-1 receptor constructed by the present inventors. A full-length gene or the ligand-binding site of NOR-1 is inserted into X, and the full-length gene of the retinoic acid X receptor (RXR)α is inserted into Y. These constructs are transfected into NIH3T3 cells, and the activity of induced luciferase is measured.

The present inventors constructed a high throughput system that can screen ligands that increases the transcriptional activating function of the NOR-1 protein by applying a two-hybrid system that uses mammalian cells. This system is an improvement over the conventional mammalian two-hybrid system, and the outline of this system is shown in FIG. 3 (for details, see Examples below).

Figure 4:
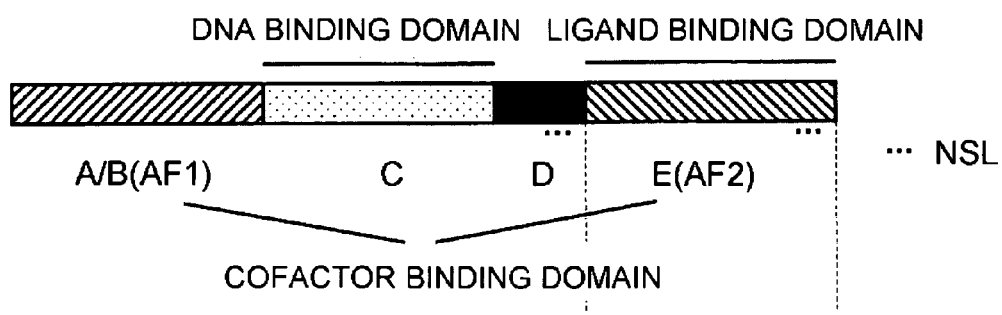
FIG. 4 shows a schematic illustration of the structure of the NOR-1 receptor protein.

Preferably, the screening method of this invention can be performed using the aforementioned high throughput system developed by the present inventors. The present inventors suggested that NOR-1 differs from the other subfamilies (α and β) in that, not only the ligand-binding domain, but also the AF1 region in the vicinity of the N-terminal (FIG. 4) is important for its transcriptional activity. Therefore, in the above-mentioned method, the NOR-1 protein used for forming a fusion protein with GAL4 is preferably a full-length protein and not a protein comprising only the ligand-binding domain.

NOR-1 expression is induced under conditions where leukocytes are hyperactive, as in atopic dermatitis peripheral blood. It is very likely that apoptosis is induced in the cells because of such induction of NOR-1 expression. In vivo ligands may exist in locations where the nuclear receptor is highly expressed. Therefore, the present inventors performed screening according to the above-mentioned method using small molecule lipid-soluble mediators predicted to be produced under such condition as ligand candidate test compounds. Accordingly, the present inventors succeeded in obtaining prostaglandin $A_2$, prostaglandin $A_1$, 16,16-dimethyl prostaglandin $A_2$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $J_2$, 8-iso prostaglandin $A_1$ and such as ligand activators amongst the lipid-soluble mediators. These compounds are prostaglandins having a cyclopentenone structure. This shows that ligand activators that up regulate the transcriptional activating function of NOR-1 (MINOR) can be obtained via the method of this invention.

Screening of compounds that bind to the NOR-1 protein can also be performed using affinity chromatography. For example, the NOR-1 protein is immobilized on an affinity column carrier, and a test sample predicted to express a protein that binds to the NOR-1 protein is applied thereto. Test samples that can be used in this case include, cell extract and cell lysate. After applying the test sample, the column is washed to prepare a protein that was bound to the NOR-1 protein.

Regarding the obtained protein, a DNA encoding the protein can be obtained by analyzing the amino acid sequence of the protein, synthesizing oligo DNAs based on the analyzed sequence, and then screening a cDNA library using the DNA as a probe.

In the present invention, as a means for detecting or measuring bound compound, a biosensor utilizing surface plasmon resonance phenomenon may be used. A biosensor (for example, BIAcore, Pharmacia) utilizing the surface plasmon resonance phenomenon allows real-time observation of the interaction between the NOR-1 protein and a test compound as a surface plasmon resonance signal. Therefore, using biosensors such as BIAcore, the binding between the NOR-1 protein and the test compound can be evaluated.

Isolation of compounds that bind to the NOR-1 protein may be routinely carried out by those skilled in the art. Methods other than those mentioned above include a method for screening molecules that bind to the protein of this invention by acting, on immobilized NOR-1 protein, synthetic compounds, natural products bank or a random phage peptide display library.

A cell used for the method of detecting the influence of a candidate compound on the expression level and transcriptional activation mechanism of the NOR-1 gene according to the present invention, and a polynucleotide or antibody for examining the expression level of the gene can be combined as a detection kit for this method. Candidate compound(s) used as positive or negative control and instructions may be included in the kit. A kit for detecting the influence of a candidate compound on the expression level and transcriptional activation mechanism of the NOR-1 gene based on the present invention may be utilized as a kit for screening compounds that modify the expression level or transcriptional activation mechanism of the NOR-1 gene.

Test candidate compounds that can be used in the screening method of this invention include, without limitation, compound preparations synthesized by chemical methods, such as steroid derivatives; compound preparations synthesized by combinatorial chemistry; mixtures containing multiple compounds such as extracts from animal or plant tissues, or microbial cultures; purified proteins; expression products of gene libraries; and libraries of synthetic peptides. Furthermore, in the method of screening for compounds that bind to the NOR-1 protein of the present invention, without limitation, it is preferable to use small molecule lipid-soluble mediators as the test candidate compounds.

Compounds selected by the screening method of this invention are useful as therapeutic agents for an allergic disease. The expression of the NOR-1 gene increases in eosinophils with the decrease of eosinophils in the remission stage of atopic dermatitis. Therefore, compounds that can increase the expression or function of this gene are expected to have a function to suppress symptoms of atopic dermatitis. Furthermore, compounds selected by the screening method of this invention are expected to serve as therapeutic agents for allergic diseases that have a completely novel functional mechanism involving NOR-1 activation accompanied with eosinophil apoptosis induction. Therefore, the present invention provides a therapeutic agent for an allergic disease containing, as an active ingredient, a compound that can be obtained by the screening method of this invention. The above-mentioned compound includes compounds in which a portion of the structure of the compound that maybe isolated using the screening method of this invention is altered by addition, deletion and/or replacement. As described above, among lipid-soluble mediators, prostaglandins having a cyclopentenone structure were found by the present inventors as compounds that enhance the transcriptional activation ability of NOR-1 (ligand activator of NOR-1). Therefore, examples of therapeutic agents for allergic diseases of this invention preferably include, therapeutic agents for allergic diseases containing, as an active ingredient, a prostaglandin having a cyclopentenone structure that is obtainable by the screening method of this invention. Specific examples of the prostaglandins include, prostaglandin $A_2$, prostaglandin $A_1$, 16,16-dimethyl prostaglandin $A_2$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $J_2$ and 8-iso prostaglandin $A_1$.

Furthermore, substances having ligand activity of the NOR-1 receptor of the present invention appear to induce apoptosis of eosinophils and may have antiallergic effects. Therefore, the present invention provides apoptosis inducing agents containing a ligand of the NOR-1 receptor as an active ingredient, as well as therapeutic agents for allergic diseases containing a ligand of the NOR-1 receptor as an active ingredient. The apoptosis inducing agent of the present invention is preferably an apoptosis inducing agent for eosinophils.

Examples of ligands for the NOR-1 receptor include the above-mentioned prostaglandins having a cyclopentenone structure, and compounds listed in Tables 14 to 58 shown below. In addition, compounds that influence the transcription of NOR-1 include, for example, compounds indicated in the literature (Abayratna Wansa KS, Harris J M, Yan G, Ordentlich P, Muscat G E, "The AF-1 domain of NOR-1/ NR4A3 mediates trans-activation, coactivator recruitment and activation by the purine anti-metabolite 6-Mercaptopurine"; J Biol Chem. 2003 Apr 22 [E-publication ahead of print]).

Moreover, synthetic ligands of NOR-1 (MINOR) can be easily inferred by those skilled in the art from docking studies with the three-dimensional structure of NOR-1, and then are synthesized and developed.

Generally, the term "docking study" refers to searching for compounds and conformations that fit into a ligand-binding domain from a 3-dimensional database comprising several hundred thousand compounds using 3D query pharmacophore model based on the three-dimensional structure of a receptor. The docking study is performed, for example, according to procedures (1) to (4) described below:
(1) constructing a 3D structure of a protein by Modeler (homology model);
(2) searching a binding site by C2. LigandFit;
(3) constructing a pharmacophore query for the binding site by C2 SBF; and
(4) searching in 3D database using the pharmacophore query.

Literature relating to 3D Pharmacophore search includes, Pharmacophore Perception, Development, and Use in Drug Design (Iul Biotechnology Series, 2)-US-ISBN:0963681761 (Hardcover) Guner, Osman F. (Ed.)/Publisher: Intl. Univ. Line Published 1999/12.

Pharmaceutical agents containing such synthetic ligands as an active ingredient are also included in the therapeutic agents for allergic diseases of this invention. Furthermore, by subjecting a synthetic ligand described above to the method of this invention as a test candidate compound, one can evaluate whether the synthetic ligand is a true ligand or not.

Furthermore, based on the first finding that the expression of the NOR-1 receptor of this invention is specifically induced in eosinophils, the present inventors searched for small molecule ligands of the receptor. More specifically, the binding site of the PGA derivative to the NOR-1 ligand-binding region was simulated using the pharmacophore model, and based on the structure activity relationship information on the reporter system of the PGA derivative, compounds other than the PGA derivatives that match the binding pocket were selected from the database. Thus, compounds selected as described above are included as ligands of the NOR-1 receptor of this invention. More specifically, the ligands include compounds shown in Tables 14 to 58. These compounds may be more useful than agonist antibodies against the receptor of this invention.

The present inventors further discovered that eosinophil CD30 ligand stimulation increases the expression of the NOR-1 gene. Thus, the present invention provides an expression-inducing agent for the NOR-1 gene, which includes a ligand of the eosinophil CD30 receptor. The expression inducing agent is expected to serve as a therapeutic agent for an allergic disease that functions by inducing apoptosis of eosinophils via the regulation of the expression of downstream genes of Nor1 in eosinophils.

The therapeutic agents for an allergic disease of this invention can be formulated by mixing an active ingredient with a physiologically acceptable carrier, excipient, diluent or such. The therapeutic agent for an allergic disease of this invention can be administered orally or parenterally with the purpose of improving allergic symptoms.

Oral drugs can take any dosage forms selected from granules, powder, tablets, capsules, solution, emulsion, suspension and so on. Examples of parenteral agents include injections, suppositories and ointments. Injections may include subcutaneous injection, intramuscular injection and intraperitoneal injection.

The dosage of the therapeutic agent for an allergic disease according to the invention may vary depending upon the age, sex, body weight and symptoms of a patient; treatment effects; method for administration; treatment duration; type of active ingredient contained in the pharmaceutical composition etc. Generally, it can be administered in the range of 0.1 mg to 500 mg, preferably 0.5 mg to 20 mg per dose for an adult. However, since the dose varies according to the specific condition, an amount less than the above-described dosage may be sufficient in certain cases and a dosage exceeding the above-described range may be required in others.

Furthermore, the present inventors discovered that apoptosis of cells is induced due to the rise in the expression of the NOR-1 receptor protein. Therefore, apoptosis can be induced by activating the NOR-1 protein in cells. Thus, the present invention provides a method of inducing apoptosis of cells, which comprises activation of the NOR-1 receptor protein in these cells. The method mentioned above also includes a method wherein the induction of apoptosis of cells is conducted through the activation of the expression of the NOR-1 gene.

In a preferred embodiment of the present method, apoptosis is induced by contacting cells with a compound or a prostaglandin having a cyclopentenone structure that can be obtained by the screening method of this invention. The cells in the method of this invention are preferably eosinophils. The number of peripheral blood eosinophils is known to decrease in the remission stage during the treatment of atopic dermatitis. Therefore, an allergic disease may be treated by specifically leading eosinophils to cell death utilizing the method of the present invention. Thus, the present method is useful in treating an allergic disease.

Furthermore, since compounds or prostaglandins having a cyclopentenone structure that can be obtained by the screening method of this invention are considered to have a function to induce apoptosis, the present invention also provides apoptosis inducing agents that include these compounds.

The present invention provides a gene whose expression differs in eosinophils between the exacerbation stage and the remission stage of atopic dermatitis patients. The use of the expression of the gene of this invention as an index enables testing for an allergic disease and screening for a candidate compound for a therapeutic agent.

The expression level of the allergic disease-associated gene of the present invention can be conveniently determined, regardless of the types of allergens. Therefore, comprehensive pathological conditions of allergic reactions can be understood.

In addition, according to the method of testing for allergic diseases of the present invention, the expression level of the gene can be analyzed using peripheral blood eosinophils as a specimen. Therefore, the method of testing for allergic diseases of the present invention is less invasive towards patients. Year after year, high throughput methods and cost effective methods are being developed in gene analysis technology. Therefore, it is expected that in the near future the method of testing for allergic diseases of the present invention will become an important bedside diagnostic tool. Accordingly, the method of the present invention is highly valuable in diagnosis.

Furthermore, the screening method of the present invention is carried out using, as an index, a genetic function closely associated with the increase and decrease of eosinophils that is a representative diagnostic marker for atopic dermatitis. Therefore, compounds that can be found by this screening method are expected to be useful for pathological regulation of a wide variety of allergies.

Moreover, the therapeutic agents for an allergic disease provided by the present invention are useful as pharmaceutical agents having a completely novel functional mechanism, which involves activation of NOR-1 accompanied with the induction of apoptosis of eosinophils.

Hereinafter the present invention is specifically illustrated below with reference to Examples, but is not to be construed as being limited thereto.

EXAMPLE 1

Differential Display Analysis

Screening was performed in order to find novel therapy related genes or genes useful for diagnosis, whose expression in hemocytes isolated from the peripheral blood of an atopic dermatitis patient in the exacerbation stage differs from that of remission due to drug therapy, etc.

(1) Test Subject

Table 1 shows the profiles of seven atopic dermatitis patients whose blood samples were drawn. Allergen non-specific (Total IgE), mite-specific and cedar-specific IgEs were measured by the EIA method. More specifically, the test sera were allowed to react to anti-human IgE antibody-bound cap to bind thereto allergen non-specific IgE antibody or mite- or cedar-specific IgE antibodies in the sera. Next, β-D-galactosidase-labeled anti-human IgE antibody and a substrate solution (4-methylumbelliferyl-β-D-galactopyranoside) were added and allowed to react to produce a fluorescent substance. The reaction was quenched by adding a quenching solution, and the antibody concentration was determined from the fluorescence intensity of a simultaneously measured standard IgE. L-lactate dehydrogenase (LDH) was measured by the UV method (Wroblewski-La Due method) based on the rate of decrease of NADH caused by the reaction of pyruvic acid with NADH is calculated from decrease in absorbance. L-type Wako LDH (Wako Pure Chemicals) and 7170-type automatic analyzer (Hitachi) were used for measuring the LDH values. The number of eosinophils was measured by microscopic examination and automatic hemocyte analyzer SE-9000 (RF/DC impedance system, Sysmex) using 2 ml of EDTA-added blood as the sample.

TABLE 2

| | Patient number | | | | | | | |
|---|---|---|---|---|---|---|---|---|
| | 1 | | 2 | | 3 | | 4 | |
| Donor ID | PA00002 | | PA00068 | | PA00069 | | PA00070 | |
| Condition | Exacerbation stage | Remission stage | Exacerbation stage | Remission stage | Exacerbation stage | Remission stage | Exacerbation stage | Remission stage |
| T-IgE | 6100 | 7100 | 2600 | 2100 | 13000 | 20000 | 15000 | 15000 |
| Mite | 82.1 | 73.8 | 66.4 | >100 | 72.2 | 66.7 | 85.9 | 90.9 |
| Cedar | 57.1 | 77.2 | 14.4 | 19.7 | 15.2 | 22.5 | 61.9 | 59.6 |
| LDH | 910 | 475 | 293 | 296 | 398 | 250 | 173 | 182 |
| Eosinophil (%) | 16 | 11.7 | 23.2 | 10.1 | 16 | 6.2 | 8.6 | 12.1 |
| Eosinophil (/mm³) | 1620 | 611 | 1420 | 468 | 2070 | 527 | 738 | 752 |
| Internal use | ALDECIN inhalant, Theodur INTAL inhalant, ZADITEN | | ZADITEN | | | | ZADITEN, Shofusan ATARAX P | |
| External use | Body: Zalucs Face: LOOOID | | Body: LOOOID Face: nonsteroid | | Body: Zalucs Face: nonsteroid | | Body: LOOOID Face: nonsteroid | |
| Other diseases | Asthma (moderate) | | | | | | | |

| | Patient number | | |
|---|---|---|---|
| | 5 | 6 | 7 |
| Donor ID | PA00071 | PA00073 | PA00164 |
| | Exacerbation Remission | Exacerbation Remission | Exacerbation Remission |
| Condition | stage stage | stage stage | stage stage |
| T-IgE | 9300 9200 | 17000 8800 | 2100 1600 |
| Mite | 74.6 70.8 | 88 >100 | >100 82.8 |
| Cedar | 64.2 71.1 | 18.3 9.27 | 6.51 3.61 |
| LDH | 534 297 | 620 598 | 343 393 |
| Eosinophil (%) | 28.2 13.4 | 13.4 12.3 | 12.9 10.6 |
| Eosinophil (/mm³) | 1830 972 | 945 846 | 898 847 |
| Internal use | CELTECT INTAL oral preparation | ZADITEN DS    INTAL→none | PREDONINE (only 181) Theolong, ALDECIN |
| External use | Body: LOOOID Face: nonsteroid | Body: Zalucs→RINDERON V Face: LOOOID | Body: Zalucs Face: LOOOID |
| Other diseases | Asthma (moderate) | | Asthma (severe/mild) |

(2) Differential Display Analysis

A 3% dextran solution was added to whole blood drawn from a patient, and this was left to stand at room temperature for 30 minutes to precipitate erythrocytes. The upper layer leukocyte fraction was collected, layered on top of Ficoll solution (Ficoll-Paque PLUS; Amersham Pharmacia Biotech), and centrifuged at 1500 rpm for 30 minutes at room temperature. The granulocyte fraction that collected in the lower layer was reacted with CD16 antibody magnetic beads at 4° C. for 30 minutes, and cells that had eluted without being trapped in the separation using Magnetic cell sorting (MACS) were used in the experiment as eosinophils.

Eosinophils prepared as described above were added to Isogen (Nippon Gene; Wako Pure Chemicals). From this resulting solution, RNA was separated according to the protocol attached to Isogen. Chloroform was added, the mixture was stirred and centrifuged, and the aqueous layer was collected. Next, isopropanol was added, the mixture was stirred and centrifuged and the precipitated total RNA was collected. DNase (Nippon Gene; Wako Pure Chemicals) was added to the collected total RNA, the mixture was reacted at 37° C. for 15 minutes, and RNA was collected by phenol-chloroform extraction followed by ethanol precipitation.

Fluorescent Differential Display (abbreviated to DD) analysis using the total RNA thus prepared was carried out according to the literature (T. Ito et al., 1994, FEBS Lett. 351: 231–236). The total RNA was reverse transcribed to obtain cDNA. In the first DD-PCR, 0.2 µg each of the total RNA was used for three types of anchor primers to synthesize cDNAs. In the second DD-PCR, 0.4 µg each of the total RNA was used for the synthesis of cDNAs using three types of anchor primers. In both cases, the cDNAs were diluted to a final concentration equivalent to 0.4 ng/µl RNA and used for further experiments. The DD-PCR was carried out using an amount of cDNA equivalent to 1 ng RNA per reaction. The reaction mixture composition is shown in Table 3.

TABLE 3

| | |
|---|---|
| cDNA (equivalent to 0.4 ng/µl RNA) | 2.5 µl |
| Arbitrary primer (2 µM) | 2.5 µl |
| 10x AmpliTaq PCR buffer | 1.0 µl |
| 2.5 mM dNTP | 0.8 µl |
| 50 µM anchor primer (GT15A, GT15C, or GT15G) | 0.1 µl |
| Gene Taq (5 U/µl) | 0.05 µl |
| AmpliTaq (5 U/µl) | 0.05 µl |
| dH$_2$O | 3.0 µl |
| Total volume | 10.0 µl |

The PCR was carried out as follows: 1 cycle of "95° C. for 3 min, 40° C. for 5 min and 72° C. for 5 min"; subsequently 30 cycles of "94° C. for 15 sec, 40° C. for 2 min and 72° C. for 1 min"; after these cycles, 72° C. for 5 min; and then continuously at 4° C.

Reactions were conducted using 287 primer pairs: i.e., anchor primers GT15A (SEQ ID NO: 3), GT15C (SEQ ID NO: 4) and GT15G (SEQ ID NO: 5) were used in combination with arbitrary primers AG 1 to AG 110, AG 111 to AG 199 and AG 200 to AG 287, respectively. As for the arbitrary primers, oligomers having 10 nucleotides with a GC content of 50% were designed and synthesized.

For gel electrophoresis, a 6% denaturing polyacrylamide gel was prepared, and 2.5 µl sample from the PCR was applied and electrophoresed under 40 W for 210 min. After electrophoresis, the gel was scanned via a Hitachi fluorescence imaging analyzer FMBIO II, wherein the image of the gel was obtained by detecting fluorescence.

Samples from both the exacerbation stage and the remission stage were phoresed simultaneously. Gene bands shifted in the same direction in most patients, showing altered expressions, were visually determined, excised, and subjected to TA cloning and sequence determination. As a result, a DNA sequence (DD analysis band ID 2250-01; hereinafter this gene is referred to as "2250-01") whose expression is significantly enhanced in the remission stage than in the exacerbation stage was found. The primer set used for amplifying band ID 2250-01 is shown below.

Band ID: 2250-01

Length of fragment: 421 bp (excluding the nucleotide sequence of the primer)

Anchor primer: GT15C

Name of arbitrary primer: AG00164

Sequence of arbitrary primer: CATTCTCAGG (SEQ ID NO: 6)

(3) Expression Analysis

In order to confirm the expression level of the 2250-01 gene quantitatively, quantitative PCR was further performed by ABI 7700 using the same clinical sample. Primers and TaqMan probe used for measurement by ABI 7700 were designed using Primer Express (PE Biosystems) from the sequence information obtained by the differential display method. The 5'-end and the 3'-end of TaqMan probe were labeled with FAM (6-carboxy-fluorescein) and TAMRA (6-carboxy-N,N,N',N'-tetramethylrhodamine), respectively.

2250-01 forward primer:

TGCCTTGTCTAGAACTGCACAG     (SEQ ID NO: 7)

2250-01 reverse primer:

AAGTGTGTTGGACCAAGCAGC      (SEQ ID NO: 8)

2250-01 TaqMan probe:

AAGTCAGTGCAGAGCCTGGATGAGGA (SEQ ID NO: 9)

cDNA was used as a template that was prepared by reverse transcription from the total RNA using poly-T (12 to 18 mer) as primers. In order to make a standard curve for the calculation of copy numbers, a plasmid clone containing the nucleotide sequence amplified using both primers was prepared, and serial dilutions thereof were utilized as the template for the reaction. The reaction mixture composition for monitoring PCR amplification is shown in Table 4.

TABLE 4

| Reaction mixture composition for ABI-PRISM 7700 (amount per well) | |
|---|---|
| Sterile distilled water | 25.66(µl) |
| 10x TaqMan buffer A | 5 |
| 25 mM MgCl$_2$ | 7 |
| dATP (10 mM) | 1.2 |
| dCTP (10 mM) | 1.2 |
| dGTP (10 mM) | 1.2 |
| dUTP (10 mM) | 1.2 |
| Forward Primer (100 µM) | 0.15 |
| Reverse Primer (100 µM) | 0.15 |
| TaqMan Probe (6.7 µM) | 1.49 |

TABLE 4-continued

Reaction mixture composition for ABI-PRISM 7700 (amount per well)

| | |
|---|---|
| AmpliTaq Gold (5 U/μl) | 0.25 |
| AmpErase UNG (1 U/μl) | 0.5 |
| Template solution | 5 |
| Total volume | 50 |

In order to correct the difference in the cDNA concentrations among the samples, the same quantitative analysis was carried out for the β-actin gene that was used as internal standard, and, by performing correction based on its copy number, the copy number of the target gene was calculated. For the quantification of the β-actin gene, the human cDNA was used as a template.

As the primers and probe for the measurement of β-actin were used those attached to TaqMan β-actin Control Reagents (PE Biosystems) Their nucleotide sequences are shown below. The "2250-01" expression levels (copy/ng RNA) corrected for that of β-actin are shown in Table β-Actin forward primer:

TCA CCC ACA CTG TGC CCA TCT ACG A   (SEQ ID NO: 10)

β-Actin reverse primer:

CAG CGG AAC CGC TCA TTG CCA ATG G   (SEQ ID NO: 11)

β-actin TaqMan probe:

5'-(FAM)ATGCCC-T(TAMRA)-           (SEQ ID NO: 12)
CCCCCATGCCATCCTGCGTp-3'

FAM: 6-carboxy-fluorescein:
TAMRA: 6-carboxy-N,N,N',N'-tetramethylrhodamine

TABLE 5

2250-01 gene expression level (copy/ng RNA)

| Patient No. | Exacerbation stage | Remission stage |
|---|---|---|
| 1 | 454.19 | 5298.42 |
| 2 | 137.06 | 167.13 |
| 3 | 53.86 | 4543.94 |
| 4 | 1577.46 | 642.43 |
| 5 | 403.84 | 4655.96 |
| 6 | 3745.25 | 801.14 |
| 7 | 173.98 | 286.83 |

(4) Statistical Analysis

Using the above-mentioned data, parametric multiple comparison test and non-parametric multiple comparison test were carried out. Four out of seven above-mentioned atopic dermatitis patients (patient numbers 1, 2, 3 and 5) showed remarkable decrease in the number of eosinophils associated with the transition to the remission stage due to therapy. The number of eosinophils in the blood is a useful clinical index for atopic dermatitis. Therefore, the four patient samples in which the number of eosinophils showed remarkable decrease with the transition to the remission stage (patient numbers 1, 2, 3 and 5) (n=4) were further statistically analyzed. The statistical analyses were carried out using SAS Pre-clinical Package of The SAS SYSTEM, Version 4.0 (SAS Institute Inc.). The results are shown in Table 6.

TABLE 6

2250-01 expression level (copy/ng RNA)

| Paired test between two groups | | Paired-t-test between two |
|---|---|---|
| t-test Parametric | Wilcoxon test Non-parametric | eosinophil-decreasing groups (n = 4) |
| E < R p = 0.274 | E < R p = 0.2969 | E < R p = 0.0572 |

As a result, remarkable increase in the expression of 2250-01 was observed in three out of the seven atopic dermatitis patients mentioned above (patient numbers 1, 3 and 5). These three patients were found amongst the four patients (see Table 2) whose number of eosinophils remarkably decreased with the transition to the remission stage due to therapy. The number of eosinophils in the blood is a useful clinical index for atopic dermatitis. Therefore, the changes in the expression level of 2250-01 in the 4 patient samples in which the number of eosinophils showed a remarkable decrease with the transition to the remission stage (patient numbers 1, 2, 3 and 5) (n=4) was statistically analyzed. The statistical analyses were carried out using SAS Pre-clinical Package of The SAS SYSTEM, Version 4.0 (SAS Institute Inc.).

The results confirmed significant increase in the expression in the remission stage compared to that in the exacerbation stage (p=0.0572). On the other hand, a remarkable decrease in the expression was observed in patients who did not show a decrease in eosinophil counts (patient numbers 4 and 6). These findings indicate that the expression of 2250-01 increases in association with the decrease in the number of eosinophils in the remission stage of atopic dermatitis.

EXAMPLE 2

Expression of 2250-01 in Various Blood Cells

The expression of 2250-01 was examined in cells separated from peripheral blood collected from five normal healthy subjects. Separation of eosinophils (E) was carried out as described above. After the elution of eosinophils, neutrophils (N) were prepared by releasing the cells, which were trapped with CD16 antibody magnetic beads, from the magnetic field, eluting, and recovering. On the other hand, the monocyte fraction recovered in the middle layer by the Ficoll-centrifugation was separated into the fraction eluted from MACS CD3 antibody magnetic beads (mixture of M (monocyte) and B cell) and fraction trapped therein (T-cell fraction). Then, using MACS CD14 antibody magnetic beads, the eluted fraction was separated into the eluted fraction (B cell fraction) and trapped fraction (monocyte fraction), and these three fractions were referred to as purified T cells, B cells and monocytes.

Eosinophils were solubilized using Isogen, while neutrophils, T cells, B cells and monocytes were solubilized with RNeasy (Qiagen), and total RNA were extracted, treated with DNase (by the same methods as described above), and subjected to the gene expression analysis. Primers, probes and others used were the same as above. Average expression levels (AVERAGE: copy/ng (corrected value)) in these blood cells are shown below.

eosinophil (E): 960
neutrophil (N): 73 basophil (B): 36
T-cell (T): 11
monocyte (M): 103

This result indicates that 2250-01 is specifically expressed in eosinophils.

EXAMPLE 3

Extension of Nucleotide Sequence

Nucleotide sequence analysis was performed on 2250-01 by the 5' Rapid Amplification of cDNA Ends (5'RACE) method based on the nucleotide sequence determined in Example 1. Furthermore, cloning was performed by plaque hybridization using phage cDNA library prepared from peripheral blood eosinophil RNAs by SMART cDNA Library Construction kit (CLONTECH). Amplification was performed using primers 2250-01F and 2250-01R, which were designed within the sequence of 2250-01, and a plasmid including the sequence of 2250-01 as a template. The resulting 259-bp PCR product was purified and then used as a probe. As a result, a clone carrying an approximately 2-kb insert including the sequence of 2250-01 was obtained. The determined 2087-bp nucleotide sequence is shown in SEQ ID NO: 15. According to a genome database analysis, this sequence was found to correspond to the intronic region of a nuclear orphan receptor called NOR-1 (MINOR).

Primer sequences:

2250-01F: GTTCCAGGCAATAACATCATACC (SEQ ID NO: 13)
2250-01R: GCTACTTGTGAAACTCCCAAATG (SEQ ID NO: 14)

EXAMPLE 4

Expression Analysis of the NOR-1 Gene

Expression measurement by ABI7700 was performed for the reported exon sequence of NOR-1 (MINOR). The primers and probe used for the TaqMan method were as follows:

Primer 1 (5'):   TGGGTGCCCTGGTAGAACT;      (SEQ ID NO: 16)
Primer 2 (3'):   GCTTCAGGTAGAAGATGCGCT;    (SEQ ID NO: 17)
and
TaqMan probe:    AGGAAGATCTGCACCCTGGGCCTC. (SEQ ID NO: 18)

Figure 2:
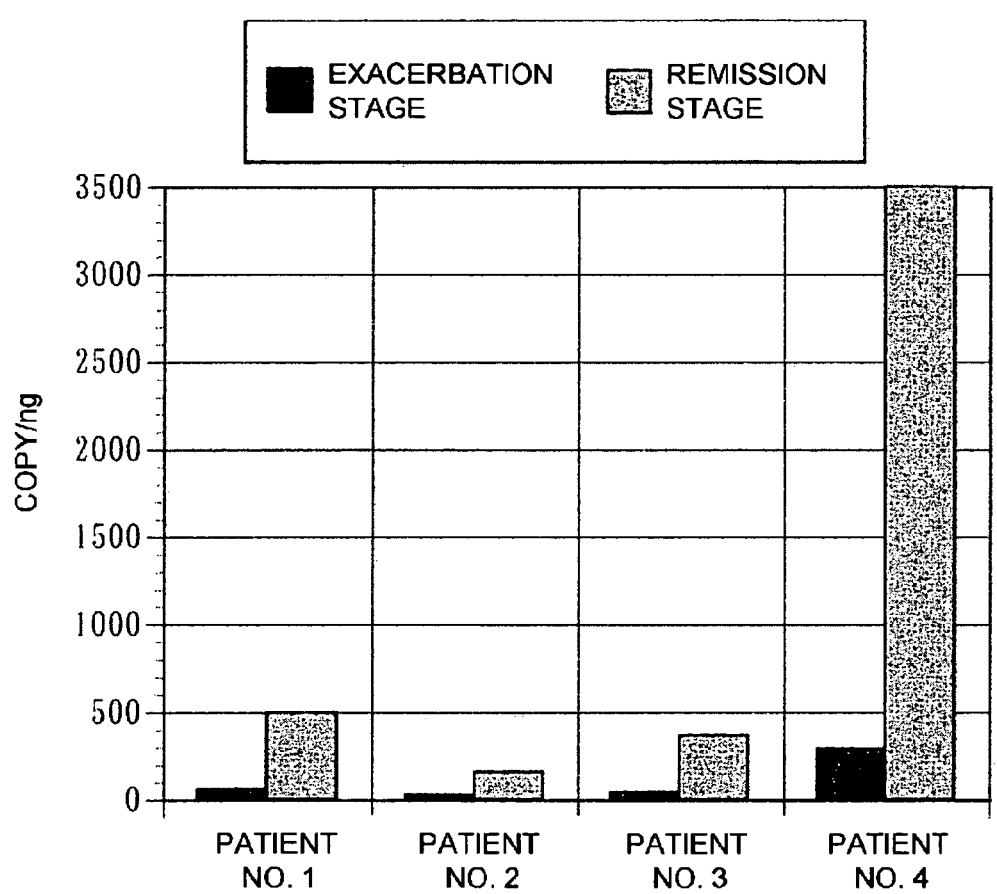
FIG. 2 shows the expression levels of NOR-1 gene determined using the open reading frame (ORF) site of the NOR-1 gene, only in patients whose number of eosinophils decreased with the transition from the exacerbation stage to the remission stage.

Similarly, to the measured result obtained using the intronic region, the tendency that the expression of the NOR-1 gene is induced in the remission stage of patients who showed notable effect against treatment with a decrease of eosinophils was reproduced (FIG. 2).

Enhancement of such gene that indicates apoptotic character in peripheral blood eosinophils during the remission stage due to therapy of atopic dermatitis, corresponds well to the decrease in the number of peripheral blood eosinophils. Thus, the expression induction of this gene seem to correlate well with therapeutic effects.

EXAMPLE 5

Search of NOR-1 Receptor Ligands

Promotion of a pathway that specifically leads eosinophils to cell death through the enhancement of the function of NOR-1 (MINOR), very likely leads to therapy of not only asthma, but also various allergic diseases including atopic dermatitis, which was investigated by the present inventors. NOR-1 (MINOR) is structurally a nuclear receptor; however, it is an orphan receptor and its native ligands and activators are so far unknown. When ligands and activators are found for NOR-1 (MINOR), it can be directly activated in eosinophil cells to promote apoptosis. Therefore, ligand activators of NOR-1 are considered very likely to serve as antiallergic agents, and thus a high throughput system for ligand screening was constructed.

Mammalian Two Hybrid system was slightly modified. Specifically, as illustrated in FIG. 3, the ligand binding domain sequence or the full-length gene of NOR-1(MINOR) was inserted into pBIND (FIG. 4) to express a protein wherein NOR-1 is fused in-frame with the DNA binding domain of GAL4. Different from other subfamilies ($\alpha$ and $\beta$), the AF1 region close to the N-terminus had been inferred to be important for the transcriptional activation of NOR-1 (MINOR), and the insertion of not only the ligand binding domain but the full-length gene was found to be necessary in the Mammalian Hybrid system. Actually, activity could not be detected for lipid-soluble metabolites existing on the metabolic map of mammals that might be natural ligands of NOR-1 in a screening system wherein only the ligand-binding domain was inserted. A plasmid wherein the full-length gene of NOR-1 (MINOR) had been inserted into pBIND and a luciferase reporter plasmid containing a GAL4 binding site were cotransfected into NIH3T3 cells, and the luciferase activity was measured automatically. By further addition of small molecule substances to this system enables screening of ligands by their transcription enhancing activity.

Figure 5:
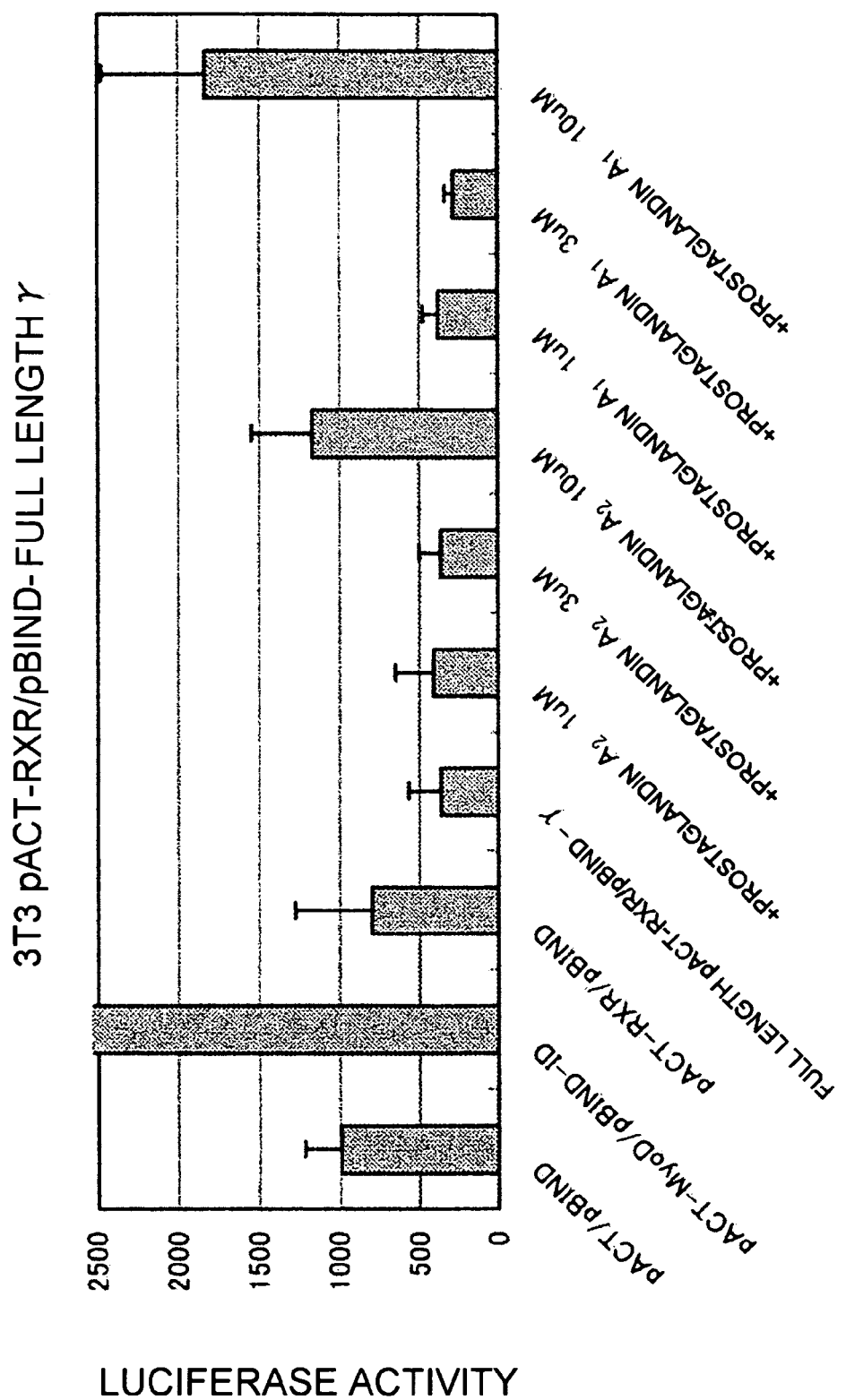
FIG. 5 shows the NOR-1 transcriptional activating function of prostaglandin $A_2$ and prostaglandin $A_1$ used in the system of FIG. 3.

NOR-1 (MINOR) expression is induced under conditions where the leukocytes are hyperactive, such as in atopic dermatitis peripheral blood, and apoptosis of cells is very likely to occur as a result of this induced NOR-1 (MINOR) expression. Ligands existing in vivo may exist at sites where nuclear receptors are highly expressed. Therefore, small-molecule lipid-soluble mediators that are expected to be produced under such conditions were added to the assay system as candidate ligands to evaluate their luciferase activity enhancing function. Among the lipid-soluble mediators, prostaglandins having a cyclopentenone structure, such as prostaglandin $A_2$, prostaglandin $A_1$, 15(R)-15-methyl prostaglandin $A_2$, 16-phenoxy tetranor prostaglandin $A_2$ and 17-phenyl trinor prostaglandin $A_2$, were found to have the function of enhancing the transcriptional activation ability of NOR-1 (MINOR) (FIG. 5, Tables 7 to 13). Thus, the method established by the present inventors opened a way to discover native ligands and synthetic ligands of NOR-1 (MINOR) by high throughput. In addition, compounds such as prostaglandin $A_2$ and prostaglandin $A_1$, and metabolites related thereto were revealed to be very likely the true native ligands of NOR-1 (MINOR).

TABLE 7

| Name of compound | Structural formula | Nor1 LBD-ligand activity | | Full length Nor1-ligand activity | |
|---|---|---|---|---|---|
| | | RXR(+) | RXR(−) | RXR(+) | RXR(−) |
| Prostaglandin $A_2$ | | x | x | ○ 10 μM | ○ 10 μM |
| Prostaglandin $A_1$ | | x | x | ○ 10 μM | ○ 10 μM |

TABLE 8

| | | | | | |
|---|---|---|---|---|---|
| 16,16-dimethyl Prostaglandin $A_2$ | | x | x | ○ 5 μM | ○ 5 μM |
| Prostaglandin $A_3$ | | x | x | x | x |
| Prostaglandin $A_1$ ethyl ester | | x | x | x | x |

TABLE 9

| Name | Structure | | | | |
|---|---|---|---|---|---|
| 15-epi Prostaglandin A$_1$ | 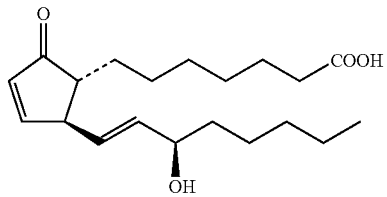 | x | x | x | x |
| 16,16-dimethyl Prostaglandin A$_1$ | 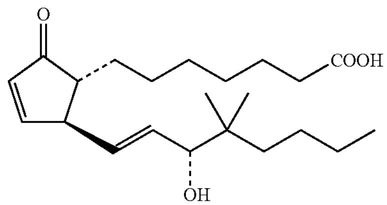 | x | x | x | x |
| 13,14-dihydro-15-keto Prostaglandin A$_2$ | 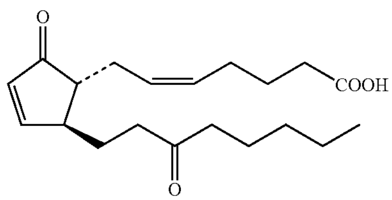 | x | x | x | x |

TABLE 10

| Name | Structure | | | | |
|---|---|---|---|---|---|
| 15(R)-15-methyl Prostaglandin A$_2$ | 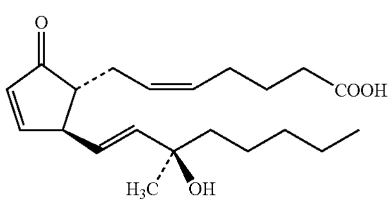 | x | x | ○ 10 μM | ○ 10 μM |
| 15-deoxy-Δ$^{12,14}$-Prostaglandin A$_2$ | | x | x | x | x |
| 16-phenoxy tetranor Prostaglandin A$_2$ | 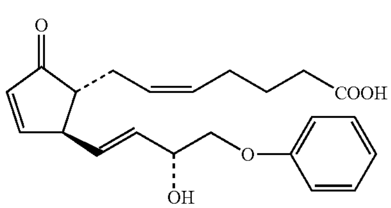 | x | x | ○ 30 μM | ○ 30 μM |

TABLE 11
| | | | | | |
|---|---|---|---|---|---|
| 17-phenyl trinor Prostaglandin A$_2$ | 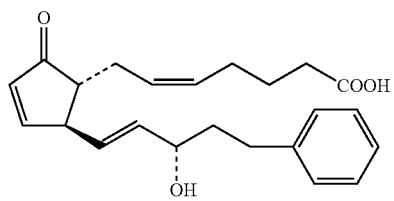 | x | x | o 10 μM | o 10 μM |
| 17-phenyl trinor-13,14-dihydro Prostaglandin A$_2$ | 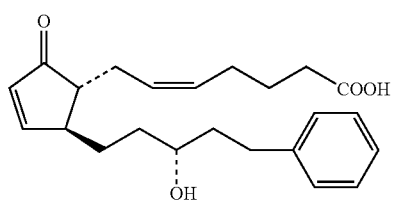 | x | x | x | x |
| 19(R)-hydroxy Prostaglandin A$_2$ | 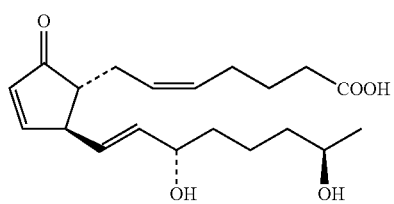 | x | x | x | x |
TABLE 12
| | | | | | |
|---|---|---|---|---|---|
| 15-deoxy-Δ$^{12,14}$-Prostaglandin A$_1$ | 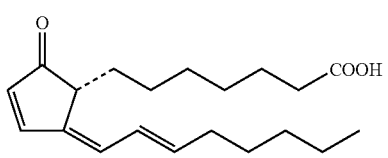 | x | x | x | x |
| Prostaglandin J$_2$ | 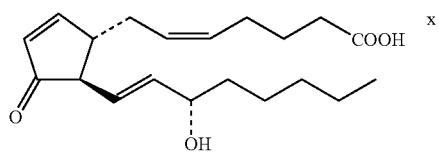 | x | x | x | x |
| 15-deoxy-Δ$^{12,14}$-Prostaglandin J$_2$ | 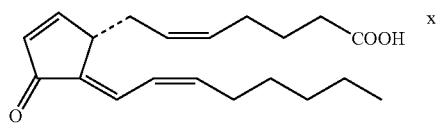 | x | x | o 10 μM | x |

TABLE 13

| Compound | Structure | | | | |
|---|---|---|---|---|---|
| Δ 12-Prostaglandin J$_2$ | [structure] | x | x | x | x |
| 9,10-dihydro-15-de-oxy-Δ$^{12,14}$-Prostaglandin J$_2$ (CAY10410) | [structure] | x | x | x | x |
| 8-iso Prostaglandin A$_1$ | [structure] | ND | ND | ○ 10 μM | ND |

In the Tables above, ND denotes not determined.

EXAMPLE 6

Virtual Compounds

Figure 6:
FIG. 6 shows the structure of 15 (R)-15-methyl-prostaglandin $A_2$ in a gamma model wherein the binding position of the PGA derivative to the NOR-1 ligand-binding domain is simulated using the pharmacophore model.

The binding position of the PGA derivatives to the Nor1 ligand binding domain was simulated by the pharmacophore model (FIG. 6), and based on the information on structure activity relationship in the reporter system of the PGA derivatives, compounds other than the PGA derivatives that fit similarly into the binding pocket were selected from the Catalyst database (screened from BioByte Master File 2001 39,383 compounds, 2,198,646 conformations). The list (including the structural formula) of 155 compounds selected as strongly binding compounds by the simulation are shown in Tables 14 to 49, and the list of 281 compounds selected subsequently are shown in Tables 50 to 58.

TABLE 14

Name of compound

[structure]

135TRIAZINE2DIFLUOROMETHIO4AMYLAMINO6ETHYLAMINO

TABLE 14-continued

Name of compound

[structure]

135TRIAZINE2DIFLUOROMETHIO4BUTYLAMINO6ETHYLAMINO

[structure]

135TRIAZINE2DIFLUOROMETHIO4BUTYLAMINO6METHYL-AMINO

TABLE 15
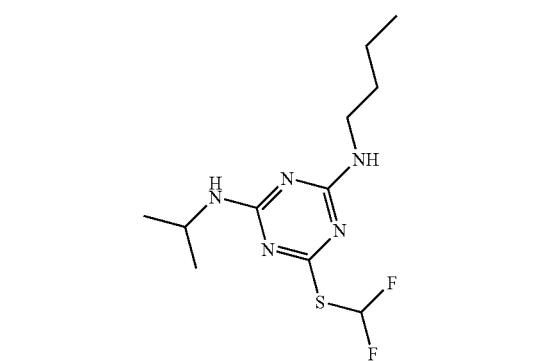
135TRIAZINE2DIFLUOROMETHIO41PROPYLAMINO6BUTYL-
AMINO
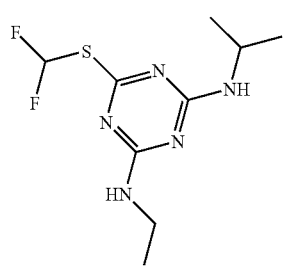
135TRIAZINE2DIFLUOROMETHIO41PROPYLAMINO6ETHYL-
AMINO
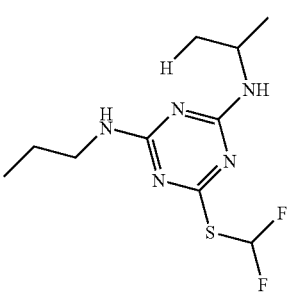
135TRIAZINE2DIFLUOROMETHIO41PROPYLAMINO6PROPYL-
AMINO
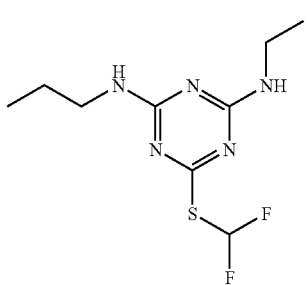
135TRIAZINE2DIFLUOROMETHIO4PROPYLAMINO6ETHYL-
AMINO
TABLE 16
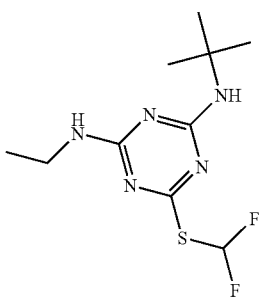
135TRIAZINE2DIFLUOROMETHIO4TBUTYL6ETHYLAMINO
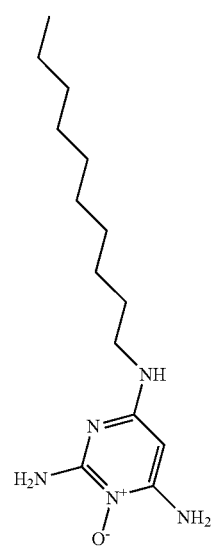
24DIAMINO5HEPTYL6MEPYRIMIDINE
24DIAMINO6DECYLAMINOPYRIMIDINE3OXIDE

TABLE 17
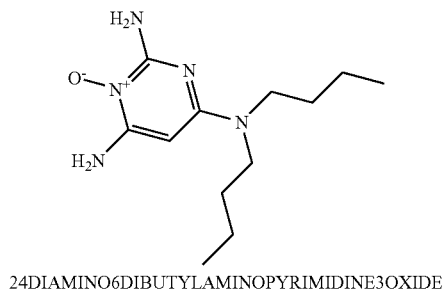
24DIAMINO6DIBUTYLAMINOPYRIMIDINE3OXIDE
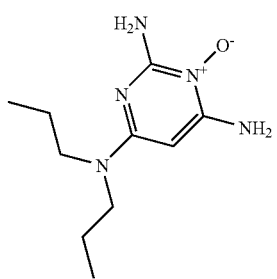
24DIAMINO6DIPROPYLAMINOPYRIMIDINE3OXIDE
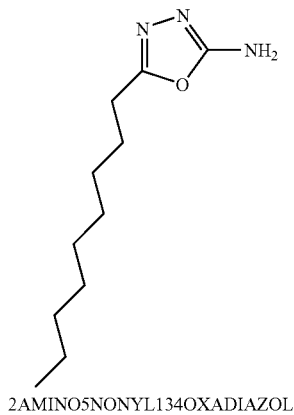
2AMINO5NONYL134OXADIAZOLE
TABLE 18
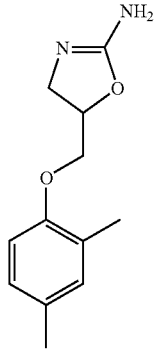
2OXAZOLINE2AMINO424DIMETHYLPHENOXYMETHYL
TABLE 18-continued
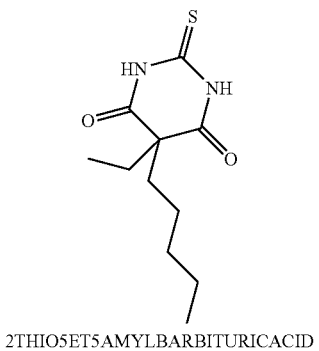
2THIO5ET5AMYLBARBITURICACID
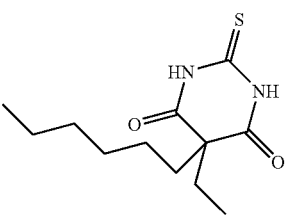
2THIO5ET5HEXYLBARBITURICACID
34DIETHOXYPHENYLCARBAMATEOPROPYL
TABLE 19
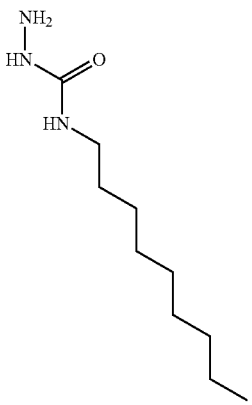
4DECYLSEMICARBAZIDE TABLE 19-continued
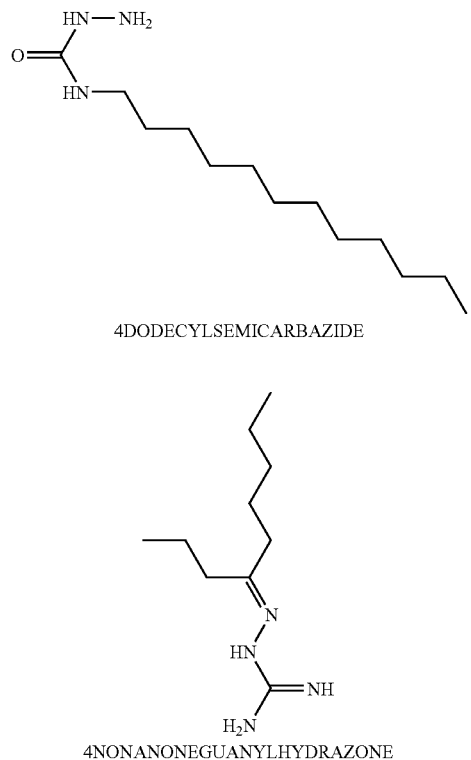
4DODECYLSEMICARBAZIDE
4NONANONEGUANYLHYDRAZONE
TABLE 20
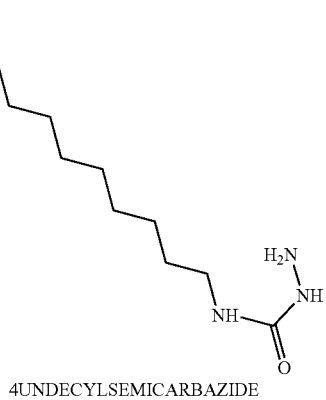
4UNDECYLSEMICARBAZIDE
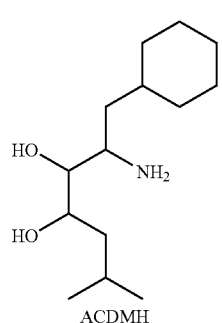
ACDMH
TABLE 20-continued
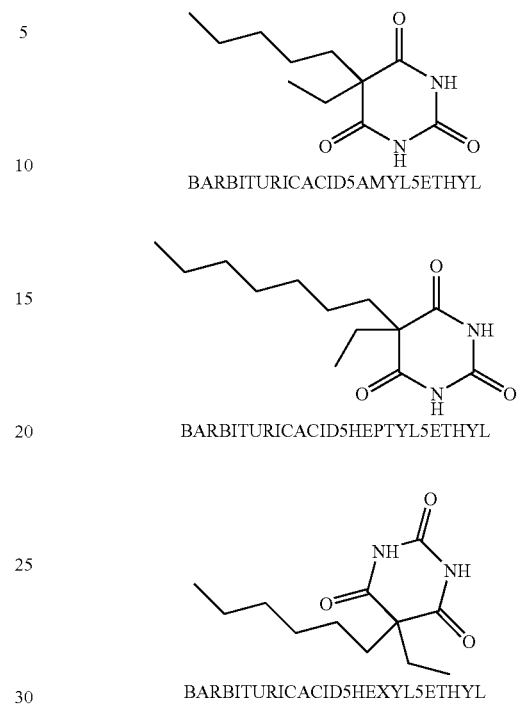
BARBITURICACID5AMYL5ETHYL
BARBITURICACID5HEPTYL5ETHYL
BARBITURICACID5HEXYL5ETHYL
TABLE 21
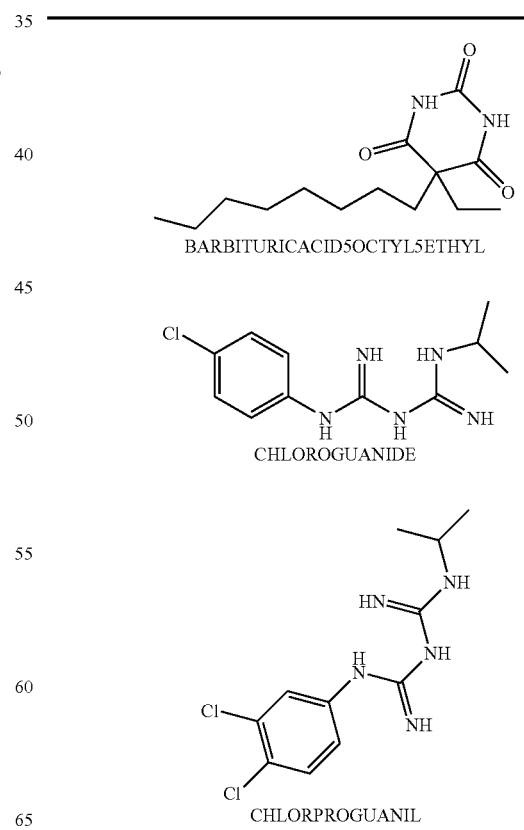
BARBITURICACID5OCTYL5ETHYL
CHLOROGUANIDE
CHLORPROGUANIL TABLE 21-continued
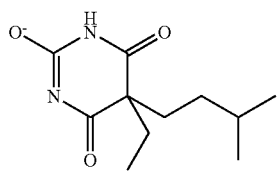
DIETPROTRIPTYLINESALTAMOBARBITAL
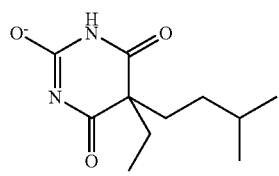
DIMEPROTRIPTYLINESALTAMOBARBITAL
TABLE 22
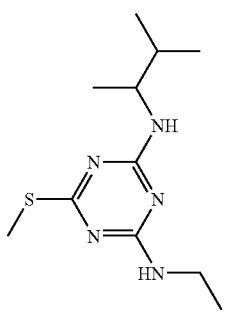
DIMETHAMETRYN
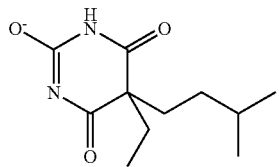
DIPRPROTRIPTYLINESALTAMOBARBITAL
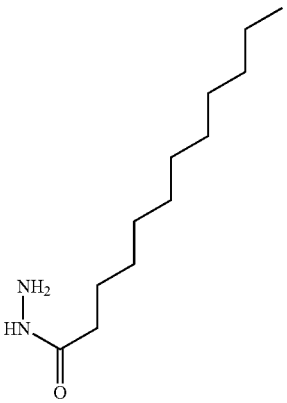
DODECANOICACIDHYDRAZIDE
TABLE 22-continued
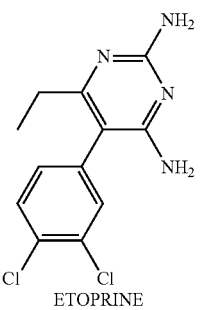
ETOPRINE
TABLE 23
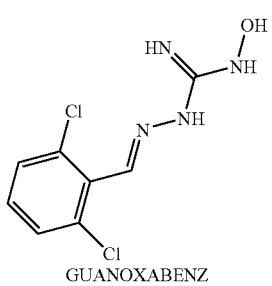
GUANOXABENZ
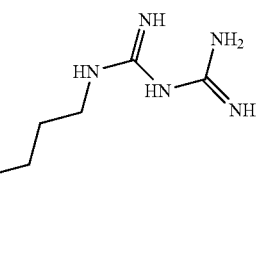
HEPTYLBIGUANIDE
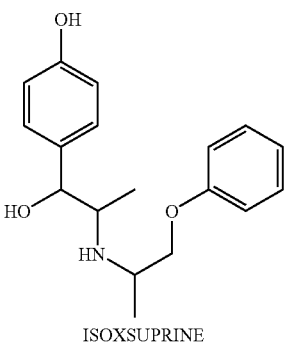
ISOXSUPRINE

TABLE 23-continued
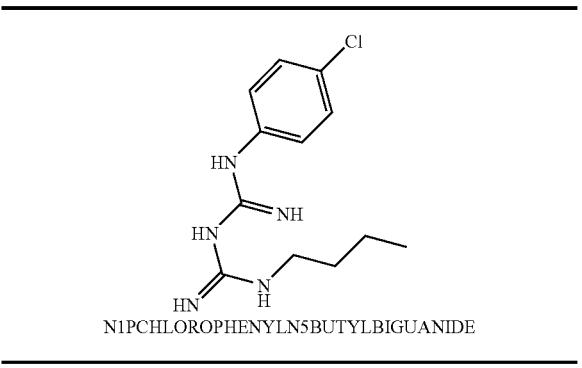
N1PCHLOROPHENYLN5BUTYLBIGUANIDE
TABLE 24
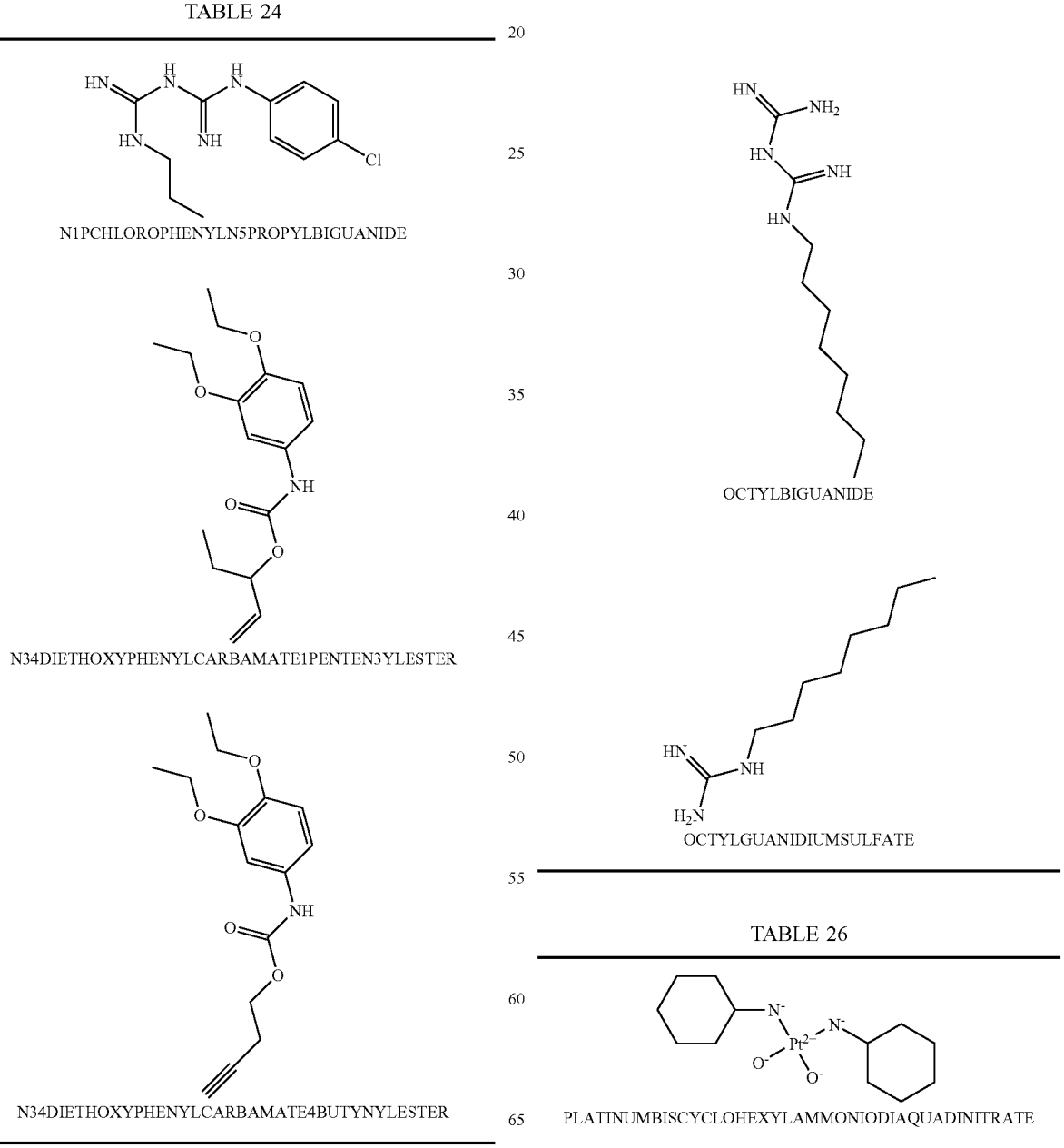
N1PCHLOROPHENYLN5PROPYLBIGUANIDE
N34DIETHOXYPHENYLCARBAMATE1PENTEN3YLESTER
N34DIETHOXYPHENYLCARBAMATE4BUTYNYLESTER
TABLE 25
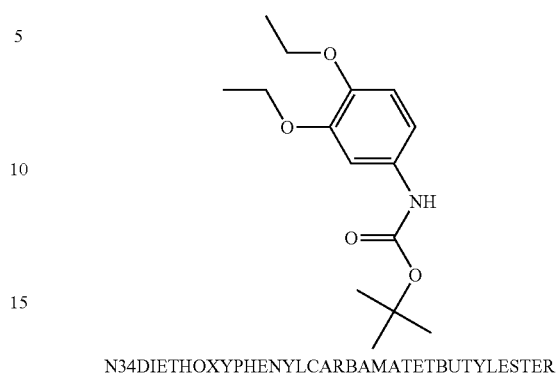
N34DIETHOXYPHENYLCARBAMATETBUTYLESTER
OCTYLBIGUANIDE
OCTYLGUANIDIUMSULFATE
TABLE 26
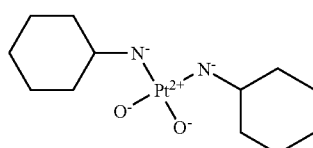
PLATINUMBISCYCLOHEXYLAMMONIODIAQUADINITRATE

TABLE 26-continued

PYRAZOLE3METHYL4NITRO5NDECYLCARBOXAMIDO

PYRIMIDINE24DIAMINO5PCHLOROBENZYL6ETHYL

PYRIMIDINE24DIAMINO5PCHLOROBENZYL6PROPYL

PYRIMIDINE24DIAMINO5PCHLOROPHENYL6IBUTYL

TABLE 27

PYRIMIDINE24DIAMINO5PCHLOROPHENYL6PROPYL

TABLE 27-continued

RILOPIROX

SIMAZINE2CYCLOHEXYLAMINEANALOG

TETRABARBITAL

TABLE 28

TETRABUTYLAMMONIUMAMOBARBITURATE

TABLE 28-continued
TRETHOCANOICACID
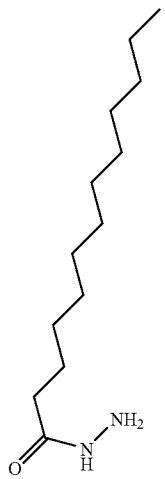
TRIDECANOICACIDHYDRAZIDE
TABLE 29
UNDECANOICACIDHYDRAZIDE
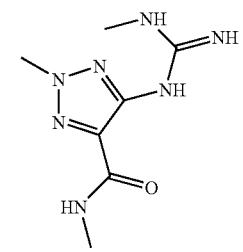
123TRIAZOLE2METHYL4METHYLCARBAMOYL53METHYL-
GUANIDINO
TABLE 29-continued
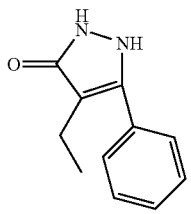
12DIHYDROPYRAZOLONE4ETHYL5PHENYL
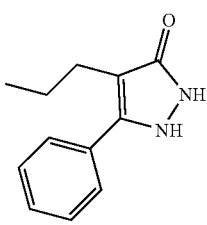
12DIHYDROPYRAZOLONE4PROPYL5PHENYL
TABLE 30
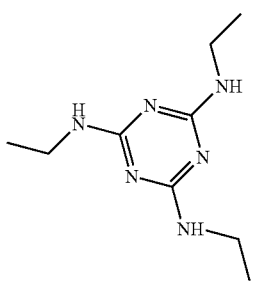
135TRIAZINE246TRISETHYLAMINO
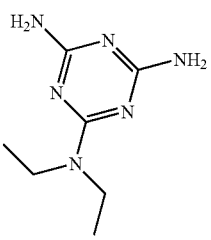
135TRIAZINE24DIAMINO6DIETHYLAMINO
1NAPHTHALENEAMINE3METHOXY

TABLE 30-continued

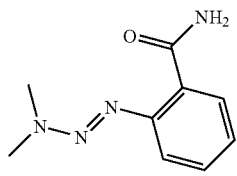

233DIMETHYL1TRIAZINOBENZAMIDE

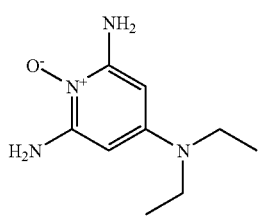

24DIAMINO6DIETHYLAMINOPYRIMIDINE3OXIDE

TABLE 31

24DIMETHOXYAMPHETAMINE

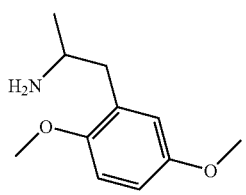

25DIMETHOXYAMPHETAMINE

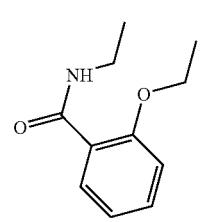

2ETHOXYBENZAMIDENETHYL

TABLE 31-continued

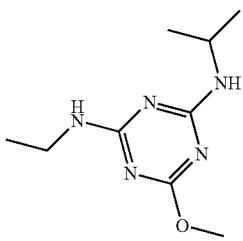

2METHOXY4ETAMINO6IPROPYLAMINOSTRIAZINE

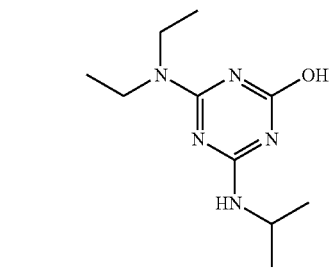

2OH4IPROPYLAMINO6DIETAMINOSTRIAZINE

TABLE 32

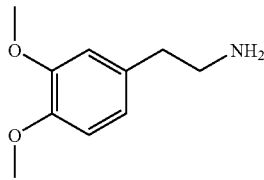

34DIMETHOXYPHENETHYLAMINE

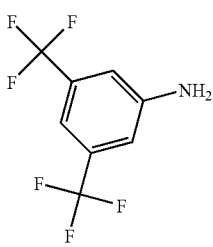

35BISTRIFLUOROMETHYLANILINE

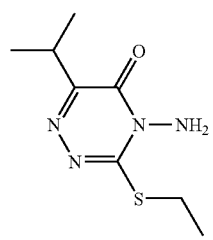

3ETHYLTHIO4AMINO6IPR124TRIAZINE5ONE

TABLE 32-continued
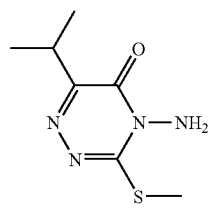
3METHIO4AMINO6IPR124TRIAZINE5ONE
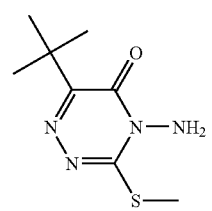
3METHIO4AMINO6TBU124TRIAZINE5ONE
TABLE 33
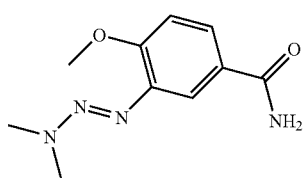
4METHOXY333DIMETHYLTRIAZENOBENZAMIDE
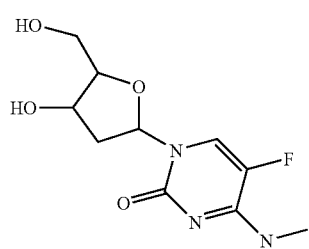
5FLUORONMETHYL2DEOXYCYTIDINE
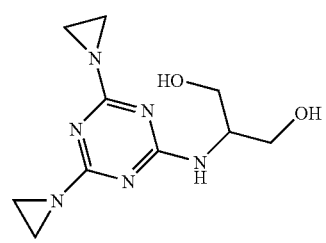
6BISHOCH2MEAMINO24DIAZIRIDINYLTRIAZINE
TABLE 33-continued
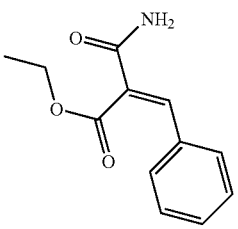
AAMIDOETHYLCINNAMATE
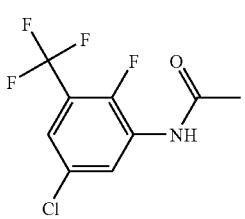
ACETANILIDE2FLUORO3TRIFLUOROMETHYL5CHLORO
TABLE 34
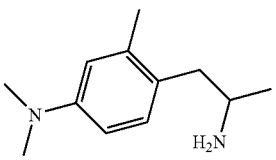
AMIFLAMINE
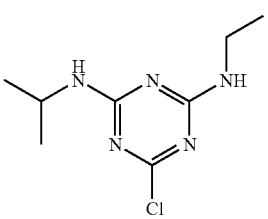
ATRAZINE
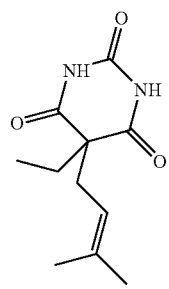
BARBITURICACID5ETHYL53METHYLBUTEN2YL TABLE 34-continued

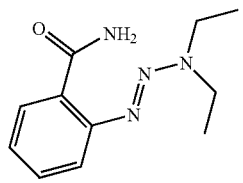

BENZAMIDE233DIETHYLTRIAZENYL

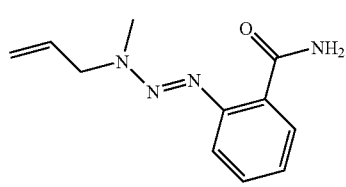

BENZAMIDE23METHYL3ALLYLTRIAZENYL

TABLE 35

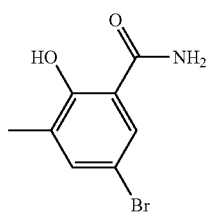

BENZAMIDE2HYDROXY3METHYL5BROMO

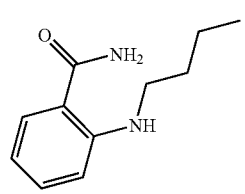

BENZAMIDEOBUTYLAMINO

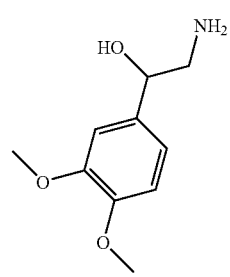

BENZENEETHANEAMINEAHYDROXY34DIMETHOXY

TABLE 35-continued

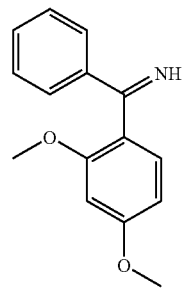

BENZENEMETHANIMINE24DIMETHOXYAPHENYL

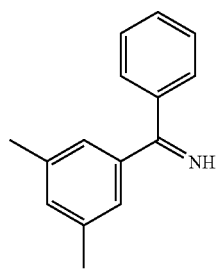

BENZENEMETHANIMINE35DIMETHYLAPHENYL

TABLE 36

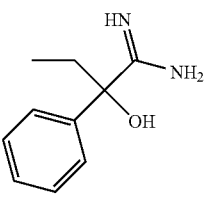

BENZENEMETHANOLAETHYLAAMIDINO

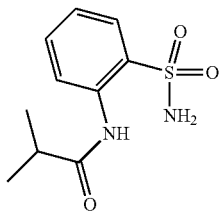

BENZENESULFONAMIDE2IBUTYROYLAMINO

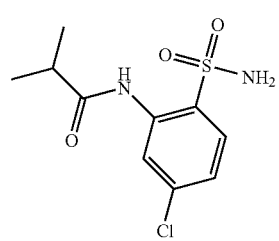

BENZENESULFONAMIDE2IBUTYROYLAMINO4CHLORO

TABLE 36-continued
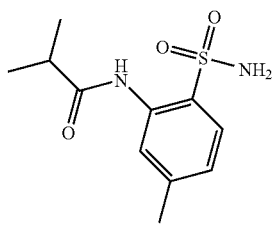
BENZENESULFONAMIDE2IBUTYLROYLAMINO4METHYL
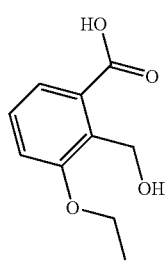
BENZOICACID2HYDROXYMETHYL3ETHOXY
TABLE 37
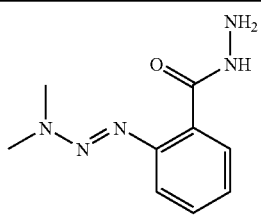
BENZOICACIDHYDRAZIDEO33DIMETRIAZINO
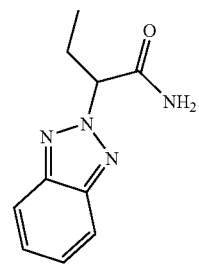
BENZOTRIAZOLE22BUTYRAMIDE
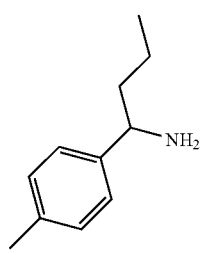
BUTYLAMINE1PTOLYL
TABLE 37-continued
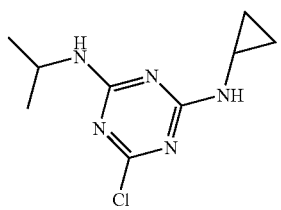
CYPRAZINE
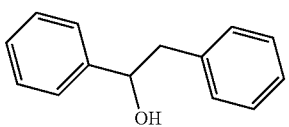
ETHANOL12DIPHENYL
TABLE 38
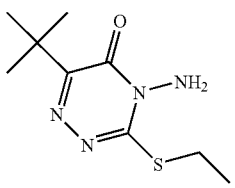
ETHIOZIN
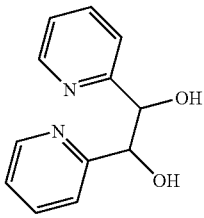
ETHYLENEGLYCOL12BIS2PYRIDYL
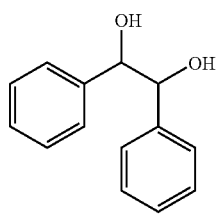
ETHYLENEGLYCOL12DIPHENYL
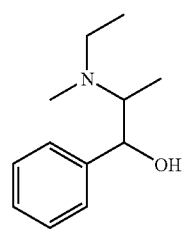
ETHYLEPHEDRINE TABLE 38-continued
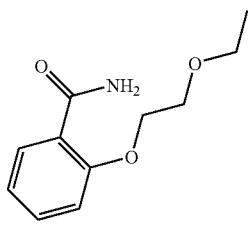
ETOSALAMIDE
TABLE 39
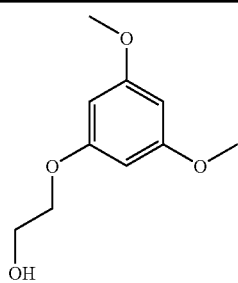
FLOVERINE
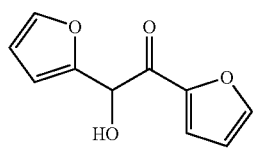
FURAN2CHOHCOFURYL
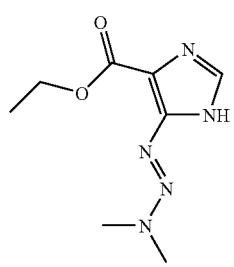
IMIDAZOLE4ETHOXYCARBONYL533DIMETHYLTRIAZENYL
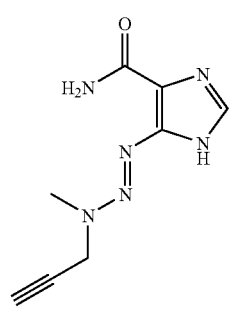
IMIDAZOLE5CARBOXAMIDE43METHYL3PROPYNYLTRIAZENYL
TABLE 40
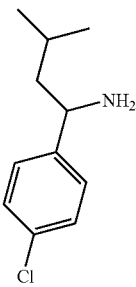
IPENTYLAMINEA4CHLOROPHENYL
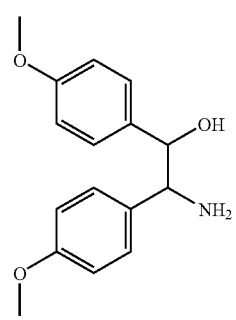
ISOLADOL
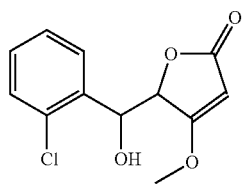
LOSIGAMONE
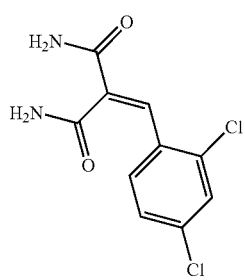
MALONAMIDE24DICHLOROBENZAL

TABLE 41
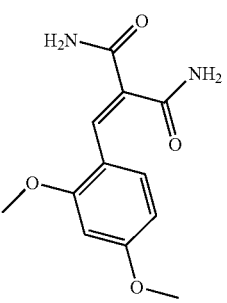
MALONAMIDE24DIMETHOXYBENZAL
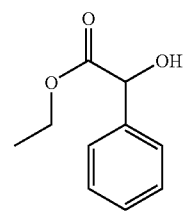
MANDELICACIDETHYLESTER
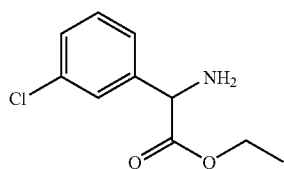
MCHLOROPHENYLGLYCINEETHYLESTER
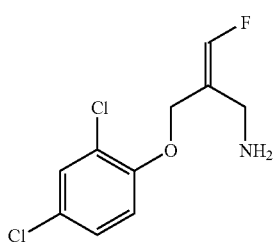
MDL72145
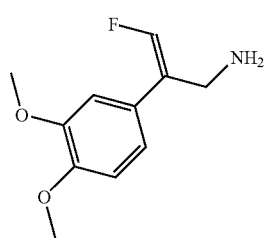
MDL72638
TABLE 42
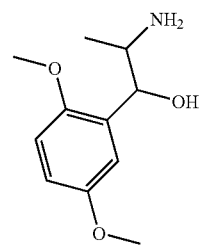
METHOXAMINE
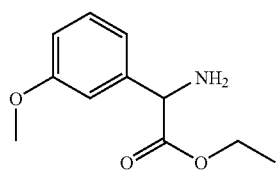
MMETHOXYPHENYLGLYCINEETHYLESTER
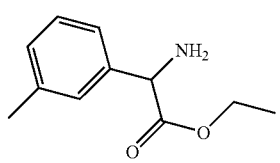
MMETHYLPHENYLGLYCINEETHYLESTER
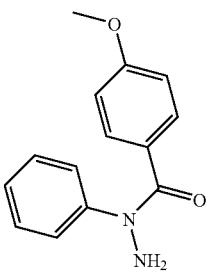
N1PHENYLN1PMETHOXYBENZOYLHYDRAZINE
NAPHTHALENE2AMINO4METHOXYCARBONYL
TABLE 43
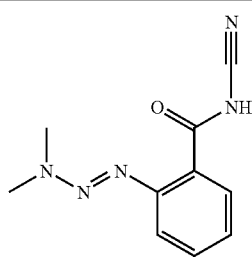
NCYANO233DIMETHYL1TRIAZENOBENZAMIDE TABLE 43-continued
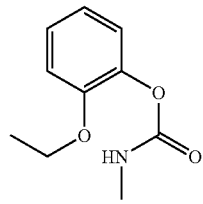
NMETHYL2ETHOXYPHENYLCARBAMATE
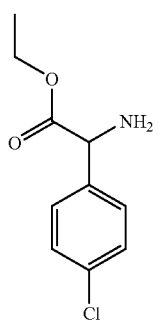
PCHLOROPHENYLGLYCINEETHYLESTER
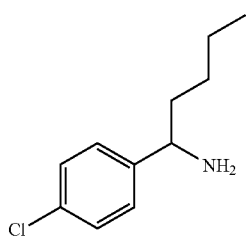
PENTYLAMINEAPCHLOROPHENYL
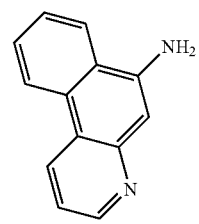
PHENANTHRIDINE6AMINO
TABLE 44
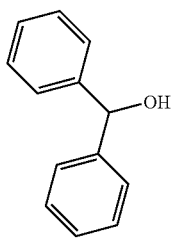
PHENYLAPYRIDYLCARBINOL
TABLE 44-continued
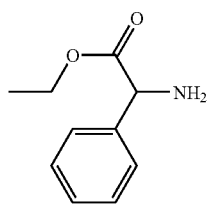
PHENYLGLYCINEETHYLESTER
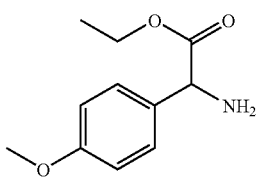
PMETHOXYPHENYLGLYCINEETHYLESTER
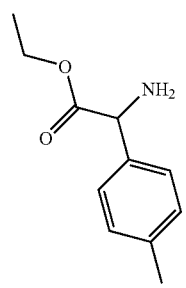
PMETHYLPHENYLGLYCINEETHYLESTER
TABLE 45
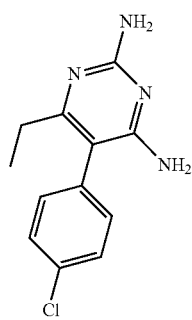
PYRIMETHAMINE
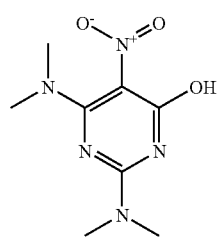
PYRIMIDINE24BISDIMETHYLAMINO6HYDROXY5NITRO TABLE 45-continued

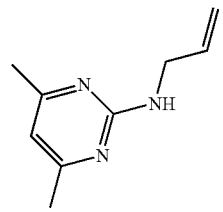

PYRIMIDINE2ALLYLAMINO46DIMETHYL

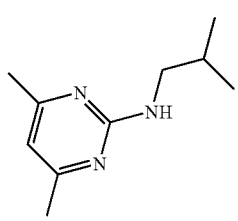

PYRIMIDINE21BUTYLAMINO46DIMETHYL

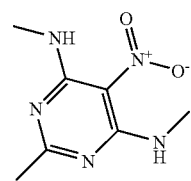

PYRIMIDINE2METHYL46BISMETHYLAMINO5NITRO

TABLE 46

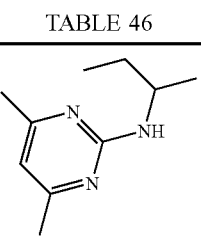

PYRIMIDINE2SECBUTYLAMINO46DIMETHYL

TABLE 46-continued

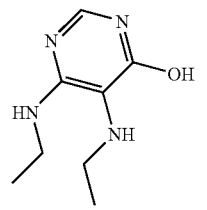

PYRIMIDINE45BISETHYLAMINO6HYDROXY

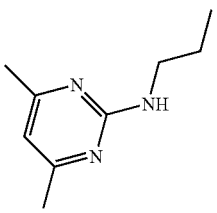

PYRIMIDINE46DIMETHYL2PROPYLAMINO

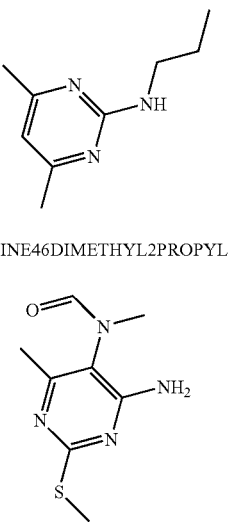

PYRIMIDINE4AMINO6METHYL5METHYL
FORMAMIDO2METHYLTHIO

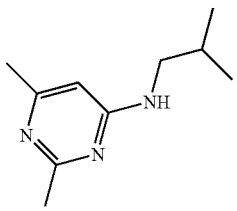

PYRIMIDINE41BUTYL26DIMETHYL

TABLE 47

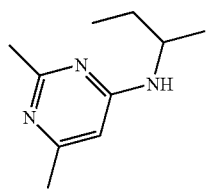

PYRIMIDINE4SECBUTYLAMINO26DIMETHYL

TABLE 47-continued
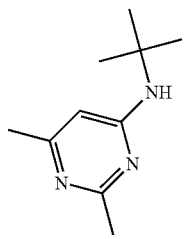
PYRIMIDINE4TBUTYLAMINO26DIMETHYL
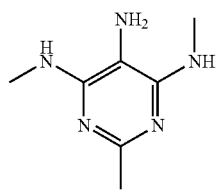
PYRIMIDINE5AMINO2METHYL46BISMETHYLAMINO
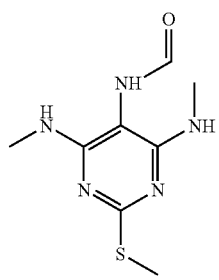
PYRIMIDINE5FORMAMIDO46BISMETHYLAMINO2METHYLTHIO
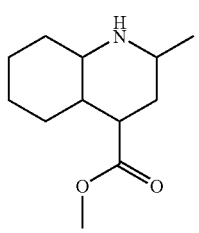
QUINOLINETRANSDECAHYDRO4METHOXYCARBONYL2METHYL

TABLE 48

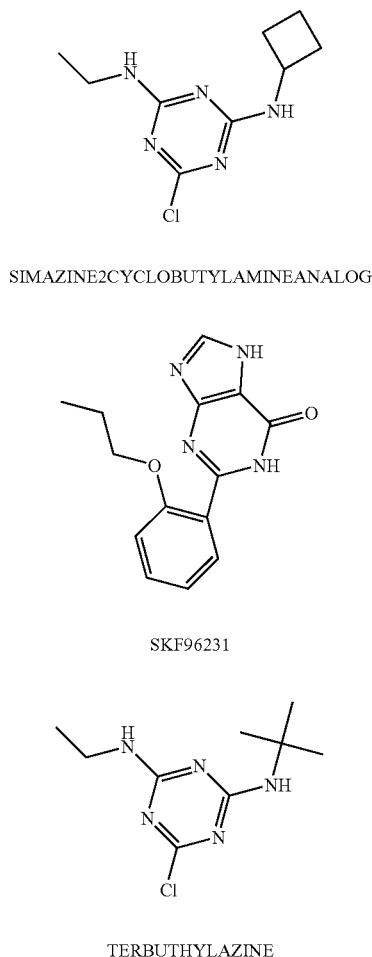

SIMAZINE2CYCLOBUTYLAMINEANALOG

SKF96231

TERBUTHYLAZINE

TABLE 48-continued

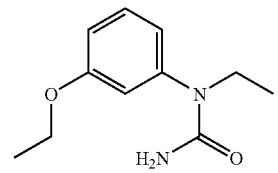

TROPALONE4IPROPYL7BROMO

UREA1ETHYL1METHOXYPHENYL

TABLE 49

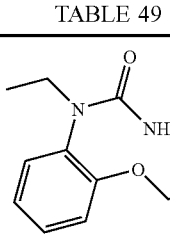

UREA1ETHYL1OETHOXYPHENYL

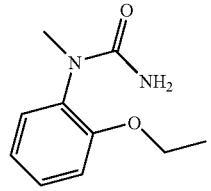

UREA1METHYL1OETHOXYPHENYL

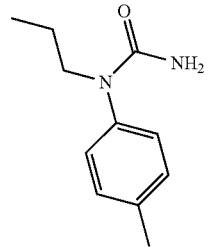

UREA1PROPYL1PTOLYL

TABLE 50

| Name of structure | MW | LUDI_ score | HB_ score | LIPO_ score | Rotlbon ds | Rule of 5 Violations | CONS_ score | LIGscore_ CFF |
|---|---|---|---|---|---|---|---|---|
| 10UNDECEN1OL | 170.2942 | −323 | 0 | 0 | | | 4 | 1.49 |
| 11DIPHENYLHYDRAZINE | 184.2402 | −66 | 0 | 29 | 2 | 0 | | |
| 1234H4ISOQUINOLINE58DIMETHOXY | 193.245 | −90 | 0 | 5 | 2 | 0 | | |
| 123BUTANETRIONE1DIMETHYLAMINO-2OXIME3METHOXIME | 187.198 | −95 | 0 | 0 | 5 | 0 | | |
| 12DIHYDROPYRAZOLONE4BUTYL5PHENYL | 216.2822 | −166 | 0 | 5 | | | 5 | 2.2 |
| 134DIMETHOXYPHENYL2PROPANOL | 196.2456 | −110 | 0 | 35 | 5 | 0 | | |
| 135TRIAZINE246TRIAMINENNDIETHYL | 182.2278 | −125 | 0 | 20 | 4 | 0 | | |
| 135TRIAZINE2DIFLUOROMETHIO46BISETHYLAMINO | 249.281 | −188 | 0 | 8 | | | 4 | 1.75 |
| 135TRIAZINE2DIFLUOROMETHIO46BISMETHYLAMINO | 221.2274 | −145 | 0 | 0 | | | 4 | 1.51 |

TABLE 50-continued

| Name of structure | MW | LUDI_score | HB_score | LIPO_score | Rotlbonds | Rule of 5 Violations | CONS_score | LIGscore_CFF |
|---|---|---|---|---|---|---|---|---|
| 135TRIAZINE2DIFLUOROMETHIO4ETHYL-AMINO6METHYLAMINO | 235.2542 | −171 | 0 | 0 | | | 5 | 2.24 |
| 135TRIAZINE2DIFLUOROMETHIO4TBUTYL-AMINO6METHYLAMINO | 263.3078 | −166 | 0 | 5 | | | 5 | 1.11 |
| 13PROPANEDIOL2BUTYL2ETHYL | 160.2558 | −236 | 0 | 11 | | | 4 | 1.96 |
| 1HYDROXYPENTACHLOROCYCLOHEXANE | 272.3857 | −66 | 0 | 29 | 1 | 0 | | |
| 1NDIMETHYLHEXAHYDROFLUOREN4AAMINE | 215.3376 | −120 | 0 | 0 | 1 | 0 | | |
| 1PHENYL13PROPANEDIOL2DICHLOROACETAMIDO | 278.1346 | −195 | 0 | 26 | | | 4 | 1.46 |
| 21HPTERIDINONE4AMINO167TRIMETHYL | 205.2188 | −95 | 0 | 0 | 0 | 0 | | |
| 226CL24MEOPHENYLIMINOIMIDAZOLINE | 260.1224 | −66 | 0 | 29 | 2 | 0 | | |
| 226DIETHYLPHENYLIMINOIMIDAZOLIDINE | 217.3132 | −128 | 0 | 17 | 3 | 0 | | |
| 234TRIMETHOXYAMPHETAMINE | 225.287 | −104 | 0 | 41 | 5 | 0 | | |
| 235TRICHLOROPHENOL | 197.4481 | −95 | 0 | 0 | 1 | 0 | | |
| 235TRIMETHYLPHENOL | 136.1932 | −95 | 0 | 0 | 1 | 0 | | |
| 23BENZOOCTAHYDRONAPHTHALENE34DIOH34DIAX | 218.295 | −63 | 0 | 32 | 2 | 0 | | |
| 24DICHLOROBENZYLALCOHOL | 177.0298 | −118 | 0 | 2 | 2 | 0 | | |
| 24DICHLROPHENYLARSONICACID | 270.9313 | −90 | 0 | 5 | 3 | 0 | | |
| 25DIMETHOXY4METHIOAMPHETAMINE | 241.3476 | −127 | 0 | 44 | 5 | 0 | | |
| 25DIMETHOXY4METHYLAMPHETAMINE | 209.2876 | −122 | 0 | 23 | 4 | 0 | | |
| 26DIMETHYL4PYRIMIDINAMINE | 123.1572 | −95 | 0 | 0 | 0 | 0 | | |
| 2ALLYLPHENOL3METHOXY | 164.2036 | −145 | 0 | 0 | | | 4 | 1.72 |
| 2AMINO2TETRAFLUOROETHYLVINYLPHENYLTHIONE | 263.2524 | −122 | 0 | 23 | 4 | 0 | | |

TABLE 51

| | | | | | | | | |
|---|---|---|---|---|---|---|---|---|
| 2AMINO4METHOXY6TRICHLORMETHYLSYMTRIAZINE | 243.4797 | −120 | 0 | 0 | 1 | 0 | | |
| 2CHLOROETHYLN3CHLOROPHENYLCARBAMATE | 234.0816 | −110 | 0 | 35 | 5 | 0 | | |
| 2MEO46BISIPROPYLAMINOSTRIAZINE | 225.293 | −122 | 0 | 23 | 5 | 0 | | |
| 2METHIO4ETAMINO6IPRAMINOSTRIAZINE | 227.3268 | −171 | 0 | 0 | | | 4 | 1.92 |
| 2METHOXY4MEAMINO6IPROPYLAMINOSTRIAZINE | 197.2394 | −115 | 0 | 5 | 4 | 0 | | |
| 2METHYL4BENZYLAMINO123BENZOTRIAZINIUMIODIDE | 251.3103 | −107 | 0 | 38 | 3 | 0 | | |
| 2METHYLTHIOPHENYLCARBAMATENMETHYL | 197.2514 | −120 | 0 | 0 | 4 | 0 | | |
| 2NNDIETHYLAMINO1PHENYLETHANOL | 193.2882 | −201 | 0 | 20 | | | 4 | 1.56 |
| 2OH46BISETHYLAMINOSTRIAZINE | 183.2126 | −125 | 0 | 20 | 5 | 0 | | |
| 2OH4ETAMINO6DIETAMINOSTRIAZINE | 211.2662 | −171 | 0 | 0 | | | 5 | 1.92 |
| 2OH4ETAMINO6IPROPYLAMINOSTRIAZINE | 197.2394 | −122 | 0 | 23 | 5 | 0 | | |
| 2PYRIDINEAMINE46DIMETHYL | 122.1694 | −95 | 0 | 0 | 0 | 0 | | |
| 2PYRIDONE56BISMETHIOMETHYL | 215.3278 | −196 | 0 | 0 | | | 4 | 2.06 |
| 345TRIMETHOXYAMPHETAMINE | 225.287 | −125 | 0 | 20 | 5 | 0 | | |
| 34DIMETHOXYAMPHETAMINE | 195.2608 | −128 | 0 | 17 | 4 | 0 | | |
| 34DIMETHOXYBENZYLALCOHOL | 168.192 | −120 | 0 | 0 | 4 | 0 | | |
| 35DIBROMOPHENOL | 251.905 | −95 | 0 | 0 | 1 | 0 | | |
| 35DICHLOROANILINE | 162.0182 | −95 | 0 | 0 | 0 | 0 | | |
| 35DICHLOROPHENOL | 163.003 | −95 | 0 | 0 | 1 | 0 | | |
| 35DICLC6H3NHNCCNCOOET | 286.117 | −94 | 0 | 26 | 6 | 0 | | |
| 35DIMETHOXY4BROMOPHENETHYLAMINE | 260.1301 | −113 | 0 | 32 | 4 | 0 | | |
| 35DIMETHOXYPHENOL | 154.1652 | −95 | 0 | 0 | 3 | 0 | | |
| 35DIMETHYLANILINE | 121.1816 | −95 | 0 | 0 | 0 | 0 | | |
| 35DIMETHYLPHENOL | 122.1664 | −95 | 0 | 0 | 1 | 0 | | |
| 35DITBUTYLPHENOL | 206.3272 | −125 | 0 | 20 | 3 | 0 | | |
| 3CLC6H4NHNCCNCOOET | 251.6719 | −91 | 0 | 29 | 6 | 0 | | |
| 3ETOCOPYRIDO12APYRIMIDIN4ONH76ME | 238.2858 | −100 | 0 | 20 | 3 | 0 | | |
| 3METHIO4AMINO6ETHYL124TRIAZINE5ONE | 186.2312 | −116 | 0 | 29 | 2 | 0 | | |
| 3METHIO4AMINO6ME124TRIAZINE5ONE | 172.2044 | −112 | 0 | 8 | 1 | 0 | | |
| 3METHOXY4AMINO6IPR124TRIAZINE5ONE | 184.1974 | −112 | 0 | 8 | 2 | 0 | | |
| 3PHENYLAMINO4AMINO6IPR124TRIAZINE5ONE | 245.2834 | −91 | 0 | 29 | 3 | 0 | | |
| 3PROPYL4IPROPYLPHENOL | 178.2736 | −171 | 0 | 0 | | | 5 | 1.07 |
| 3PYRIDINEMETHANOLA2PROPYNYLA34DICLPHENYL | 292.164 | −170 | 0 | 26 | | | 5 | 1.47 |
| 3PYRIDINEMETHANOLA2PROPYNYLA4FLUOROPHENYL | 241.2643 | −170 | 0 | 26 | | | 5 | 1.48 |

TABLE 52

| | | | | | | | | |
|---|---|---|---|---|---|---|---|---|
| 3PYRIDINEMETHANOLA2PROPYNYLA4TOLYL | 237.3006 | −167 | 0 | 29 | | | 5 | 1.06 |
| 41HPTERIDINIMINE167TRIMETHYL | 189.2194 | −95 | 0 | 0 | 0 | 0 | | |
| 45DICHLORO2METHOXYPHENOL | 193.0292 | −95 | 0 | 0 | 2 | 0 | | |
| 4ETHYL3PROPYLPHENOL | 164.2468 | −171 | 0 | 0 | | | 5 | 1.3 |
| 4METHYLNETHYLHEXAHYDROFLUOREN4AAMINE | 229.3644 | −110 | 0 | 35 | 2 | 0 | | |
| 4OCTANONEGUANYLHYDRAZONE | 170.257 | −196 | 0 | 0 | | | 4 | 1.86 |
| 4PTERIDINAMINE12DIHYDRO2IMINE167TRIMETHYL | 204.234 | −95 | 0 | 0 | 0 | 0 | | |
| 5AMINO124DICHLOROPHENYLTETRAZOLE | 230.056 | −81 | 0 | 14 | 1 | 0 | | |
| 5NONANOL | 144.2564 | −224 | 0 | 23 | | | 4 | 1.55 |
| 5NONANOL5BUTYL | 200.3636 | −300 | 0 | 23 | | | 4 | 1.89 |
| 622DIME5ME13DIOXAN5YLAM24DIAZIRIDTRIAZ | 306.3668 | −120 | 0 | 0 | 4 | 0 | | |
| 62PENHYDROPYRANYL4AM3METHIO124TRIAZINONE | 242.2952 | −64 | 0 | 56 | 2 | 0 | | |
| 6IPROPYL4AMINO3MEAMINO124TRIAZIN5ONE | 183.2126 | −120 | 0 | 0 | 2 | 0 | | |
| 8QUINOLINAMINE6METHOXY | 174.2018 | −95 | 0 | 0 | 1 | 0 | | |
| 8QUINOLINOL6TRIFLUOROMETHYL | 213.1587 | −120 | 0 | 0 | 1 | 0 | | |
| AAMIDO4METHYLETHYLCINNAMATE | 233.2664 | −120 | 0 | 0 | 5 | 0 | | |
| AAMIDOMETHYLCINNAMATE | 205.2128 | −72 | 0 | 23 | 4 | 0 | | |
| ACETANILIDE23DICHLORO5TRIFLUOROMETHYL | 272.0537 | −120 | 0 | 0 | 2 | 0 | | |
| ACETANILIDE2BROMO35DICHLORO | 282.9515 | −95 | 0 | 0 | 2 | 0 | | |
| ACETANILIDE2BROMO3TRIFLUOROMETHYL5CHLORO | 316.5047 | −120 | 0 | 0 | 2 | 0 | | |
| ACETANILIDE2CHLORO3TRIFLUOROMETHYL5BROMO | 316.5047 | −120 | 0 | 0 | 2 | 0 | | |
| ACETANILIDE35DIMETHYL | 163.2188 | −95 | 0 | 0 | 2 | 0 | | |
| AJMALINE | 326.4376 | −97 | 0 | 23 | 3 | 0 | | |
| ANILINE2METHOXY5CHLORO | 157.5993 | −95 | 0 | 0 | 1 | 0 | | |
| ANILINE2METHOXY5METHYL | 137.181 | −95 | 0 | 0 | 1 | 0 | | |
| ANILINE35DIBROMO | 250.9202 | −95 | 0 | 0 | 0 | 0 | | |
| ANILINE35DIIODO | 344.9212 | −95 | 0 | 0 | 0 | 0 | | |
| ANILINE35DIMETHOXY | 153.1804 | −95 | 0 | 0 | 2 | 0 | | |
| ANILINE3CHLORO5METHOXY | 157.5993 | −95 | 0 | 0 | 1 | 0 | | |
| ANTAZONITE | 268.348 | −171 | 0 | 0 | | | 5 | 0.78 |
| APHENYLBUYRAMIDE | 163.2188 | −157 | 0 | 14 | | | 4 | 1.85 |
| ASPARTICACIDDIETHYLESTER | 189.2108 | −192 | 0 | 29 | | | 4 | 1.83 |
| ASPIDINOL | 224.256 | −122 | 0 | 23 | 6 | 0 | | |
| BAYA6781 | 210.3186 | −125 | 0 | 20 | 2 | 0 | | |

TABLE 53

| | | | | | | | | |
|---|---|---|---|---|---|---|---|---|
| BENZAMIDE23AZETIDINYLTRIAZENE | 204.231 | −95 | 0 | 0 | 3 | 0 | | |
| BENZAMIDE23METHYL3BUTYLTRIAZENYL | 234.3004 | −109 | 0 | 62 | 6 | 0 | | |
| BENZAMIDE23METHYL3ETHYLTRIAZENYL | 206.2468 | −100 | 0 | 20 | 4 | 0 | | |
| BENZAMIDEODICHLOROACETYLAMINO | 247.0804 | −118 | 0 | 2 | 4 | 0 | | |
| BENZAMIDEOISOPROPYLAMINO | 178.2334 | −91 | 0 | 29 | 3 | 0 | | |
| BENZENEETHANEAMINE2METHOXY | 151.2078 | −131 | 0 | 14 | 3 | 0 | | |
| BENZENEETHANEAMINEAHYDROXYNETHYL34DIMETHOXY | 225.287 | −191 | 0 | 5 | | | 4 | 1.82 |
| BENZENEETHANEAMINEAHYDROXYNMETHYL34DIMETHOXY | 211.2602 | −169 | 0 | 2 | | | 5 | 2.34 |
| BENZENEETHANEAMINENSBUTYLAHYDROXY34DIMETHOXY | 253.3406 | −216 | 0 | 5 | | | 4 | 1.82 |
| BENZENEMETHANAMINE34DIMETHOXY | 167.2072 | −118 | 0 | 2 | 3 | 0 | | |
| BENZENESULFONAMIDE2IBUTYROYLAMINO | 242.2922 | −110 | 0 | 35 | 4 | 0 | | |
| BENZENESULFONAMIDE2IBUTYROYLAMINO4METHOXY | 272.3184 | −116 | 0 | 29 | 5 | 0 | | |
| BENZIMIDAZOLE2HYDROXYMETHYL1METHYL | 162.1908 | −120 | 0 | 0 | 2 | 0 | | |
| BENZOFURAN3AMINE23DIHYDRO5METHYLN1PYRROLIDINYLACETYL | 260.3352 | −127 | 0 | 44 | 4 | 0 | | |
| BENZOPHENONEHYDRAZONE | 196.2512 | −90 | 0 | 5 | 2 | 0 | | |
| BENZOTRIAZOLE12HEXANAMIDE | 232.2846 | −204 | 0 | 17 | | | 4 | 1.48 |
| BENZYLALCOHOL2HYDROXY35DICHLORO | 193.0292 | −118 | 0 | 2 | 3 | 0 | | |
| BENZYLALCOHOL35DIBROMO2HYDROXY | 281.9312 | −118 | 0 | 2 | 3 | 0 | | |
| BENZYLALCOHOL35DIMETHOXY4HYDROXY | 184.1914 | −120 | 0 | 0 | 5 | 0 | | |
| BENZYLSULFONAMIDE2METHOXYCARBONYL | 229.2502 | −116 | 0 | 29 | 4 | 0 | | |
| BETABENZALBUTYRAMIDE | 175.2298 | −119 | 0 | 26 | 3 | 0 | | |
| BICYCLO310HEXAN3OL4METHYL1ISOPROPYL | 154.2516 | −120 | 0 | 0 | 2 | 0 | | |
| BUTYLAMINE1PHENYL | 149.2352 | −148 | 0 | 23 | | | 4 | 1.41 |
| C3C1BUTENYL4CHYDROXYMECYCLOPENTENE | 152.2358 | −171 | 0 | 0 | | | 5 | 0.78 |
| CGP39551 | 237.19186 | −207 | 0 | 14 | | | 4 | 2.32 |
| COMG1774 | 237.3412 | −212 | 0 | 35 | | | 4 | 1.58 |
| CYANAZINE | 240.6949 | −171 | 0 | 0 | | | 5 | 1.28 |
| CYPENAMINE | 161.2462 | −93 | 0 | 2 | 1 | 0 | | |
| CYPRODINIL | 225.2926 | −95 | 0 | 0 | 3 | 0 | | |
| DAZADROL | 287.7481 | −127 | 0 | 44 | 4 | 0 | | |

TABLE 54

| | | | | | | | | |
|---|---|---|---|---|---|---|---|---|
| DECANOICACIDHDRAZIDE | 186.2966 | −297 | 0 | 0 | | | 4 | 1.44 |
| DESETHYLATRAZINE | 187.6315 | −120 | 0 | 0 | 2 | 0 | | |
| DESISOPROPYLATRAZINE | 173.6047 | −106 | 0 | 14 | 2 | 0 | | |
| DIACETONEGLUCOSE | 260.2864 | −45 | 0 | 50 | 2 | 0 | | |
| DIHYDROCODEINE | 301.3846 | −81 | 0 | 14 | 2 | 0 | | |
| DIHYDROMORPHINE | 287.3578 | −90 | 0 | 5 | 2 | 0 | | |
| DIMETHIRIMOL2 | 209.2906 | −171 | 0 | 0 | | | 5 | 2.36 |
| DIMETHYLGUAIACOL | 152.1926 | −95 | 0 | 0 | 2 | 0 | | |
| DIMETHYLKETOMALONATEOXIME | 161.114 | −90 | 0 | 5 | 5 | 0 | | |
| DIMETHYLTARTRATE | 178.1414 | −171 | 0 | 0 | | | 4 | 1.86 |
| DIMETOFRINE | 227.2596 | −171 | 0 | 0 | | | 5 | 2.49 |
| DIPROBUTINE | 157.2984 | −227 | 0 | 20 | | | 4 | 1.47 |
| DIPROPYLHYDANTOIN | 184.2376 | −191 | 0 | 5 | | | 4 | 2.02 |
| DOM-3 | 209.2876 | −125 | 0 | 20 | 4 | 0 | | |
| ECGONINEMETHYLESTER | 199.2492 | −115 | 0 | 5 | 3 | 0 | | |
| ECTYLUREA | 156.184 | −120 | 0 | 0 | 4 | 0 | | |
| EFAROXAN | 216.2822 | −97 | 0 | 23 | 2 | 0 | | |
| ETHANOLAMINENPROPYLN2HYDROXYBUTYL | 175.2704 | −270 | 0 | 2 | | | 4 | 2.27 |
| ETHANOLAMINENTBUTYLN2HYDROXYBUTYL | 189.2972 | −64 | 0 | 56 | 8 | 0 | | |
| ETHENZAMIDE | 165.1914 | −91 | 0 | 29 | 3 | 0 | | |
| ETHYLAMINEN2HYDROXYPROPYLN2HYDROXYBUTYL | 175.2704 | −247 | 0 | 0 | | | 4 | 1.86 |
| ETHYLAMINENNBIS2HYDROXYBUTYL | 189.2972 | −272 | 0 | 0 | | | 4 | 2 |
| ETHYLENEGLYCOL12BIS6METHYLPYRID2YL | 244.2926 | −171 | 0 | 0 | | | 5 | 1.31 |
| FENIPENTOL | 164.2468 | −182 | 0 | 14 | | | 4 | 1.99 |
| FLUORENE9HYDROXYMETHYL | 196.2482 | −120 | 0 | 0 | 2 | 0 | | |
| FR115427 | 223.317 | −54 | 0 | 41 | 1 | 0 | | |
| GLYCEROL13DIETHYLETHER | 148.2016 | −218 | 0 | 29 | | | 4 | 1.74 |
| GUAIETOLIN | 212.245 | −196 | 0 | 0 | | | 4 | 2.59 |
| HEXANOICACID2ACETYLAMINOMETHYLESTER | 187.2382 | −198 | 0 | 23 | | | 4 | 1.8 |
| HEXAPRADOL | 283.4126 | −249 | 0 | 23 | | | 4 | 2.15 |
| HEXYLAMINE1PHENYL | 177.2888 | −195 | 0 | 26 | | | 4 | 1.99 |
| HYDROQUINONE23DIMETHOXY5METHYL | 184.1914 | −95 | 0 | 0 | 4 | 0 | | |
| HYDROQUINONE26DICHLORO | 179.0024 | −95 | 0 | 0 | 2 | 0 | | |
| HYDROQUINONE26DIMETHOXY | 170.1646 | −95 | 0 | 0 | 4 | 0 | | |

TABLE 55

| | | | | | | | | |
|---|---|---|---|---|---|---|---|---|
| HYDROQUINONE2METHYL6BROMO | 203.0351 | −95 | 0 | 0 | 2 | 0 | | |
| HYDROXYATRAZINE2 | 197.2394 | −119 | 0 | 26 | 4 | 0 | | |
| IMIDAZOLE4CARBOXAMIDE533BISCHLOROETHYLTRIAZINYL | 279.1284 | −196 | 0 | 0 | | | 4 | 1.47 |
| INDANOREX | 191.2724 | −107 | 0 | 38 | 3 | 0 | | |
| ISOLEUCINENACETYLNMETHYLAMINOAMIDE | 186.2534 | −167 | 0 | 29 | | | 5 | 0.91 |
| LEUCINEETHYLESTER | 159.2278 | −176 | 0 | 20 | | | 4 | 1.77 |
| LUPININE | 169.2662 | −120 | 0 | 0 | 2 | 0 | | |
| METHAMINAZOLAMIDE | 251.2778 | −120 | 0 | 0 | 3 | 0 | | |
| METHYLBENZOATE2SULFONAMIDO | 215.2234 | −109 | 0 | 11 | 3 | 0 | | |
| MILSTEM | 209.2906 | −95 | 0 | 0 | 6 | 0 | | |
| MISONIDAZOLEFLUORO | 219.1721 | −219 | 0 | 2 | | | 4 | 1.94 |
| MORPHOLINE325DIMETHOXYPHENYL | 223.2712 | −75 | 0 | 20 | 3 | 0 | | |
| N2N2N4N4TETRAMETHYLMELAMINE | 182.2278 | −95 | 0 | 0 | 2 | 0 | | |
| N2TBUTYLN1BENZENESULFONYLUREA | 256.319 | −130 | 0 | 41 | 5 | 0 | | |
| NAPHTHALENE1AMINO3CHLORO | 177.6329 | −112 | 0 | 8 | 0 | 0 | | |
| NBUTYL4CHLOROCINNAMAMIDE | 237.7285 | −118 | 0 | 53 | 6 | 0 | | |
| NMECARBAMICACIDOCYCLOPENTENYLPHENYLESTER | 217.267 | −95 | 0 | 0 | 4 | 0 | | |
| NMETHYL2ETHYLPHENYLCARBAMATE | 179.2182 | −120 | 0 | 0 | 4 | 0 | | |
| NMETHYL2IPROPOXYPHENYLCARBAMATE | 209.2444 | −120 | 0 | 0 | 5 | 0 | | |
| NMETHYLCARBAMATE3IPROPYL5METHYLPHENYL | 207.2718 | −120 | 0 | 0 | 4 | 0 | | |
| NMETHYLCARBAMATEOSBUTYLPHENYL | 207.2718 | −101 | 0 | 44 | 5 | 0 | | |
| NMETHYLCARBAMICACIDOCYCLOPENTYLPHENYLESTER | 219.2828 | −95 | 0 | 0 | 4 | 0 | | |
| NNDIETHYLANILINEMHYDROXY | 165.2346 | −145 | 0 | 0 | | | 4 | 1.41 |
| NOMETHOXYPHENYL3NPIPERIDINOACETAMIDE | 248.3242 | −110 | 0 | 35 | 5 | 0 | | |
| NORALPRENOLOL | 207.2718 | −221 | 0 | 0 | | | 4 | 1.86 |
| NSC118742 | 196.2546 | −95 | 0 | 0 | 3 | 0 | | |
| OBENZYLOXYBENZAMIDE | 227.2622 | −119 | 0 | 26 | 4 | 0 | | |
| OCTAHYDROPHENANTHREN4AAMINE9METHYL | 215.3376 | −87 | 0 | 8 | 0 | 0 | | |
| OPMETHYLBENZYLOXYBENZAMIDE | 241.289 | −104 | 0 | 41 | 4 | 0 | | |
| OPTUNAL | 289.28546 | −109 | 0 | 11 | 6 | 0 | | |
| OSDIMENPRPHOSPHORAMIDOTHIOATE | 183.20486 | −127 | 0 | 44 | 5 | 0 | | |
| OSDIPROPYLPHOSPHORAMIDOTHIOATE | 197.23166 | −207 | 0 | 14 | | | 4 | 1.9 |

TABLE 56

| | | | | | | | |
|---|---|---|---|---|---|---|---|
| PENTANOICACID2ACETYLAMINOMETHYLESTER | 173.2114 | −196 | 0 | 0 | | 4 | 2.16 |
| PENTYLAMINEAPHENYL | 163.262 | −170 | 0 | 26 | | 5 | 1.5 |
| PHENAMACIDE | 221.2986 | −207 | 0 | 14 | | 4 | 1.56 |
| PHENOL2ETHYL5METHYL | 136.1932 | −120 | 0 | 0 | 2 | 0 | |
| PHENOL2METHOXY4ETHYL | 152.1926 | −120 | 0 | 0 | 3 | 0 | |
| PHENOL3DIETHOXYPHOSPHINYL | 230.19986 | −125 | 0 | 20 | 6 | 0 | |
| PHENOL3ETHYL4METHYL | 136.1932 | −120 | 0 | 0 | 2 | 0 | |
| PHENOL5ETHYL3METHYL | 136.1932 | −120 | 0 | 0 | 2 | 0 | |
| PHENYLALANINEMETHYLESTER | 179.2182 | −171 | 0 | 0 | | 4 | 1.89 |
| PHENYLBORONICACID246TRIMETHYL | 164.0105 | −120 | 0 | 0 | 3 | 0 | |
| PHENYLPTOLYLCARBINOL | 198.264 | −122 | 0 | 23 | 3 | 0 | |
| PHOSPHORICAMIDEDIBUTYLESTER | 209.22466 | −247 | 0 | 0 | | 4 | 1.7 |
| PHOSPHOROHYDRAZIDICACIDDIPHENYLESTER | 264.22006 | −78 | 0 | 17 | 5 | 0 | |
| PICOLINHYDROXAMICACID | 166.1792 | −95 | 0 | 0 | 3 | 0 | |
| PILOCARPICACIDETHYLESTER | 254.3284 | −272 | 0 | 0 | | 4 | 1.97 |
| PROCYAZINE | 252.7059 | −171 | 0 | 0 | | 5 | 1.59 |
| PROPYLAMINEN2HYDROXYPROPYLN2HYDROXYBUTYL | 189.2972 | −272 | 0 | 0 | | 4 | 1.79 |
| PROPYLAMINENNBIS2HYDROXYBUTYL | 203.324 | −292 | 0 | 5 | | 4 | 2.11 |
| PTERIDINE4AMINO17DIHYDRO16DIMETHYL7OXO | 191.192 | −95 | 0 | 0 | 0 | 0 | |
| PURINE6ETHYLAMINO2METHYL | 177.2084 | −120 | 0 | 0 | 2 | 0 | |
| PYRAZINE2AMIDINO56DIMETHYL3METHYLAMINO | 179.2242 | −90 | 0 | 5 | 2 | 0 | |
| PYRAZOLO34DPYRIMIDINE46BISMETHYLAMINO | 178.1962 | −90 | 0 | 5 | 2 | 0 | |
| PYRAZOLO34DPYRIMIDINE4METHYLAMINO6METHYLTHIO | 195.2416 | −115 | 0 | 5 | 2 | 0 | |
| PYRIDINE26DICHLORO4HYDROXY | 163.9908 | −95 | 0 | 0 | 1 | 0 | |
| PYRIDINE2HYDROXY56BISMETHIOMETHYL | 215.3278 | −196 | 0 | 0 | | 4 | 1.7 |
| PYRIDINE4AMINO26DICHLORO | 163.006 | −95 | 0 | 0 | 0 | 0 | |
| PYRIDINE4HYDROXY26BISMETHOXYCARBONYL | 211.1738 | −95 | 0 | 0 | 5 | 0 | |
| PYRIMIDINE12DIHYDRO2IMINO146TRIMETHYL | 137.184 | −95 | 0 | 0 | 0 | 0 | |
| PYRIMIDINE1456TETRAHYDRO2AHYDROXYAMETHYLBENZYL | 204.2712 | −110 | 0 | 35 | 3 | 0 | |
| PYRIMIDINE24DIAMINO5BENZYL6METHYL | 214.2694 | −131 | 0 | 14 | 2 | 0 | |
| PYRIMIDINE24DIAMINO5PCHOROBENZYL6METHYL | 248.7145 | −113 | 0 | 32 | 2 | 0 | |
| PYRIMIDINE26DIMETHYL4METHYLAMINO | 137.184 | −95 | 0 | 0 | 1 | 0 | |

TABLE 57

| | | | | | | | |
|---|---|---|---|---|---|---|---|
| PYRIMIDINE2AMINO26DIMETHOXY | 155.156 | −95 | 0 | 0 | 2 | 0 | |
| PYRIMIDINE2AMINO46BISDIMETHYLAMINO | 181.24 | −90 | 0 | 5 | 2 | 0 | |
| PYRIMIDINE2AMINO46DIMETHYL | 123.1572 | −95 | 0 | 0 | 0 | 0 | |
| PYRIMIDINE2AMINO4CHLORO6DIMETHYLAMINO | 172.6169 | −95 | 0 | 0 | 1 | 0 | |
| PYRIMIDINE2AMINO4CHLORO6METHYLAMINO | 158.5901 | −95 | 0 | 0 | 1 | 0 | |
| PYRIMIDINE2BUTYL4CHLORO6HYDROXY | 186.6407 | −118 | 0 | 53 | 4 | 0 | |
| PYRIMIDINE2BUTYLAMINO46DIMETHYL | 179.2644 | −166 | 0 | 5 | | 5 | 1.86 |
| PYRIMIDINE2HEXYLAMINO | 179.2644 | −207 | 0 | 14 | | 4 | 1.91 |
| PYRIMIDINE2HYDRAZINO4METHOXY6METHYL | 154.1712 | −95 | 0 | 0 | 2 | 0 | |
| PYRIMIDINE2HYDROXY46DIMETHYL | 124.142 | −95 | 0 | 0 | 1 | 0 | |
| PYRIMIDINE2IPENTYLAMINO46DIMETHYL | 193.2912 | −166 | 0 | 5 | | 5 | 2.03 |
| PYRIMIDINE456TRISMETHYLAMINO | 167.2132 | −90 | 0 | 5 | 3 | 0 | |
| PYRIMIDINE46DIMETHYL2METHYLAMINO | 137.184 | −95 | 0 | 0 | 1 | 0 | |
| PYRIMIDINE4ACETAMIDO5ETHOXYCARBONYL2METHYL | 223.231 | −103 | 0 | 17 | 5 | 0 | |
| PYRIMIDINE4AMINO6CHLORO2DIMETHYLAMINO | 172.6169 | −95 | 0 | 0 | 1 | 0 | |
| PYRIMIDINE4AMINO6CHLORO2METHYLAMINO | 158.5901 | −95 | 0 | 0 | 1 | 0 | |
| PYRIMIDINE4AMINO6METHYL5METHYLAMINO2METHYLTHIO | 184.2586 | −120 | 0 | 0 | 2 | 0 | |
| PYRIMIDINE4CHLORO26BISMETHYLAMINO | 172.6169 | −95 | 0 | 0 | 2 | 0 | |
| PYRIMIDINE4CHLORO2DIMETHYLAMINO6METHYLAMINO | 186.6437 | −95 | 0 | 0 | 2 | 0 | |
| PYRIMIDINE4CHLORO36DIHYDRO6IMINO3METHYL2METHYLAMINO | 172.6169 | −95 | 0 | 0 | 1 | 0 | |
| PYRIMIDINE4CHLORO6DIMETHYLAMINO2METHYLAMINO | 186.6437 | −95 | 0 | 0 | 2 | 0 | |
| PYRIMIDINE4DIETHOXYMETHYL6HYDROXY | 198.2212 | −221 | 0 | 0 | | 4 | 1.44 |
| PYRIMIDINE4HYDROXY26DIMETHYL | 124.142 | −95 | 0 | 0 | 1 | 0 | |
| PYRIMIDINE4HYDROXY2METHOXY6METHYL | 140.1414 | −95 | 0 | 0 | 2 | 0 | |
| PYRIMIDINE4IBUTYL26DIMETHYL | 179.2644 | −145 | 0 | 0 | | 5 | 2.11 |
| PYRIMIDINE4IPENTYLAMINO26DIMETHYL | 193.2912 | −166 | 0 | 5 | | 5 | 1.78 |
| PYRIMIDINE5AMINO2CHLORO4METHYL6METHYLAMINO | 172.6169 | −95 | 0 | 0 | 1 | 0 | |
| PYRIMIDINE5AMINO2METHYL4METHYLAMINO6METHYLTHIO | 184.2586 | −120 | 0 | 0 | 2 | 0 | |
| PYRIMIDINE5BUTYL4HYDROXY6METHYLTHIO | 198.2824 | −191 | 0 | 5 | | 4 | 2.02 |
| PYRIMIDINE5CARBAMOYL46DIMETHYL2METHYLAMINO | 180.209 | −87 | 0 | 8 | 2 | 0 | |

TABLE 58

| | | | | | | | | |
|---|---|---|---|---|---|---|---|---|
| PYRIMIDINE5CARBAMOYL4METHYL2METHYLAMINO | 166.1822 | −95 | 0 | 0 | 2 | 0 | | |
| PYRIMIDINE6CHLORO12DIHYDRO2IMINO1METHYL4METHYLAMINO | 172.6169 | −95 | 0 | 0 | 1 | 0 | | |
| QUINAZOLINE2TBUTYL34DIHYDRO4HYDROXY | 204.2712 | −106 | 0 | 14 | 2 | 0 | | |
| QUINOLINETRANSDECAHYDRO4CHLORO2METHYL | 187.7119 | −75 | 0 | 20 | 0 | 0 | | |
| RA81914 | 316.3992 | −100 | 0 | 20 | 4 | 0 | | |
| RAUWOLFINE | 314.4266 | −94 | 0 | 26 | 3 | 0 | | |
| SAMPIRTINE | 217.2453 | −125 | 0 | 20 | 2 | 0 | | |
| SECBUMETON | 225.293 | −166 | 0 | 5 | | | 5 | 1.5 |
| SELAGINE | 242.32 | −81 | 0 | 14 | 0 | 0 | | |
| SIMAZINE2CYCLOBUTYLAMINEANALOG | 227.6961 | −140 | 0 | 5 | | | 5 | 1.1 |
| SIMAZINE2CYCLOPROPYLAMINEANALOG | 213.6693 | −116 | 0 | 29 | 4 | 0 | | |
| SIMAZINE2CYCLOPROPYLMETHYLAMINEANALOG | 227.6961 | −171 | 0 | 0 | | | 5 | 1.32 |
| STRIAZINE2METHYL4METHYLAMINO6TRICHLOROMETHYL | 241.5071 | −120 | 0 | 0 | 1 | 0 | | |
| SYMTRIAZINE2DIETHYLAMINO4IPROPYLAMINO6METHOXY | 239.3198 | −171 | 0 | 0 | | | 5 | 1.18 |
| TARTARICACIDDIETHYLESTER | 206.195 | −201 | 0 | 20 | | | 4 | 1.81 |
| TERBUMETON | 225.293 | −128 | 0 | 17 | 5 | 0 | | |
| TETRAHYDROPYRAN24DIONE31ETHOXYIMINOBUTYL66-SPIRO4METHYLCYCLOHEXYL | 309.4046 | −130 | 0 | 41 | 6 | 0 | | |
| THIAZOLO54DPYRIMIDINE7AMINO5BUTYL | 208.2806 | −115 | 0 | 56 | 3 | 0 | | |
| TIQUINAMIDE | 206.305 | −120 | 0 | 0 | 1 | 0 | | |
| TOLDIMFOS | 197.17306 | −72 | 0 | 23 | 1 | 0 | | |
| TRIBUTYLTINHYDROXIDE2 | 307.0426 | −124 | 0 | 47 | 10 | 1 | | |
| TRIMETHYLCITRATE | 234.2054 | −192 | 0 | 29 | | | 4 | 1.56 |
| TYROSINEMETHYLESTER | 195.2176 | −171 | 0 | 0 | | | 4 | 1.46 |
| UREA1ETHYL1OANISYL | 194.2328 | −120 | 0 | 0 | 4 | 0 | | |
| UREA1PROPYL1MTOLYL | 192.2602 | −131 | 0 | 14 | 4 | 0 | | |
| UREA1PROPYL1PHENYL | 178.2334 | −116 | 0 | 29 | 4 | 0 | | |

EXAMPLE 7

Decrease of Activity by LBD Deletion Mutant

Figure 7:
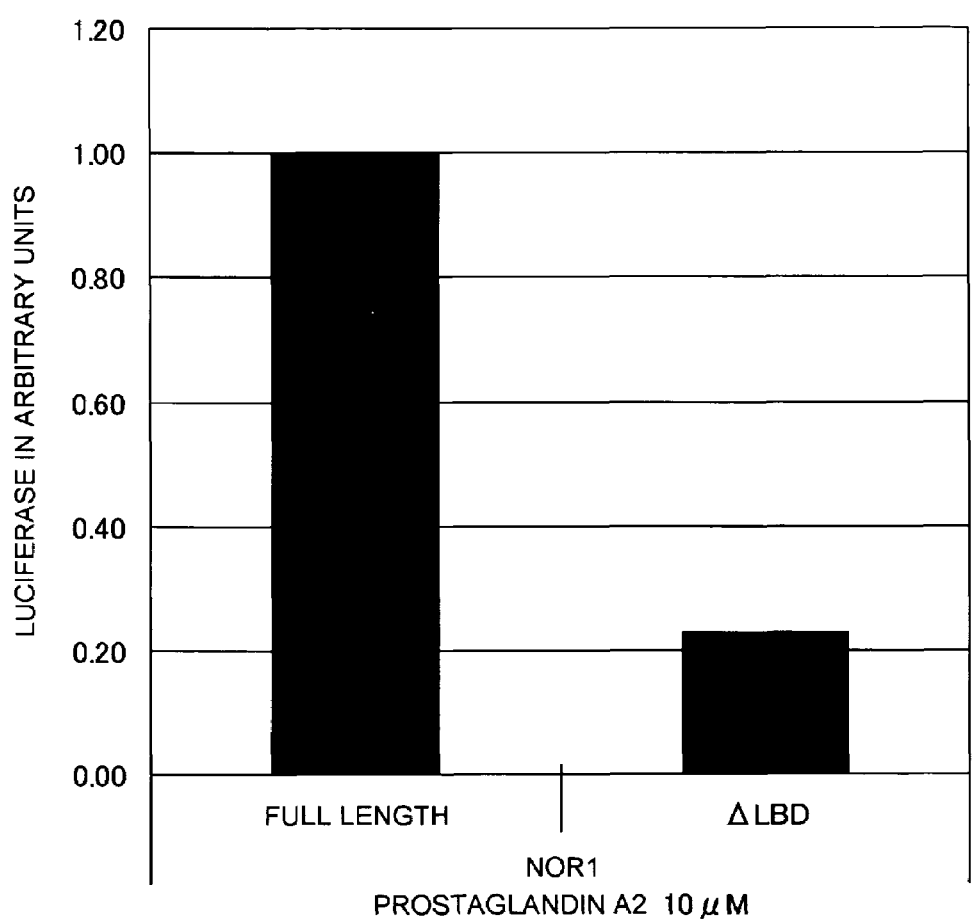
FIG. 7 shows a graph demonstrating the decrease of the transcriptional activity of prostaglandin $A_2$ due to use of the LBD deletion mutant of NOR-1. ΔLBD denotes the deletion mutant.

The use of a Nor1 gene that completely lacked the LBD region in the Mammalian Two Hybrid reporter system led to a remarkable suppression of the transcriptional activity due to prostaglandin $A_2$ (FIG. 7). Therefore, prostaglandin $A_2$ was implicated to function by actually acting on the LBD region of the nuclear receptor.

EXAMPLE 8

Demonstration of the Binding of PGA Derivatives to Nor1 using BIAcor

Figure 8:
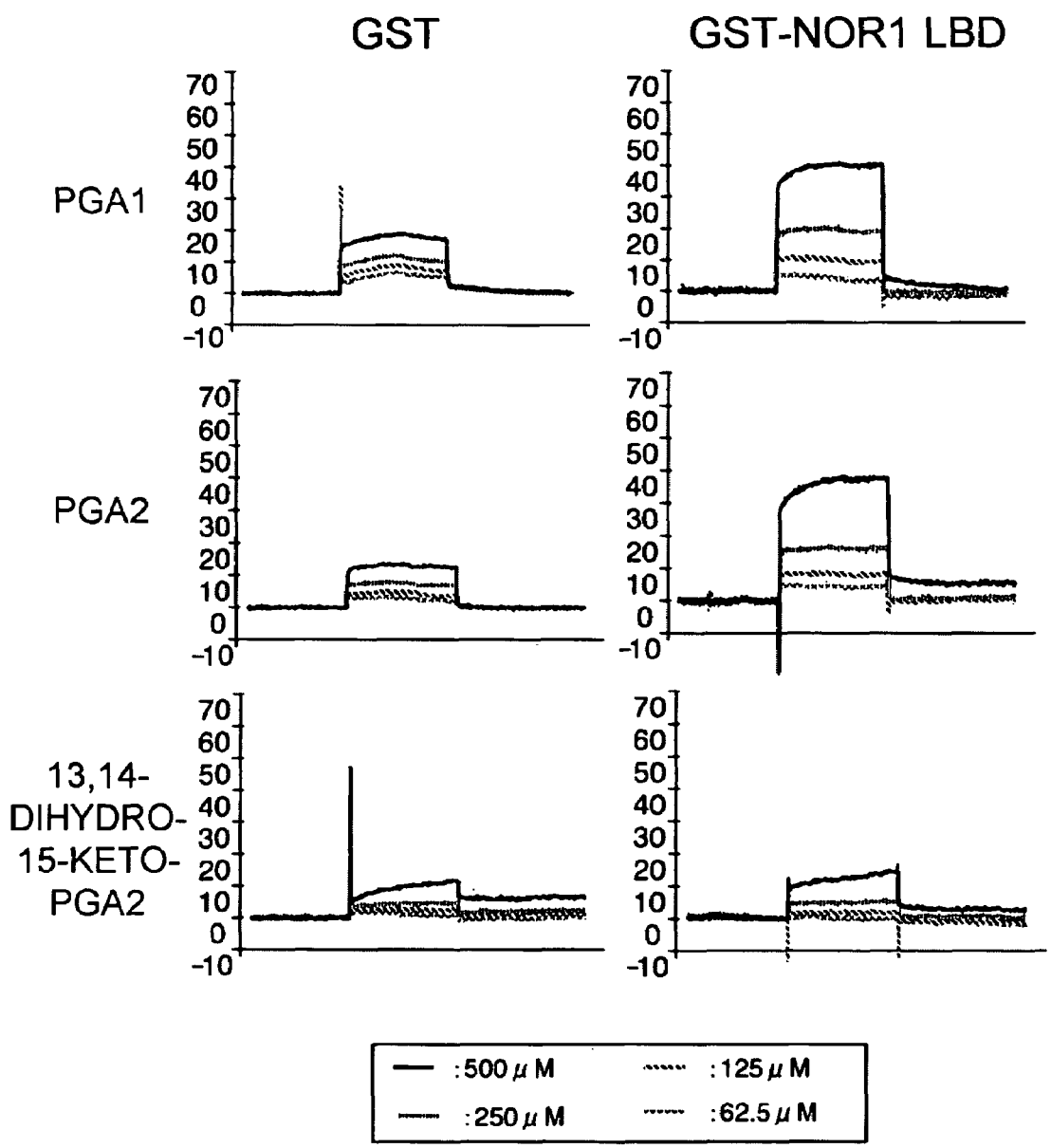
FIG. 8 shows diagrams that show the state, revealed with BIAcor S51, wherein PGA1 and PGA2 bind to the LBD of NOR-1. Glutathione S-transferase (GST) was used as a comparison control and 13,14-Dihydro-15-keto-PGA2 as a negative control.

In order to indisputably prove the ligand binding activity of the PGA derivatives to Nor1 demonstrated by the Mammalian Two Hybrid reporter system, GST-LBD of Nor1 was expressed in *E. coli* and purified. Through the comparison with GST, the sign of the binding of PGA1 and PGA2 to the LBD of Nor1 was detected using BIAcor S51 (FIG. 8). The negative control compound, 13,14-dihydro-15-keto-PGA2, did not show any activity in the reporter system and did not bind to LBD.

EXAMPLE 9

Enhancement of a gene that is suggested to have such apoptotic character in peripheral blood eosinophils in the remission stage due to therapy of atopic dermatitis corresponds well to the decrease in the number of peripheral blood eosinophils. Therefore, the expression induction of the gene is highly likely to correspond to therapeutic effects. Thus, the type of stimulation that causes expression of this gene in eosinophils was investigated in vitro.

Figure 9:
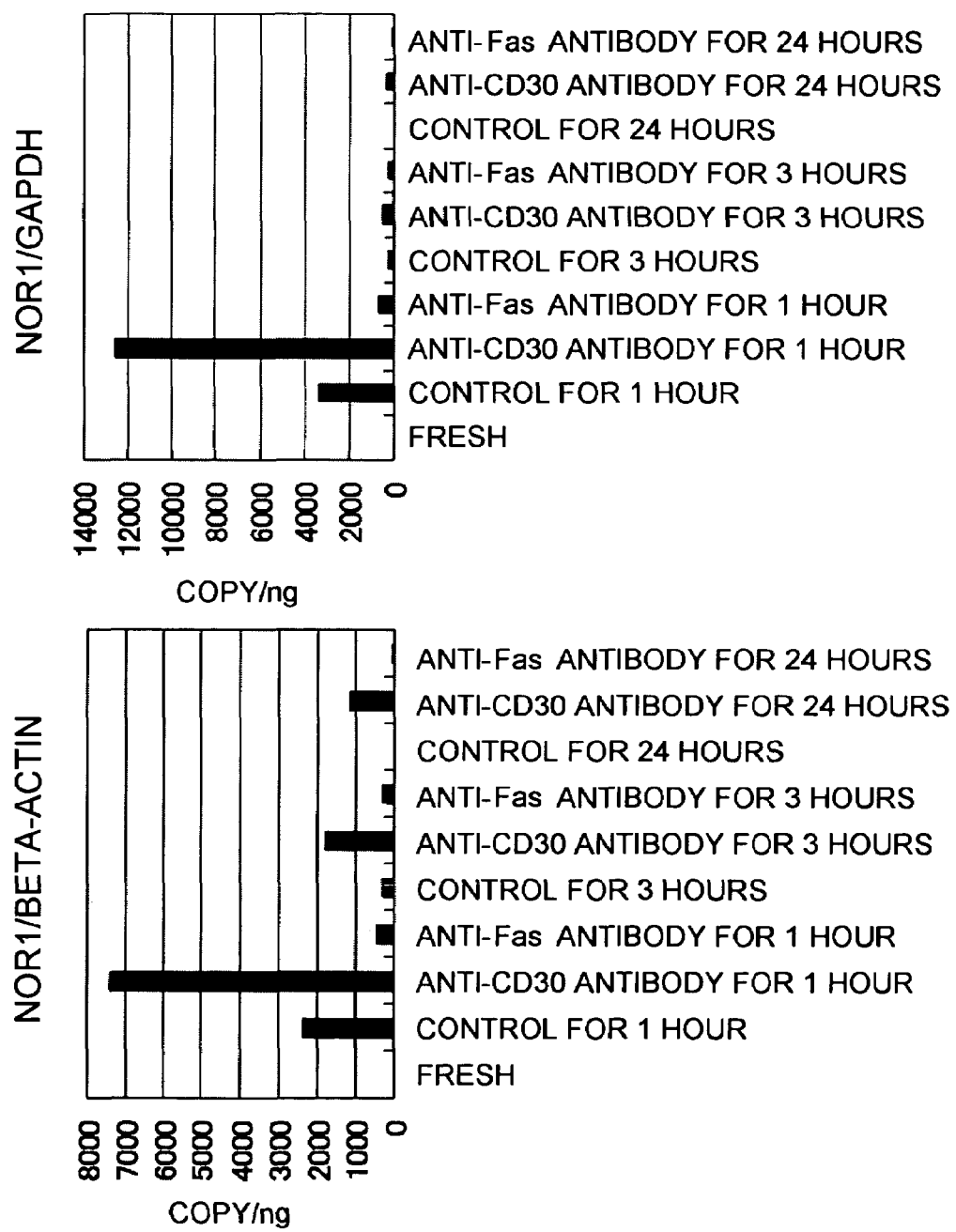
FIG. 9 shows graphs indicating the result of expression induction of NOR-1 due to apoptosis stimulation of peripheral blood eosinophils using anti-CD30 antibody or anti-Fas antibody. Values collected for beta-actin and GAPDH are shown.

A large amount of peripheral blood eosinophils were collected from healthy subjects, and cultured in suspension in a petri dish while suppressing their activation. The activation of the eosinophils via the stimulation with cytokines, such as IL-5 and IL-4, did not lead to the induction of Nor1. In contrast, when apoptosis of the cells was induced with anti-CD30 antibody, Nor1 was revealed to be dramatically induced in the cultured peripheral blood eosinophils during 1 to 3 hr treatment (Table 59, FIG. 9). The anti-CD30 antibody that has an agonistic activity against eosinophilic CD30 has recently been receiving attention, because it induces apoptosis of eosinophils via a specific intracellular pathway and may serve as a therapeutic agent for asthma. Table 59 below summarizes the apoptosis induction of human peripheral blood eosinophils.

TABLE 59

Apoptosis induction of human peripheral blood eosinophils

| | | Annexin V-positive cells (%) |
|---|---|---|
| Fresh | | 4.0 |
| Control | 1 hr | 2.30 |
| Anti-CD30 antibody | | 9.20 |
| Anti-Fas antibody | | 5.20 |
| Control | 3 hr | 4.50 |
| Anti-CD30 antibody | | 20.00 |
| Anti-Fas antibody | | 13.80 |
| Control | 24 hr | 11.70 |
| Anti-CD30 antibody | | 63.00 |
| Anti-Fas antibody | | 31.20 |

Figure 10:
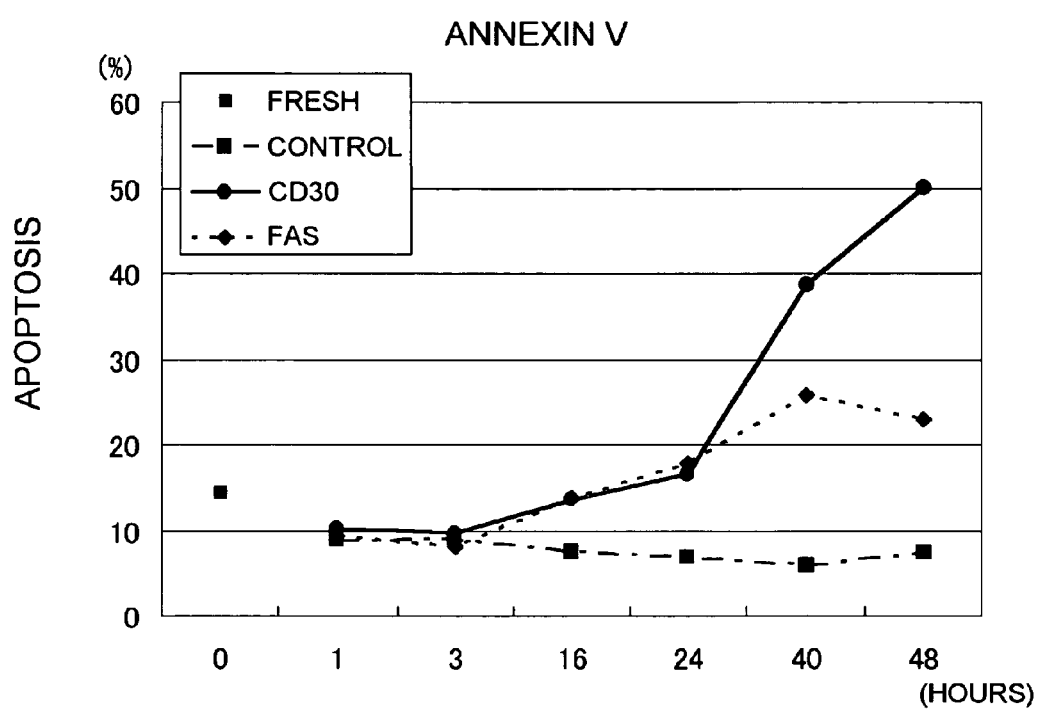
FIG. 10 shows a graph indicating the apoptosis induction effect due to the treatment of eosinophil-specific cell line, AML14.3D10, with anti-CD30 antibody or anti-Fas antibody.
Figure 11:
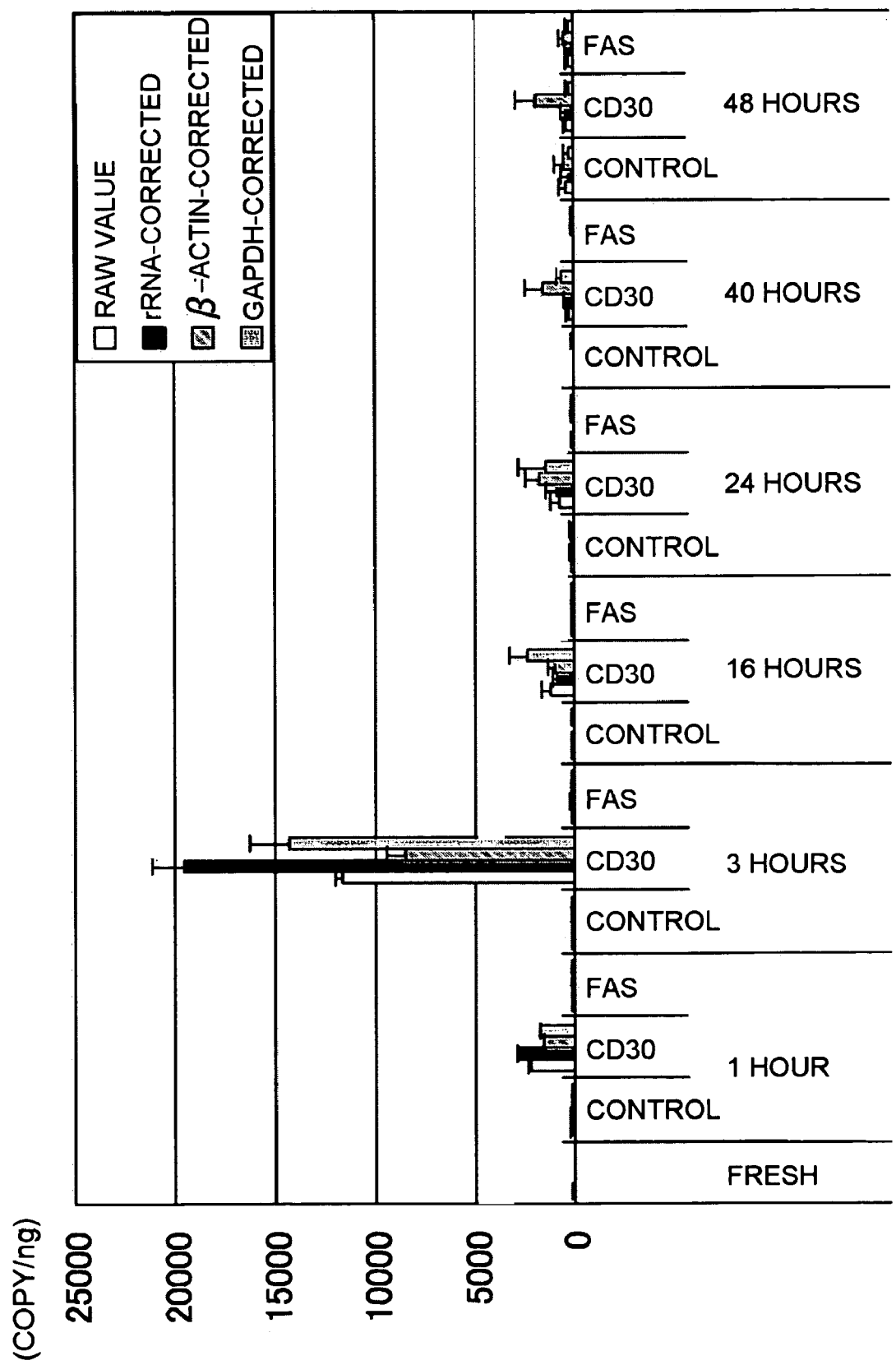
FIG. 11 shows a graph indicating the expression induction of NOR-1 due to the treatment of eosinophil-specific cell line, AML14.3D10, with anti-CD30 antibody or anti-Fas antibody.

Although the reaction was slower than with anti-CD30 antibody, apoptosis was induced with anti-Fas antibody. However, anti-Fas antibody did not induce Nor1. Thus, the apoptosis by anti-CD30 antibody accompanied by induction of Nor1 may occur through an eosinophil-specific apoptosis pathway that is different from the conventional pathway. Such phenomena (apoptosis induction and expression induction of Nor1) were similarly observed when AML14.3D10, an eosinophil-specific cell line, was treated with anti-CD30 antibody (FIGS. 10 and 11).

Figure 12:
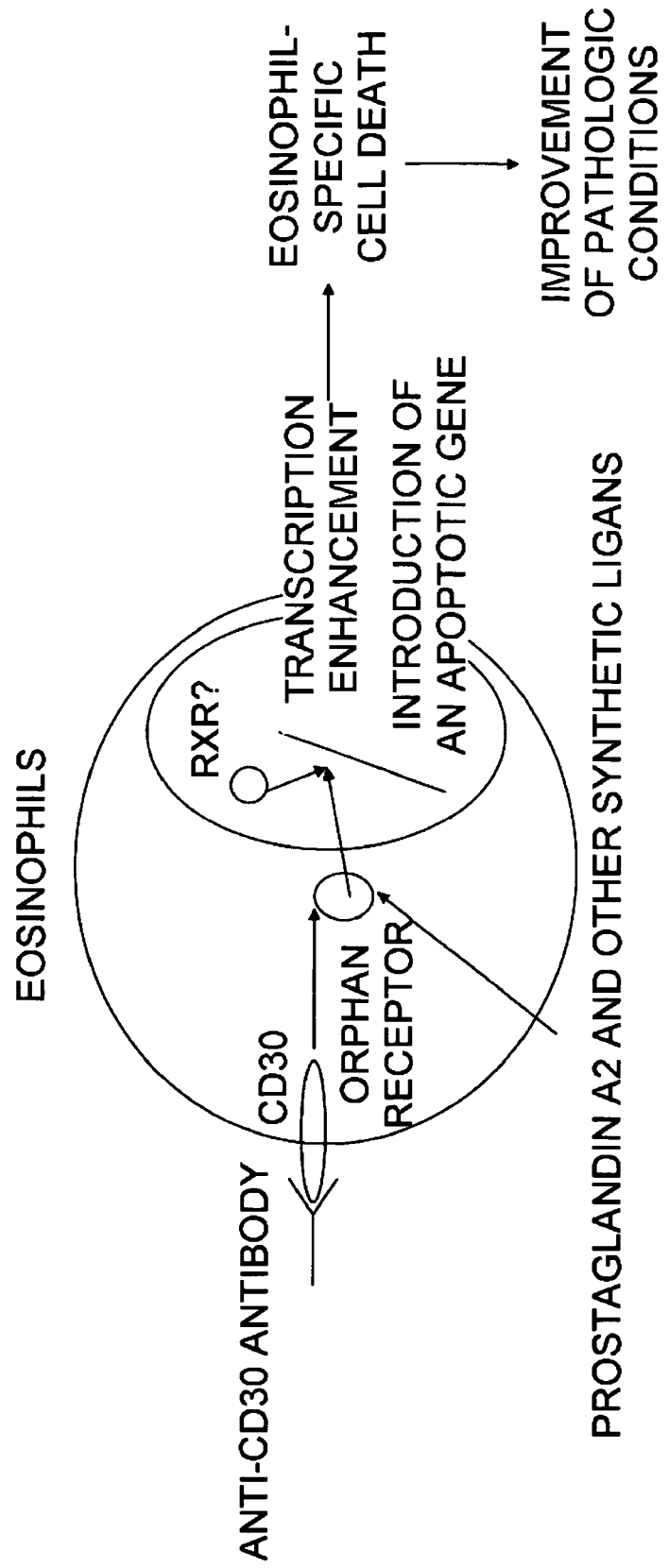
FIG. 12 shows a working hypothesis for an allergic disease treatment via eosinophil cell death caused by nuclear receptor Nur subfamily including Nor1.

It is very likely that such promotion of a pathway that specifically leads eosinophils to cell death through the enhancement of the function of Nor1 leads to the treatment of not only asthma but also various allergic diseases including atopic dermatitis investigated by the present inventors. An example of the therapeutic strategy intended by the present inventors is shown in FIG. 12.

EXAMPLE 10

Establishment of Transgenic (TG) Mice

Figure 13:
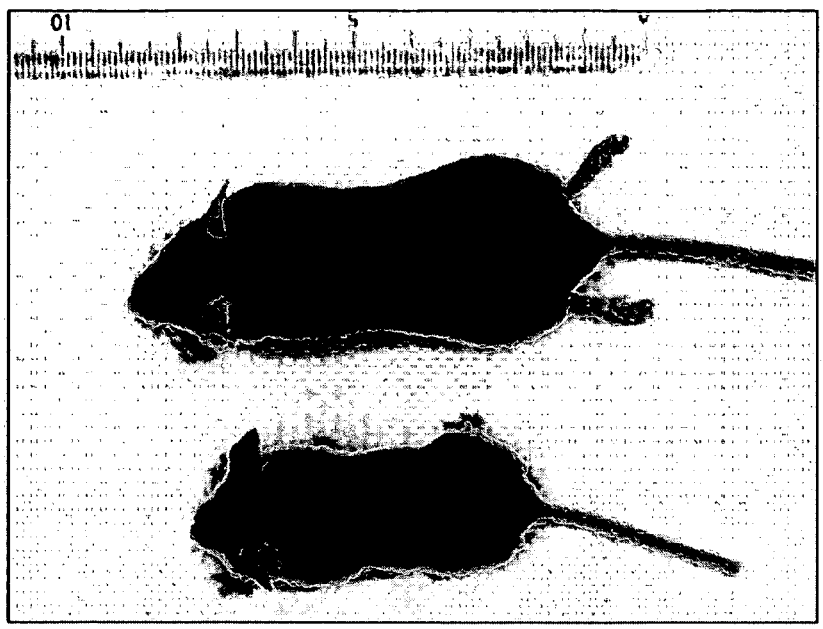
FIG. 13 shows a photograph of NOR-1 transgenic mouse and wild-type mouse. Characteristics such as, a decrease in the body weight to half, thymic atrophy and splenic atrophy were observed in the transgenic mouse.

A TG mouse in which the human Nor1 gene had been introduced under the actin promoter was successfully established (FIG. 13). The body weight of this mouse was only half of the wild type, and atrophy of the thymus and pancreas was observed. Pancreatic cells decreased in number and their activity declined. Such TG mice can be used as animal models for Nor1-mediated allergic disease analysis.

What is claimed is:

1. A method of testing for the remission stage of atopic dermatitis that is associated with a decrease in eosinophil cell number in a test subject having atopic dermatitis, said method comprising the steps of:
 (a) measuring the expression level of the NOR-1 gene in the eosinophil cells of the test subject having atopic dermatitis; and
 (b) comparing the expression level measured with the expression level of the NOR-1 gene in the eosinophil cells of the test subject during the exacerbation stage of atopic dermatitis,
wherein the remission stage of atopic dermatitis that is associated with a decrease in eosinophil cell number is indicated by an increase in the level of NOR-1 gene expression in the eosinophil cells of the test subject having atopic dermatitis as compared with that in the eosinophil cells of the test subject during the exacerbation stage of atopic dermatitis.

2. The testing method of claim 1, wherein the gene expression level is measured by cDNA PCR.

3. A method of assessing the effect of a therapy on an individual in the exacerbation stage of atopic dermatitis comprising:
 (a) measuring the expression level of the NOR-1 gene in the eosinophil cells of the individual before and after the therapy;
 (b) comparing the expression level of the NOR-1 gene measured before the therapy to that measured after the therapy; and
 (c) determining whether the test subject has had a decrease in eosinophil cell number after the therapy,
wherein an increase in the NOR-1 gene expression level and a decrease in eosinophil cell number after the therapy compared to that before the therapy indicate that the therapy has been effective.

4. The method of claim 3 wherein the NOR-1 gene expression level is measured by cDNA PCR.

* * * * *

UNITED STATES PATENT AND TRADEMARK OFFICE
CERTIFICATE OF CORRECTION

PATENT NO. : 7,115,373 B2
APPLICATION NO. : 10/608863
DATED : October 3, 2006
INVENTOR(S) : Ryoichi Hashida et al.

It is certified that error appears in the above-identified patent and that said Letters Patent is hereby corrected as shown below:

At Column 64, line 50, delete "NAPHTHALENE2AMINO4METHOXYCARBONYL" and insert therefor

--

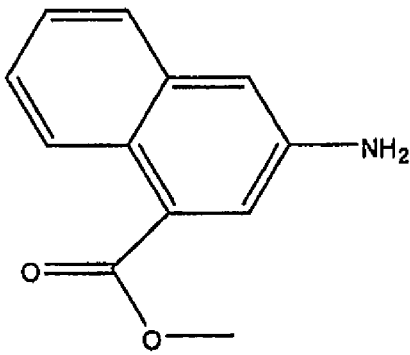

NAPHTHALENE2AMINO4METHOXYCARBONYL

--.

Signed and Sealed this

Twenty-eighth Day of August, 2007

JON W. DUDAS
*Director of the United States Patent and Trademark Office*